United States Patent
Cossler et al.

(10) Patent No.: US 12,278,005 B2
(45) Date of Patent: *Apr. 15, 2025

(54) ARTIFICIAL-INTELLIGENCE-BASED FACILITATION OF HEALTHCARE DELIVERY

(71) Applicant: University Hospitals Cleveland Medical Center, Cleveland, OH (US)

(72) Inventors: Nancy J. Cossler, Solon, OH (US); Jeffrey Alan Beers, Columbia Station, OH (US); Steven Mattlin, Cleveland, OH (US)

(73) Assignee: University Hospitals Cleveland Medical Center, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/816,867

(22) Filed: Aug. 2, 2022

(65) Prior Publication Data
US 2022/0383998 A1 Dec. 1, 2022

Related U.S. Application Data

(63) Continuation of application No. 15/900,009, filed on Feb. 20, 2018, now Pat. No. 11,437,125, which is a
(Continued)

(51) Int. Cl.
*G16H 10/60* (2018.01)
*G06N 20/00* (2019.01)
(Continued)

(52) U.S. Cl.
CPC ............ *G16H 10/60* (2018.01); *G16H 50/50* (2018.01); *G06N 20/00* (2019.01); *G16H 50/30* (2018.01); *G16H 50/70* (2018.01)

(58) Field of Classification Search
CPC ...................................................... G16H 10/60
(Continued)

(56) References Cited

U.S. PATENT DOCUMENTS 5,357,427 A * 10/1994 Langen ................. G16H 40/67
600/300
6,322,502 B1 11/2001 Schoenberg et al.
(Continued)

FOREIGN PATENT DOCUMENTS

KR 10-2007-011716 A 12/2007
WO 98/29790 A2 7/1998
WO WO-2013173715 A1 * 11/2013 ............. G06Q 40/00

OTHER PUBLICATIONS

Rideout, Karen; Adverse medical event reduction technologies: Identification of primary risk factors of adverse medical events using artificial neural networks; Carleton University (Canada). ProQuest Dissertations Publishing, 2006. MR16466 (Year: 2006).*
(Continued)

*Primary Examiner* — Hiep V Nguyen
(74) *Attorney, Agent, or Firm* — Amin, Turocy & Watson, LLP

(57) ABSTRACT

Techniques are provided that involve employing artificial intelligence (AI) to facilitate reducing adverse outcomes associated with healthcare delivery. In one embodiment, a computer implemented method comprises monitoring live feedback received over a course of care of a patient, wherein the live feedback comprises physiological information regarding a physiological state of the patient. The method further comprises employing AI to identify, based on the live feedback information, an event or condition associated with the course of care of the patient that warrants clinical attention or a clinical response. The method further comprises generating a response, based on the identification of the event or condition, that facilitates reducing an adverse
(Continued)

outcome of the course of care, wherein the response varies based on a type of the event or condition, and providing the response to a device associated with an entity involved with treating the patient in association with the course of care.

18 Claims, 21 Drawing Sheets

Related U.S. Application Data continuation-in-part of application No. 14/304,593, filed on Jun. 13, 2014, now Pat. No. 10,529,445.

(51) Int. Cl.
  *G16H 50/30* (2018.01)
  *G16H 50/50* (2018.01)
  *G16H 50/70* (2018.01)

(58) Field of Classification Search
  USPC .............................................. 705/3
  See application file for complete search history.

(56) References Cited

U.S. PATENT DOCUMENTS

| | | | |
|---|---|---|---|
| 7,374,535 B2 | 5/2008 | Schoenberg et al. | |
| 7,693,727 B2 | 4/2010 | Moore | |
| 7,778,851 B2 | 8/2010 | Schoenberg et al. | |
| 7,831,450 B2 | 11/2010 | Schoenberg et al. | |
| 7,899,683 B2 | 3/2011 | Schoenberg et al. | |
| 8,027,846 B2 | 9/2011 | Schoenberg et al. | |
| 8,376,943 B2 | 2/2013 | Kovach et al. | |
| 2002/0177758 A1 | 11/2002 | Schoenberg et al. | |
| 2002/0177759 A1 | 11/2002 | Schoenberg et al. | |
| 2003/0036687 A1 | 2/2003 | Schoenberg et al. | |
| 2005/0125256 A1 | 6/2005 | Schoenberg et al. | |
| 2005/0228243 A1* | 10/2005 | Bardy ................ | G16H 50/30 600/300 |
| 2006/0085223 A1* | 4/2006 | Anderson ............ | G16H 20/17 705/2 |
| 2006/0265249 A1 | 11/2006 | Follis et al. | |
| 2007/0022075 A1 | 1/2007 | Horvitz et al. | |
| 2008/0208618 A1 | 8/2008 | Schoenberg et al. | |
| 2008/0235057 A1* | 9/2008 | Weidenhaupt ......... | G16H 50/20 705/3 |
| 2009/0018882 A1* | 1/2009 | Burton ................ | G06Q 10/0633 705/7.27 |
| 2009/0082640 A1 | 3/2009 | Kovach et al. | |
| 2009/0147011 A1 | 6/2009 | Buck et al. | |
| 2009/0259487 A1 | 10/2009 | Rao et al. | |
| 2010/0250196 A1 | 9/2010 | Lawler et al. | |
| 2011/0004110 A1* | 1/2011 | Shusterman ........... | G16H 50/20 600/509 |
| 2011/0004489 A1 | 1/2011 | Schoenberg et al. | |
| 2011/0201899 A1* | 8/2011 | Price .................... | A61B 5/486 600/27 |
| 2012/0089553 A1 | 4/2012 | Mollicone et al. | |
| 2012/0215556 A1* | 8/2012 | Warner ................. | G16H 40/20 705/2 |
| 2012/0303388 A1 | 11/2012 | Vishnubhatla et al. | |
| 2013/0151285 A1 | 6/2013 | McLaren et al. | |
| 2013/0152005 A1 | 6/2013 | McLaren et al. | |
| 2013/0191165 A1 | 7/2013 | MacDonald et al. | |
| 2013/0218053 A1 | 8/2013 | Kaiser et al. | |
| 2014/0028464 A1* | 1/2014 | Garibaldi .............. | G16H 50/70 340/870.02 |
| 2014/0142970 A1* | 5/2014 | Baronov .............. | A61B 5/7275 705/2 |
| 2016/0073880 A1* | 3/2016 | Mensinger ........... | A61B 5/0002 340/870.07 |
| 2016/0098536 A1* | 4/2016 | Dettinger ............... | G09B 23/28 705/2 |

OTHER PUBLICATIONS

McDonagh, Joanne; Development of an automated screening tool for diabetic retinopathy using artificial intelligence; University of Glasgow (United Kingdom). ProQuest Dissertations Publishing, 2005. 10753981. (Year: 2015).*
McDonagh, Joanne; Development of an automated screening tool for diabetic retinopathy using artificial intelligence; University of Glasgow (United Kingdom). ProQuest Dissertations Publishing, 2005. 10753981 (Year: 2005).*
International Search Report and Written Opinion for PCT Application Serial No. PCT/US2015/035359 dated Sep. 7, 2015, 12 pages.
Non-Final Office Action received for U.S. Appl. No. 14/304,593 dated Sep. 19, 2016, 18 pages.
Final Office Action received for U.S. Appl. No. 14/304,593 dated Feb. 1, 2017, 23 pages.
Non-Final Office Action received for U.S. Appl. No. 14/304,593 dated Jul. 7, 2017, 24 pages.
Final Office Action received for U.S. Appl. No. 14/304,593 dated Apr. 17, 2018, 26 pages.
Non-Final Office Action received for U.S. Appl. No. 14/304,593 dated Oct. 25, 2018, 20 pages.
Final Office Action received for U.S. Appl. No. 14/304,593 dated Mar. 20, 2019, 24 pages.
Final Office Action received for U.S. Appl. No. 15/900,009 dated Oct. 28, 2019, 34 pages.
Final Office Action received for U.S. Appl. No. 15/900,009 dated May 28, 2020, 24 pages.
Non-Final Office Action received for U.S. Appl. No. 15/900,009 dated Nov. 3, 2020, 20 bages.
Final Office Action received for U.S. Appl. No. 15/900,009 dated Jun. 8, 2021, 28 pages.
Non-Final Office Action received for U.S. Appl. No. 16/707,606 dated Jun. 7, 2021, 45 pages.
Non-Final Office Action received for U.S. Appl. No. 15/900,009 dated Sep. 20, 2021, 25 pages.
Final Office Action received for U.S. Appl. No. 16/707,606 dated Sep. 24, 2021, 21 pages.
Non-Final Office Action received for U.S. Appl. No. 16/707,606 dated Jan. 28, 2022, 36 pages.
Notice of Allowance received for U.S. Appl. No. 15/900,009 dated Apr. 28, 2022, 73 pages.
Phansalkar S., "Advanced methods for detection of adverse drug events in clinical notes", The University of Utah, ProQuest Dissertations Publishing, 2007, 135 pages.
Final Office Action received for U.S. Appl. No. 16/707,606 dated Jul. 28, 2022, 17 pages.
Notice of Allowance received for U.S. Appl. No. 16/707,606 dated Sep. 13, 2022, 36 pages.
Li, Z., "Non-linear Adaptive Bayesian Filtering for Brain Machine Interfaces", Duke University, ProQuest Dissertations Publishing, 2010, 222 pages.
U.S. Appl. No. 15/900,009, filed Feb. 20, 2018.
U.S. Appl. No. 14/304,593, filed Jun. 13, 2014.
U.S. Appl. No. 16/707,606, filed Dec. 9, 2019.

* cited by examiner

FIG. 7A

| hours | 0 | 4 | 8 | 12 | 16 | 20 | 24 |
|---|---|---|---|---|---|---|---|
| Admit | | | | | | | |
| Tab | | | | 712 | | | |
| Tab | | | | | | | |

FIG. 7B

Patient Name": 38 yr old, 37 wks gestation, G3P2 Plan: TOLAC

| hours | 0 | 4 | 8 | 12 | 16 | 20 | 24 |
|---|---|---|---|---|---|---|---|
| Admit | | admit 8 hrs | | | | | |
| Stage | | Stage 1 8hr | | | | | |
| Category | | Category I | | | | | |

FIG. 7C

Patient Name": 38 yr old, 37 wks gestation, G3P2 Plan: TOLAC

| hours | 0 | 4 | 8 | 12 | 16 | 20 | 24 |
|---|---|---|---|---|---|---|---|
| Admit | | | Admit 12hr | | | | |
| ROM | | | ROM 4hr | | | | |
| Stage | | | Stage I | | | | |
| Category | | | Category I | | | | |

FIG. 7D

Patient Name": 38 yr old, 37 wks gestation, G3P2 Plan: TOLAC

| hours | 0 | 4 | 8 | 12 | 16 | 20 | 24 |
|---|---|---|---|---|---|---|---|
| Admit | | | | | Admit 20 hr | | |
| ROM | | | | | ROM 12 hr | | |
| Cytotec | | | | | Cytotec 4 hr | | |
| Stage | | | | Stage I | | | |
| Category | | | | | Category II | | |

Patient Name": 38 yr old, 37 wks gestation, G3P2 Plan: TOLAC

| hours | 0 | 4 | 8 | 12 | 16 | 20 | 24 |
|---|---|---|---|---|---|---|---|
| Admit | | | admit 24hr | | | | |
| ROM | | | | | ROM 16hr | | |
| Cytotec | | | | | | cytotec 8 hr | |
| Pitocin | | | | | | Pitocin 4hr | |
| Stage | Stage 1 | | | | | Stage II | |
| Category | | | | | | Category II | |

FIG. 7E

| Labor Clinical Decision Data Display | | | | | | | | | | | |
|---|---|---|---|---|---|---|---|---|---|---|---|
| Date | 1/7/2014 | | | | | | | | | | |
| Clock | 1500 | 1600 | 1700 | 1800 | 1900 | 2000 | 2100 | 2200 | 2300 | 2400 | |
| Number of hours | 1 | 2 | 3 | 4 | 5 | 6 | 7 | 8 | 9 | 10 | |
| Decision to Induce 808 | | | | | | | | | 828 | | |
| Active Phase 810 | | | | | | | | | 830 | | |
| Rupture of Membranes 812 | | | | | | | | | | 832 | |
| Induction Pharmaceutical 814 | Cytotec #1 834 | | | | | | Cytotec #2 | | | | |
| Oxytocin 816 | | | | | | | | | 838 | | |
| Dilatation 818 | | | | | | 836 | | | 840 | | |
| Fetal Heart Baseline Rate 820 | Baseline FHR 156 | | | | | | | | 842 | | |
| Deceleration >2 minutes 822 | | | | | | | | | | | |
| Maternal Temperature >= 38.0 C — 824 | | | | | | | | | | | |
| Maternal Hypertension > 160/110 — 826 | | | | | | | | | | | |
| Other | | | | | | | | | | | |

| Labor Clinical Decision Data Display | | | | | | | | | | | | | | | | |
|---|---|---|---|---|---|---|---|---|---|---|---|---|---|---|---|---|
| Date | 1/8/2014 | | | | | | | | | | | | | | | |
| Clock | 0 | 100 | 200 | 300 | 400 | 500 | 600 | 700 | 800 | 900 | 1000 | 1100 | 1200 | 1300 | 1400 |
| Number of hours | 11 | 12 | 13 | 14 | 15 | 16 | 17 | 18 | 19 | 20 | 21 | 22 | 23 | 24 | 25 |
| Decision to Induce | | | | | | | | | Decision to Induce 25 hours | | | | | | |
| Active Phase | | | | | | | | | | Active Phase 17 hours | | | | | |
| Rupture of Membranes | | | | | | | | | | | Rupture of Membranes 16 hours | | | | |
| Induction Pharmaceutical | | | | | | | | | | | | | | | |
| Oxytocin | | | | | | | | | | Oxytocin at rate of 20 for 5 hours | | | | | |
| Dilatation | 1 cm | | | 2 cm | | | 3 cm | | 4 cm | 5 cm | | 6 cm | 7 cm | 8 cm | |
| Fetal Heart Baseline Rate | | | | | | | | Decel | | | | | | Baseline FHR 156 | |
| Deceleration >2 minutes | | | | | | | | | | | | | | | |
| Maternal Temperature >= 38.0 C | | | | | | | | | | | | | | | |
| Maternal Hypertension > 160/110 | | | | | | | | | | | | | | | |
| Other | | | | | | | | | | | | | | | |

ARTIFICIAL-INTELLIGENCE-BASED FACILITATION OF HEALTHCARE DELIVERY

RELATED APPLICATION

This application is continuation of and claims priority to U.S. patent application Ser. No. 15/900,009 filed on Feb. 20, 2018, entitled "ARTIFICIAL-INTELLIGENCE-BASED FACILITATION OF HEALTHCARE DELIVERY", which is a continuation-in-part of and claims priority to U.S. patent application Ser. No. 14/304,593 filed on Jun. 13, 2014, now U.S. Pat. No. 10,529,445, entitled "GRAPHICAL USER INTERFACE FOR TRACKING AND DISPLAYING PATIENT INFORMATION OVER THE COURSE OF CARE". The entireties of the aforementioned applications are incorporated by reference herein.

TECHNICAL FIELD

This disclosure relates to systems, computer-implemented methods, apparatus and/or computer program products that employ artificial intelligence (AI) tactics to facilitate healthcare delivery.

SUMMARY

The following presents a summary to provide a basic understanding of one or more embodiments of the invention. This summary is not intended to identify key or critical elements, or delineate any scope of the different embodiments or any scope of the claims. Its sole purpose is to present concepts in a simplified form as a prelude to the more detailed description that is presented later. The subject disclosure relates to employing artificial intelligence (AI) to facilitate reducing adverse outcomes associated with healthcare delivery.

In one embodiment, a system is provided that comprises a memory that stores computer executable components and a processor that executes the computer executable components stored in the memory. The computer executable components comprise a monitoring component configured to monitor live feedback received over a course of care of a patient, wherein the live feedback comprises physiological information regarding a physiological state of the patient, and a significant event/condition identification component configured to employ AI to identify, based on the live feedback information, an event or condition associated with the course of care of the patient that warrants clinical attention or a clinical response. The computer executable components further comprise a response component configured to determine a response, based on the identification of the event or condition, that facilitates reducing an adverse outcome of the course of care, wherein the response varies based on a type of the event or condition, and wherein the response component is further configured to generate the response and provide the response to a device associated with an entity involved with treating the patient in association with the course of care.

In some implementations, the significant event/condition identification component can be configured to identify the event or condition using machine learning analysis of historical healthcare delivery information regarding same or similar courses of care and one or more standard operating procedures defined for the course of care. The significant event/condition identification component can further be configured to identify the event or condition based on information regarding a medical health history of the patient. In another implementation, the significant event/condition identification component can be further configured to identify the event or condition based on information regarding one or more clinicians responsible for treating the patient in association with the course of care, including at least one of: a current level of fatigue of the one or more clinicians, a current workload of the one or more clinicians, and historical performance information for the one or more clinicians.

The response generated by the response component can vary. In one implementation, the response can comprise a notification regarding the significant event or condition and wherein the response component further comprises a notification component configured to generate and send the notification to the device. The notification can comprise a mechanism for providing an acknowledgment indicating the notification was received, and wherein the response component further comprises an acknowledgment component configured to track information regarding whether the acknowledgment was received and timing of reception of the acknowledgment. In another implementation, the response component comprises an interface component and wherein the response comprises updating, by the interface component, a graphical user interface in real-time to reflect occurrence of the event or condition, wherein the graphical user interface tracks events and conditions associated with the course of care in real-time. With this implementation, the system can further comprise a monitoring parameter update component configured to determine one or more parameters related to the event or condition, and wherein the interface component is further configured update the graphical use interface to comprise information that tracks the one or more parameters. The system of claim can further comprise a prioritization component configured to determine a priority order of the significant events and conditions and wherein the interface component is further configured to update the graphical user interface to reflect the priority order.

In various additional implementations, the response can comprise a recommended clinical response for performance by one or more clinicians responsible for providing medical treatment to the patient in association with the course of care. With these implementations, the response component can comprise a recommendation component configured to employ AI to determine the recommended clinical response based on the event or condition, and provide the one or more clinicians with information, (e.g., in the form of a notification or the like), recommending performance of the recommended clinical response. In some implementations, the recommendation component can be configured to determine the response based on information regarding the one or more clinicians, including at least one of, a current level of fatigue of the one or more clinicians, a current workload of the one or more clinicians, and historical performance information for the one or more clinicians.

In some embodiments, elements described in connection with the disclosed systems can be embodied in different forms such as a computer-implemented method, a computer program product, or another form.

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which:

FIGS. 7A-7E present an example patient tracking interface as it evolves from a default shell or form over a course of patient care in accordance with various aspects and embodiments described herein.

FIGS. 8A-8C illustrates another example user interface that facilitates tracking and displaying patient information over the course of care in accordance with various aspects and embodiments described herein.

DETAILED DESCRIPTION

Figure 1:
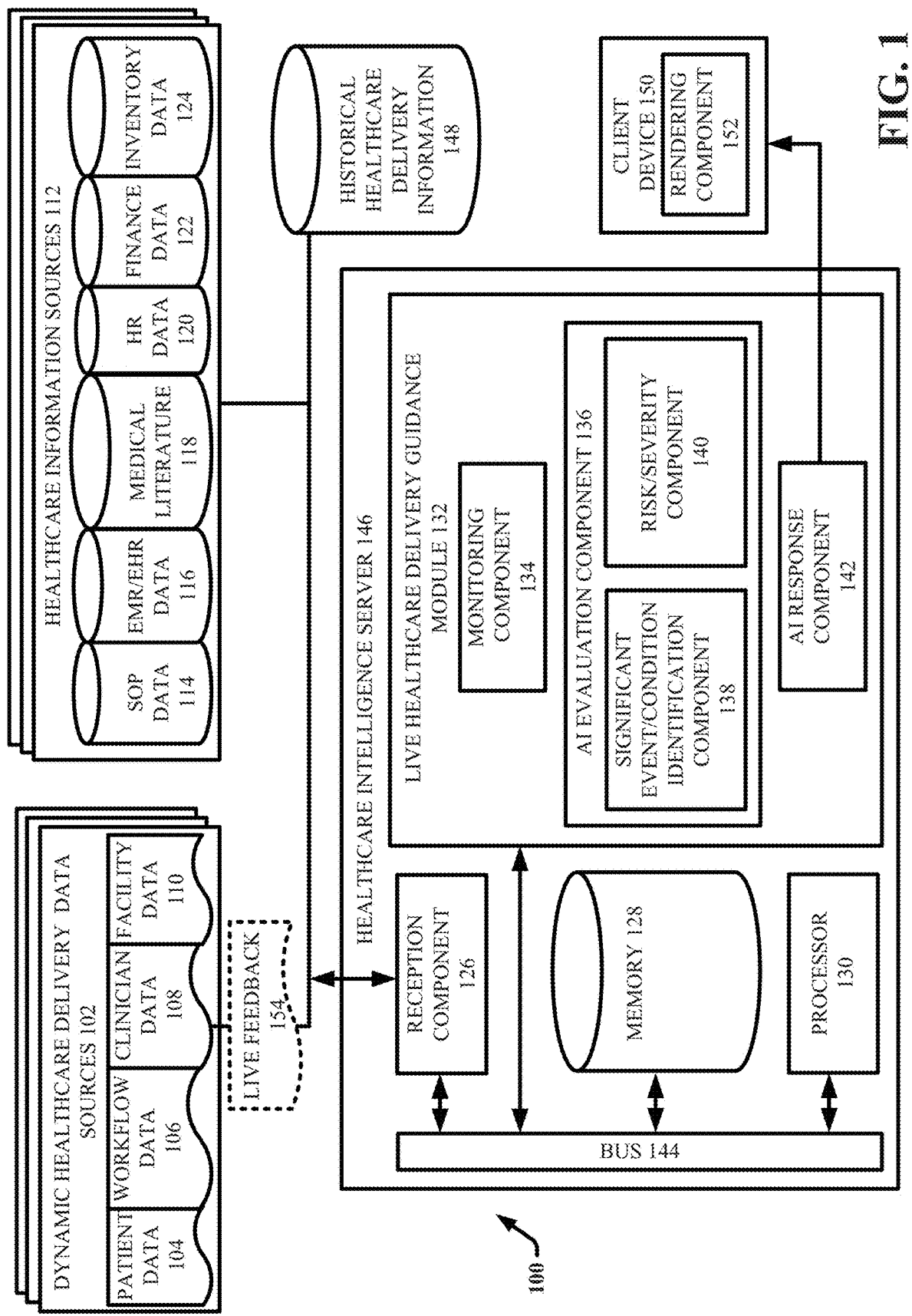
FIG. 1 illustrates an example system that facilitates healthcare delivery using AI tactics in accordance with various aspects and embodiments described herein.

The following detailed description is merely illustrative and is not intended to limit embodiments and/or application or uses of embodiments. Furthermore, there is no intention to be bound by any expressed or implied information presented in the preceding Summary section or in the Detailed Description section.

The subject disclosure provides systems, computer-implemented methods, apparatus and/or computer program products that employ artificial intelligence (AI) tactics to facilitate healthcare delivery. AI is intelligence displayed by machines (e.g., computers), in contrast with the natural intelligence displayed by humans and other animals. Colloquially, the term artificial intelligence is applied when a machine mimics cognitive functions that humans associate with other human minds, such as learning and problem solving. AI makes it possible for machines to learn from experience, adjust to new inputs and perform human-like tasks using machine learning. Machine learning is an application of AI that provides systems the ability to automatically learn and improve from experience without being explicitly programmed. Machine learning focuses on the development of computer programs that can access data, apply intelligent reasoning based the data, and generate educated decisions based that reasoning.

One or more embodiments of the disclosed subject matter leverage information from various data sources related to all aspects of healthcare delivery and employ machine learning to develop and apply an AI system that can automatically make determinations and inferences in a live healthcare setting that are directed to optimize the performance of clinicians in real-time. In this regard, using one or more types of machine learning algorithms and various healthcare data sources, the AI system can learn substantially all aspects of how healthcare delivery should be provided by a healthcare organization to achieve optimal clinical and financial outcomes. For example, the AI system can evaluate historical information that identifies tracked parameters related to clinical workflow events and patient conditions in association with past medical procedures or healthcare delivery scenarios. The AI system can also access and evaluate information including but not limited to: standard operating (SOP) information for one or more healthcare organizations that define standard operating procedures for different clinical scenarios and procedures, electronic medical record (EMR) and/or electronic health record (EHR) data for patients, medical literature that includes textbook information regarding all aspects of healthcare delivery, human resources (HR) data that identifies capabilities and performance information for clinicians employed at a healthcare organization, finance information that provides financial costs associated with different aspects of healthcare delivery, and inventory data that identifies available medical supplies and equipment.

Using one or more machine learning algorithms, the AI system can reason on the information provided by one or more of these data sources to determine the parameters, parameter values, and relationships between different parameters and parameter values that correlate to positive and negative clinical and financial outcomes associated with one or more aspects of healthcare delivery. In some embodiments, the AI system can determine or infer events and conditions that are clinically significant and warrant medical attention and/or acknowledgment (referred to herein as a significant event or condition). For example, the AI system can learn that a drop in blood pressure below a particular threshold for a patient with a particular condition while undergoing a particular surgery is clinically significant because of a probability the patient may have a stroke. The drop-in blood pressure in this context can be characterized as a significant event. In another example, the labor process involves key data and decision points over the course of labor that can affect the outcome of the baby, including lifelong cognitive and physical functions. According to this example, the AI system can characterize certain physiological conditions and events, (associated with the mother and/or the infant) that correspond to these key data and decision points as clinically significant. In some implementations in association with identifying significant events or conditions, the AI system can further determine patterns in the data that correspond to a defined diagnosis of a condition or complication affecting a patient. For example, the AI system can determine that a particular pattern in physiological parameters and symptoms expressed by pregnant patient indicate the onset of labor. With these implementations, the AI system can further identify a significant event or condition by its medical diagnosis or known name that is used to refer to the type of event or condition in the medical field (e.g., generally by all medical practitioners or internally by a particular medical organization).

In one embodiment, the AI system can employ a risk based analysis to determine or infer whether to characterize a condition or event as clinically significant. In this regard, the AI system can determine or infer a level of risk/severity associated with an event or condition based on probability that an adverse outcome would occur if the event or condition was not acknowledged and/or responded to over the course of care and further based on level of clinical and financial severity associated with the adverse outcome. The AI system can further be configured to characterize events or conditions associated with a risk/severity level above a threshold level as being significant. In other implementation, the AI system can further determine a score to associate with a significant event or condition that reflects its level of risk/severity.

In one or more embodiments, the AI system can perform and/or apply this evidence based reasoning to facilitate clinical decisions in real-time based on feedback regarding various aspects of a current clinical scenario. In this regard, the AI system can consider and evaluate the many different factors that are relevant to a current patient and a current clinical scenario in view of the information learned from and/or provided by the various data sources to determine and provide clinicians with evidence based information in real-time that can facilitate optimizing care.

For example, with respect to a particular healthcare facility, the feedback information can include dynamic information regarding monitored clinical events and conditions associated with patients, monitored activities of clinicians involved with treating the patients, and monitored contextual parameters regarding the context of the healthcare environment at the facility as a whole (e.g., locations of resources, status of resources, and the like). In another example, the feedback can include parameters related to (but not limited to): patient data that indicates or identifies aspects of a current physiological state and/or condition of a patient, workflow data that tracks clinical treatment performed for the patient by one or more clinicians during a current procedures or course of care, and clinician data that reflects current clinicians treating the patient, clinicians available to treat the patient, timing of availability, current workload of the clinicians (e.g., number of patients), mental and physiological status of the clinicians, and the like. In one example implementation, the AI system can receive this feedback over a course of care of a patient, and using the machine learning analysis discussed above, identify conditions and events that are clinically significant (e.g. warrant medical attention and/or acknowledgment). For example, in association with identifying significant events or conditions the AI system can evaluate parameters in the real-time feedback regarding the patient's current physiological state, in view of the medical history of the patient, historical data associated with same or similar clinical scenarios, one or more SOPs relevant to the current clinical scenario, medical literature related to the course of care, and the like.

In some embodiments, based on identification of a clinically significant event or condition, the AI system can be configured to notify one or more clinicians (e.g., the clinician treating the patient for which the clinically significant event or condition is observed) regarding the clinically significant event or condition. For example, in one implementation, the AI system can facilitate generating and displaying a visual notification on a display associated with the one or more clinicians. In some implementations, the AI system can further require an authoritative clinician to provide feedback indicating the notification was seen and considered.

In other embodiments, the AI system can further evaluate the historical information and/or the information provided by various additional healthcare data sources to determine or infer an appropriate response to an identified clinically significant event or condition. For example, using machine learning, the AI system can determine that a particular significant event or conditions warrants additional monitoring, warrants notifying an appropriate clinician, and/or requires a particular clinical reaction by one or more clinicians (e.g., performance of a particular procedure, administering of a particular pharmaceutical, etc.). In some implementations, in association with determining an appropriate response, the AI system can consider a risk or severity level associated with the condition or event. For example, the AI system can be configured notify a nurse of a low risk condition and notify the attending physician if the condition is high risk.

Further, in some embodiments, if the identified clinically significant condition or event warrants performance of an action (e.g., performance of a particular procedure, administering of a particular pharmaceutical, etc.) by one or more clinicians, the AI system can further be configured to determine or infer the action using machine learning analysis of the feedback in view of the information provided by the various data sources. The AI system can further recommend the action for performance by an appropriate clinician. For example, the AI system can consider information regarding historical reactions performed in same or similar clinical scenarios involving the event or condition, in view of one or more relevant SOPs and further in view of variable factors relevant to the current context, such as but not limited to, factors associated with the current patient as found in the patients EMR (e.g., other conditions of the patient, allergies, preferences, etc.), available resources (e.g., medical supplies and instruments that may be needed), available clinicians, capabilities of the clinicians, fatigue levels of the clinicians, and other possible factors relevant to the current context of the entire healthcare facility and the patient and the like. In some implementations, the AI system can also perform a risk based analysis to facilitate determining the best response. The risk based analysis can involve both clinical and financial risk. In some implementations, the AI system can further manage delegation of tasks and resources of a healthcare facility in real-time based on evaluation of the current states and needs of all patients, the capabilities of available clinicians, the current workload of available clinicians, and the like. For example, the AI system can determine a priority order for performance of responses to high risk or critical patient conditions/events, direct clinicians to provide treatment based on the priority order, and delegate clinicians to perform certain tasks that they are most proficient in, and the like.

In another embodiment a system is provided that includes a patient tracking tool that facilitates monitoring patient care events and conditions over the course of patient care. The patient tracking tool can include an interface component configured to generate a graphical user interface (GUI) that facilitates tracking a course of patient care. In an aspect, at the time a patient is admitted or received, information regarding the patient's medical history, diagnosis and in some implementations, a plan for the patient care (e.g., a specific procedure to be performed), can be received using the patient tracking tool. The patient tracking tool can further generate a GUI including a visualization that graphical and/or visually presents information representative of tracked patient events and conditions over the course of care. For example, in one or more embodiments, the visualization can include a chart with a date and hours timeline that runs horizontally (e.g., left to right or an X axis) and a plurality of data fields that extend vertically (e.g., from top to bottom or a Y axis) and below the hours timeline near the left side of the interface. For example, a series of ten to fifteen data fields related to patient conditions and/or patient care events associated with the plan for patient care can be displayed along a vertical axis tangential from the timeline. In an aspect, the data fields can be associated with a drop-down input menu that allows a user to select an input option from a plurality of preconfigured input options associated with the data field.

In one or more implementations, received input regarding a condition of the patient and/or a clinical event (e.g., medical treatment provided, administering of a drug, etc.) data can start a timeline associated with a patient condition or patient care event. Once a timeline is started, the patient tracking tool can be configured to extend the timeline across the interface until new data is received indicating a change in the patient condition or patient care event. In another aspect, received input data can identify a particular time point that a key event or condition occurred during care. A timeline or key event can be represented by a color bar running horizontally right to left across the interface. In some implementations, characteristics associated with a timeline or key event can be included in the form of text or a symbol located at the tip of the color bar.

In an exemplary embodiment, the subject patient tracking tool can facilitate tracking patient care during a course of labor. As noted above, there are key data and decision points during labor that can that guide the physician in their scope of clinical decision making. These key data and decision points are difficult to track for each patient in a clear and concise fashion over the length of labor. For example, management of a patient in labor may be brief, over a few hours, or may last several days. Clinicians in most hospital based services are limited to 8 or 12 hours "on duty" time frames or "shifts." Accordingly, the care of a mother in labor management often crosses through the care of many clinicians. For example, depending on the patient care setting, clinicians involved with care can include attending medical doctors (MDs), residents, interns, nurse midwives, registered nurses (RNs), licensed practical nurses (LPNs), patient care assistants and doulas interacting with the laboring patient. In addition, many clinicians often cover multiple laboring patients at once and in some cases, information regarding a patient's labor is communicated to a remote physician to make patient care decisions based on the communicated information. The subject patient tracking tool can provide clinicians with comprehensive picture of the key data and decision points during labor management. Therefore, the subject patient tracking tool can facilitate accurate and effective communication from one clinician to another over the course of a patient's labor and delivery and facilitate keeping track of up to the moment data as a clinician moves between multiple laboring patients.

Various aspects of the disclosed subject matter are exemplified in association with tracking and providing automated evidence based clinical reasoning regarding patient care over the course of labor. However, it should be appreciated that the disclosed subject matter is not limited to the labor process. For example, the disclosed techniques can be applied to facilitate clinical decisions associated with various clinical scenarios. For example, the disclosed techniques can be employed to facilitate clinical decisions associated with performance of various medical procedures, in emergency room setting, in an outpatient setting, and the like.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Referring now to the drawings, with reference initially to FIG. 1, presented is diagram of an example system 100 that facilitates healthcare delivery using AI tactics in accordance with various aspects and embodiments described herein. Aspects of systems, apparatuses or processes explained in this disclosure can constitute machine-executable components embodied within machine(s), e.g., embodied in one or more computer readable mediums (or media) associated with one or more machines. Such components, when executed by the one or more machines, e.g., computer(s), computing device(s), virtual machine(s), etc. can cause the machine(s) to perform the operations described.

System 100 includes one or more dynamic healthcare delivery data sources 102, one or more healthcare information sources 112, historical healthcare delivery information 148, healthcare intelligence server 146, and a client device 150. Generally, the healthcare intelligence server 146, and the client device 150 can include memory that stores computer executable components and a processor that executes the computer executable components stored in the memory, examples of which can be found with reference to FIG. 18. For example, in the embodiment shown, the healthcare intelligence server 146 can include or be communicatively coupled to at least one memory 128 that stores computer executable components. These computer executable components can include for example, a reception component 126 and a live healthcare delivery guidance module 132. The healthcare intelligence server 146 can further include processor 130 to execute these computer executable components. The healthcare intelligence server 146 can also include a system bus 144 to communicatively couple the various components of the healthcare intelligence server 146 (e.g., the reception component 126, the live healthcare delivery guidance module 132, the memory 128, the processor 130).

The healthcare intelligence server 146 can be configured to provide various AI based tools for integrated healthcare organizations or environments to create actionable insight across the healthcare system and the care pathway, enabling better clinical and financial outcomes. In the embodiment shown, at least some of these tools can be provided by the live healthcare delivery guidance module 132. The components of the healthcare intelligence server 146 (e.g., reception component, the memory 128, the processor, the live healthcare delivery guidance module 132) can be provided at one or more dedicated computing devices (e.g., real or virtual machines). Entities can interface with the live healthcare delivery guidance module 132 using a suitable client device 150. The entities can include machines, devices, and systems, as well as human users. As used in this disclosure, the terms "user," "clinician", "healthcare professional," "patient" and the like refer to a person that can employ system 100 (or additional systems described in this disclosure) using a client device 150.

As used herein, the term "clinician" can refer to any individual or entity that is involved in the treatment and observation of living patients, as distinguished from one engaged in research. For example, a clinician can include but not limited to: a physician or doctor, a physicians' assistant, a nurse, a nurse practitioner, a midwife, a medical technician, and the like. Further in some embodiments, a machine (e.g., a robot, an IMD, medical equipment, medical devices, etc.) can be configured to perform a medical procedure or provide medical treatment. Thus, in some embodiments, the term "clinician" can also encompass a machine that can perform a medical procedure or provide medical treatment. The term "healthcare organization" is used herein to refer to any entity (e.g., including a company, a group of individuals, or a solo individual) that provides healthcare services to patients, whether it be at a designated healthcare facility, in an ambulatory vehicle, or out in the field. The terms healthcare facility or medical facility as used herein can refer to any physical location (e.g., building, building complex, campus, etc.) where healthcare is provided. Healthcare facilities can range from small clinics and doctor's offices to urgent care centers and large hospitals with elaborate emergency rooms and trauma centers. Various embodiments of the subject disclosure can be applied in association with managing and optimizing healthcare at a wide range of healthcare facilities, from large and complex hospitals that are equipped to perform a wide range of medical procedures to small town clinics. It should be appreciated that the disclosed techniques can be employed to facilitate provision of medical care to a patient in any scenario that involves a human (e.g., one or more clinicians, a non-clinician in emergency situations and even the patient himself/herself) providing the care. In addition, in some embodiments, a machine (e.g., and IMD, a robot, etc.) can be configured to perform medical procedures. Thus, in some embodiment, the disclosed techniques can further be applied to monitor and optimize provision of medical care by machines.

The client device 150 can include any suitable computing device configured to receive, process and/or render intelligence information provided by the healthcare intelligence server 146. In some implementations, the client device 150 can also be configured to provide feedback information to the healthcare intelligence server 146. For example, client device 150 can include a desktop computer, a laptop computer, a television, an Internet enabled television, a mobile phone, a smartphone, a tablet personal computer (PC), or a personal digital assistant (PDA), a heads-up display (HUD), an augmented reality (AR) device, a virtual reality (VR) device, a wearable device, an implanted medical device (IMD), and the like. In the embodiment shown, the client device 150 can include a rendering component 152 to provide for rending information to a user at the client device using as suitable output component. For example, the rendering component 152 can be or include a display, a speaker, a sensory or haptic feedback device, and the like. In some embodiments, described infra, the healthcare intelligence server 146 can facilitate generating a graphical user interface (GUI) that can be displayed at the client device 150 (e.g., via rendering component 152) that facilitates viewing and interacting with information and services provided by the healthcare intelligence server 146.

In one or more embodiments, the healthcare intelligence server 146 can provide various services to entities (via their respective client devices) via a suitable network accessible platform. For example, in some implementations, rendering component 152 can include an application (e.g., a web browser) for retrieving, presenting and traversing information resources on the Internet. According to this aspect, the healthcare intelligence server 146 can provide processed information and interactive tools to users via a website platform that can be accessed using a browser provided on their respective client devices (e.g., client device 150). In another implementation, the healthcare intelligence server 146 can provide processed information and interactive tools to users via a mobile application, a thin client application, a thick client application, a hybrid application, a web-application and the like. Still in other implementations, one or more components of the healthcare intelligence server 146 can be provided at the client device 150 and accessed directly in an offline mode.

The various components and devices of system 100 can be connected either directly or via one or more networks, (not shown). Such network(s) can include wired and wireless networks, including but not limited to, a cellular network, a wide area network (WAN, e.g., the Internet), a local area network (LAN), or a personal area network (PAN). For example, the healthcare intelligence server 146 can communicate with the client device 150, the one or more dynamic healthcare delivery data sources 102, the one or more healthcare information sources 112, and/or the historical healthcare delivery information 148, (and vice versa), using virtually any desired wired or wireless technology, including, for example, cellular, WAN, wireless fidelity (Wi-Fi), Wi-Max, WLAN, etc. In an aspect, one or more components of system 100 are configured to interact via disparate networks. It is to be appreciated that although various components of the healthcare intelligence server 146 are depicted as co-located on a same device, such implementation is not so limited. For example, one or more components of the healthcare intelligence server 146 can be located at another device or associated system, a client device 150 another server, and/or the cloud. Likewise, the one or more dynamic healthcare delivery data sources 102, the one or more healthcare information sources 112 and/or the historical healthcare delivery information 148 can be located locally at the healthcare intelligence server 146.

In the embodiment shown, the healthcare intelligence server 146 can include live healthcare delivery guidance module 132 to facilitate guiding clinicians in real-time in association with treating patients to deliver optimal patient care from both a clinical and financial perspective while reducing adverse outcomes and complications. In this regard, the live healthcare delivery guidance module 132 can be configured to evaluate a current clinical scenario in real-time by employing one or more machine learning algorithms that are configured to make inferences and determinations about the current clinical scenario in view of feedback 145 received about the current clinical scenario and information provided by one or more healthcare information sources 112 and/or the historical healthcare delivery information 148.

The healthcare information sources 112 can include internal systems and databases associated with one or more healthcare organizations, as well as systems and database that are openly accessible to public entities. The healthcare information sources 112 can include various systems and databases that provide relatively static information regarding defined operations of healthcare organization. For example, in the embodiment shown, the healthcare information sources 112 can provide information including but not limited to: SOP data 114, EMR/EHR data 116, medical literature 118, human resources (HR) data 120, finance data 122 and inventory data 124.

The SOP data 114 can include information defining workflows for various clinical procedures and scenarios. Most medical organizations have defined rules or regulations that provide guidelines regarding how to treat patients in association with specific patient conditions, procedures and/or circumstances. These rules or regulations are generally referred to as standard operating procedures (SOPs). For example, emergency room physicians have SOPs for patients who are brought in an unconscious state; nurses in an operating theater have SOPs for the forceps and swabs that they hand over to the operating surgeons; and laboratory technicians have SOPs for handling, testing, and subsequently discarding body fluids obtained from patients. Medical procedures can also be associated with SOPs that provide guidelines that define how to perform the procedure (e.g., steps to perform and how to perform them), how to respond to different patient conditions in association with performance of the procedure, how to respond to complications that arise, and other type of events that may arise over the course of the procedure, and the like. Some healthcare organizations can also establish or adopt SOPs for medical conditions that can define standard medical practices for treating patient's having the medical condition and the respective medical conditions. Some healthcare organizations can also have SOPs regarding providing healthcare to patients having two or more medical conditions (e.g., referred to as comorbidity). In this regard, the SOP data 114 can include information that identifies and/or defines one or more standardized or defined protocols for following in association with performance of a procedure, treating a patient with a condition, and/or responding to a clinical scenario. For example, with respect to a procedure, the workflow information can identify procedural steps or processes to be performed and when, timing of the steps, information regarding how each step/process should be performed, and the like.

In some implementations, the SOP data 114 can include information defining workflow SOPs for a healthcare organization or facility. In other implementations, the SOP data 114 can include collated information that defines different workflow SOPs employed by different healthcare organizations as well as different facilities or departments within a single healthcare organization. For example, there is a popular misconception that SOPs are standardized across the universe of practice. However, the very nature of an SOP is that it is not universally applied. For example, the workflow SOPs for treating patient in labor at a small rural clinic may be different than that employed by a large training hospital.

In some implementations, as discussed in greater detail infra, the live healthcare delivery guidance module can employ machine learning analysis of different SOPs for different environments and/or different healthcare organizations to facilitate determining appropriate aspects of the SOPs for applying to a clinical scenario based on the current context of the clinical scenario.

The EMR/EHR data 116 can include any known and recorded medical and/or health information about current and past patients of one or more healthcare organizations. In this regard, the EMR/EHR data 116 can include information traditionally found in patient EMR or EHRs including but not limited to: information identifying patients, information providing demographic profile information for respective patients, information regarding past medical history (e.g., including past diagnosis, procedures, conditions, etc.), vital signs, progress notes, medications, immunization dates, allergies, laboratory report data, imaging studies, pathology report data, care plan information, insurance information, and the like. The patient information can also include personal information associated with the patient, such as information regarding the patient's family and friends, preferences, birthday, hobbies, and the like.

The medical literature 118 can include can include various sources of electronic literature providing medical information, including textbook data used to train clinicians in various areas and specialties of healthcare delivery, information describing known medical conditions and diagnosis, information describing known medical procedures and complications, information describing pharmaceuticals, information describing medical instruments, supplies and devices, medical research data, and the like.

The HR data 120 can include information about clinicians employed by one or more healthcare facilities. This can include information identifying the respective clinicians, their roles (e.g., including authorization to perform various tasks), their responsibilities, their specialties, their employment/work history, salary information, scheduling information, preference information and the like. The HR data 120 can also include learned information about the respective clinicians over time regarding the professional capabilities and performance. For example, the HR data 120 for a physician can include information developed for the physician over time that identifies historical performance of the physician in association with performance of one or more procedures. This can include for example, the number of procedures performed, the outcomes of the procedures, the areas of the workflow for the procedures that the clinicians perform well, number of errors made, types of errors made, where errors tend to be made and the like. The historical performance information can also include information regarding performance of a clinician in association with treating different medical conditions. In this regard, the historical performance information can identify the level of expertise and proficiency of a clinician with respect to treating different types of conditions and performing different types of procedures. The HR data 120 can also include feedback provided by patients, colleagues and the like regarding a clinician's performance, including the level of quality and satisfaction the respective individuals associate with the clinician's performance. In some implementations, the HR data 120 can also include information regarding preferences regarding one or more other clinicians a clinician prefers to work with, one or more other clinicians the clinician does not work well with (e.g., associated with one or more negative outcomes in performance or patient satisfaction), and the like.

The finance data 122 can include any type of financial information pertaining to costs associated healthcare services. For example, the finance data 122 can include costs associated with different procedures and utilization of different resources, including human resources as well as medical instruments and supplies. In some implementations, the finance data 122 can include historical costs, such as historical costs associated with past procedures, courses of care and the like. For example, with respect to past procedures, the finance data 122 can identify total costs (e.g., to the healthcare organization) of each procedure performed, as well as line item costs associated with individual components of the procedures, including supplies/equipment costs, personnel costs, room/space costs, individual process or procedural steps, and the like. In some implementations, finance data 122 can also include information regarding reimbursement for respective procedures, including total reimbursement and reimbursement for procedural components. In some implementations, the finance data 122 can also include cost information attributed to LOS, procedure complications, and procedural and/or clinical errors (e.g., including cost attributed to litigation associated with the error).

The inventory data 124 can include information regarding medical supplies, instruments, equipment and the like that are used by a healthcare organization in association with performance of medical procedures. In this regard, the inventory information can identify all medical supplies, instruments, equipment that are in stock or otherwise in possession by the medical organization, their status (e.g., used/unused, current/expired, working/broken, etc.), what they are used for, where they are located and the like. The inventory data 124 can also include records of when respective medical supplies, instruments, equipment, etc. were ordered, what they were ordered for (e.g., a specific procedure, a specific clinician, a specific medical department, a specific operating room, etc.), and where the supplies came from. The inventory data 124 can also include same or similar information for supplies that are out of stock, ordered, and to be ordered.

It should be appreciated that various additional data sources can be employed to provide insight that can be used by the live healthcare delivery guidance module 132 to facilitate guiding clinicians in practice. For example, healthcare information sources 112 can include any potential information source or system that can provide and/or employ insight regarding any facet of operation and performance of the healthcare organization, from the patients and healthcare personnel to physical tools and structures associated with the integrated healthcare organization. In this regard, the types of data provided by the healthcare information sources 112 is not limited to those describe herein.

The historical healthcare delivery information 148 can include historical information recorded for past patients regarding any monitored parameters associated with their course of care. In one or more embodiments, this can include patient data 104, workflow data 106, clinician data 108 and/or facility data 110 associated with a past patient's course of care. For example, for respective past patients, the historical healthcare delivery information 148 can identify a condition or diagnosis of the patient, information identifying or describing the physiological state/condition of the patient at the time of arrival at the healthcare facility (or at the time when treatment was initiated), detailed parameters regarding what treatment was provided to the patient, including clinical actions that were taken in association with treatment and when, the clinical reactions or outcomes of the respective actions, what clinicians performed respective actions, states of the clinicians at the time of performance of the respective actions, physiological states of the patient associated with respective actions, contextual state of the healthcare facility over the course of care (e.g., adequately staffed or not, number of patients admitted, status of medical resources available, etc.), and the like. Additional description of the types of information that can be included in the patient data 104, workflow data 106, clinician data 108 and/or facility data 110, is described infra with respect to real-time processing of the live feedback information 154.

The healthcare intelligence server 146 can include reception component 126 to access and/or retrieve the historical healthcare delivery information 148 and information provided by the one or more healthcare information sources 112 (e.g., the SOP data 114, the EMR/EHR data 116, the medical literature 118, the HR data 120, the finance that 122 and the inventory data 124). The reception component 126 can also receive and/or retrieve the live feedback information 154 from one or more dynamic healthcare delivery data sources 102 regarding various dynamic aspects of healthcare delivery at a healthcare facility. The information provided by the dynamic healthcare delivery data sources 102 can be considered dynamic because at least some of the information can dynamically change over a course of patient care. For example, at least some of the information can change from second to second, minute to minute, over a course of an hour, over a course of a day, and the like. In the embodiment shown, the feedback can include but is not limited to: patient data 104, workflow data 106, clinician data 108 and facility data 110.

The patient data 104 can include real-time information related to a patient's current physiological state or condition. For example, in some implementations, the patient data 104 can include information received in association with initiation of treatment of a patient that provides an assessment of a condition or diagnosis of a patient for which medical care is being provided to the patient. The patient data 104 can further include any information gathered over the course of care relating to the physiological state or condition of the patient. For example, the patient data 104 can include information regarding tracked physiological parameters of a patient (e.g., vital signs and various other physiological parameters), timing associated with the tracked physiological parameters (e.g., onset, duration, etc.), changes in a physiological status or state of a patient, changes in appearance of the patient, physical range of motion or movements capable of being performed by the patient, expressed symptoms and side effects of the patient, expressed levels of pain experienced by the patient, information regarding a mental state of the patient, and the like. For example, for labor patients, there are key data and decision points that can affect the outcome of the baby including lifelong cognitive and physical functions. For instance, these key data points can include but are not limited to: timing of onset of labor, timing of decision to induce, timing of the active phase, timing of rupture of the membrane, timing and dosage of certain administered pharmaceuticals, changes in dilation, fetal heart rate, fetal deceleration, maternal temperature, maternal hypertension, timing of hypoxia onset, and the like. According to this example, for labor patients, the patient data 104 can include information corresponding to or related to these key data point. In some implementations, the patient data can also identify a current location of a patient relative to a healthcare facility (e.g., in an ambulance on the way to the emergency room, within a room of the healthcare facility, etc.). In some embodiments, the specific physiological parameters that are tracked can be predefined based on a condition or the patient or course of care for the patient. For example, the physiological data that is relevant to a patient undergoing a course of labor can be different to those of a patient receiving a heart transplant. Accordingly, the specific patient data that is collected and reported in real-time can be tailored to the specific context of a patient's condition and treatment.

The types of dynamic healthcare delivery data sources 102 from which the patient data 104 is received can vary. In some implementations, the patient data 104 can be received directly from one or more medical monitoring devices associated with the patient (e.g., mother and infant(s) in for labor patients) and configured to read and report monitored physiological parameters. For example, the medical monitoring devices can include a device worn by, within (e.g., an IMD), and/or physically connected to the patient and configured to capture and/or monitor physiological information (e.g., physiological parameters) that can be sent to or otherwise received by the healthcare intelligence server 146 in real-time or substantially real-time. For example, these physiological parameters can include but are not limited to information regarding: heart rate, blood pressure, SpO2, respiratory rate, temperature, hypertension, hydration level, glucose level, cortisol level, potassium level, etc. In another example, the one or more dynamic healthcare delivery data sources 102 can include medical monitoring devices configured to detect presence of various bacteria, viruses, pathogens, and the like. In another example, the one or more dynamic healthcare delivery data sources 102 can include medical monitoring devices configured to detect presence and/or levels of various biomarkers and/or known substances produced by the body. Other potential information that can be detected by medical monitoring devices can include but is not limited information regarding a patient's folic acid, calcium, magnesium, creatine kinase, vitamin B12, vitamin D, ferritin, total cholesterol, hemoglobin, HDL, LDL, triglycerides, fatty acids, insulin, hemoglobin, hormones (e.g. thyroid hormones (thyroid-stimulating hormone (TSH), metabolic hormones, reproductive hormones, etc.), liver enzymes, electrolytes (e.g. sodium, potassium, chloride, etc.), platelets, white blood cells, red blood cells, iron, etc.

For example, in some embodiments, the one or more dynamic healthcare delivery data sources 102 can include blood-sampling sensors (e.g. as glucose meters), tissue-embedded sensors (e.g. pacemakers and defibrillators), ingestibles embedded in pills that dissolve, epidermal sensors (e.g. patches and digital tattoos), wearables embedded in clothing or accessories, and external sensors (e.g. blood-pressure cuffs and pulse oximeters). In another example, the one or more dynamic healthcare delivery data sources 102 can include biosensing contact lenses configured to be worn in the patient's eye and sense/detect various biomarkers in tear fluid. The contact lens can further be configured to wirelessly transmit information regarding presence and/or concentration of the detected biomarkers either directly or indirectly (e.g., via an intermediary device) to the healthcare intelligence server 146. In another example, the one or more dynamic healthcare delivery data sources 102 can include an implantable cardioverter-defibrillator (ICD) that is implanted within the patient and configured to perform conventional functions of an ICD as well as additional sensing of biomarkers in bodily fluids. In yet another example, the one or more dynamic healthcare delivery data sources 102 can include a urinary catheter configured to be worn by the user to facilitate urinary functions while also being configured to detect biomarkers in urine. In another example, the one or more dynamic healthcare delivery data sources 102 can include a device configured to determine physiological information about the user based on detection of one or more biomarkers included in sweat generated by the patient. In yet another example, the one or more dynamic healthcare delivery data sources 102 can include a blood-testing device that is implanted into the body (e.g. under the skin) or worn in the form of a patch and configured to detect biochemical information regarding at least one of: glucose levels, cortisol levels, potassium levels, blood oxygen levels, blood alcohol levels, inflammation, nitric oxide levels, drug levels/residues present in the body, pathogens present in the body, or bacteria present in the body, folic acid levels, calcium levels, magnesium levels, creatine kinase levels, vitamin B12 levels, vitamin D levels, ferritin levels, total cholesterol levels, hemoglobin, HDL, LDL, triglycerides, fatty acids, insulin, hormones (e.g. thyroid hormones (thyroid-stimulating hormone (TSH), metabolic hormones, reproductive hormones, etc.), liver enzymes, electrolytes (e.g. sodium, potassium, chloride, etc.), platelets, white blood cells, red blood cells, iron, etc.

In another example, the one or more dynamic healthcare delivery data sources 102 can include a device that is configured to detect and determine physiological information regarding electrical activity of the brain (also referred to as neurofeedback) and provide this information to the healthcare intelligence server 146. According to this example, the one or more dynamic healthcare delivery data sources 102 can include a near-infrared spectroscopy (NIRS) spectroscopy sensor configured to determine hemodynamic information such as working memory performance levels, stress levels and attention levels of the patient. The neurofeedback can also include brain activity information determined by an electroencephalogram (EEG) sensor worn by the patient. For example, EEG measurements can include voltage fluctuations in the time and/or frequency domain that can be correlated to mental performance with respect to various defined cognitive function areas, including but not limited to: attention, familiarity, mental effort, working memory, linguistic acquisition, social learning, and medication.

It should be appreciated that the above described medical monitoring devices (and the associated types of physiological information capable of being detected/determined by these devices), are merely exemplary and that other existing and future implantable/wearable devices capable of detecting additional types of physiological information can be employed.

In other implementations, the patient data 104 can include information observed by or determined by a clinician and entered into an electronic tracking system that records and reports observed changes in physiological states of a patient. For example, the electronic tracking system can receive information observed and/or determined by a first responder, paramedic, nurse, physician, etc., regarding the physiological state or condition of the patient over the course of care. With these implementations, the reception component 126 can receive the patient data 104 from the electronic tracking system as it is entered into or otherwise received by the electronic tracking system. The manner in which the patient data 104 is input to the electronic tracking system can vary. For example, in some implementations, the electronic tracking system can receive data entry via a client device 150 as text, a voice to text input, in natural language, and the like. In another example, the patient data 104 can be received from an electronic symptom tracking system that receives information entered by the patient (or an authorized agent of the patient) regarding self-reported medical symptoms or other information about how the patient is feeling mentally and/or physically (e.g., level of pain experienced, level of energy, stress level, mood information, etc.).

The workflow data 106 can include real-time information regarding the clinical workflow followed for a patient over the course of care, including clinical events that occur over the course of care. In this regard, the workflow data 106 can identify and describe medical treatment provided to a patient by one or more clinicians over the course of care. This can include but is not limited to: procedures performed, specific steps of the procedures performed, relevant aspects/parameters associated with respective steps, timing and order of the steps, medical instruments/supplies used, clinicians involved in performance of procedural steps, roles and actions performed by the respective clinicians, medications administered, dosage of the medications administered, timing of patient check-ups, and the like. Like patient data, the specific workflow events that are tracked and reported in-real time can vary based on the clinical context of each patient. For example, with respect to a patient in labor, the workflow data 106 can include information regarding treatment provided by clinicians to the patient over the course of labor (e.g., administering of drugs, surgical procedural steps, etc.), including information identifying the clinicians and the specific actions they performed and clinical decisions made (e.g., decision to induce). In another example, with respect to a surgical procedure, the workflow information can include specific parameters related to the physical actions performed by the surgeon. For instance, the workflow information can identify the location of incision, the size of the incision, the physical relation of a medical instrument to an anatomical part of the patients' body (e.g., captured via one or more sensors associated with the medical instrument, such as a camera, a pressure sensor, etc.), and the like.

The types of dynamic healthcare delivery data sources 102 from which the workflow data 106 is received can vary. In some embodiments, at least some of the workflow data can be received from an electronic tracking system configured to receive user input recording workflow events over a course of patient care. For example, the user input can be provided by one or more clinicians involved with treating the patient or monitoring the treatment of the patient. In another embodiment, at least some workflow data 106 regarding actions performed by clinicians, locations of clinicians and the like, can be received from one or more motion or movement sensors worn by clinicians. In another embodiment, at least some of the workflow data 106 can be received from an image data monitoring system configured to capture and/or receive live video at a healthcare facility. For example, the live video can be received from cameras worn clinicians, patient, and other entities at the healthcare facility. In another example, the live video can be received from one or more stationary cameras located at various locations throughout the facility. According to this embodiment, the image data monitoring system can be configured to employ live video processing techniques to automatically identify objects, people, and other things included in the image data. The video processing techniques can also be configured to determine actions performed by clinicians, patients and the like, based on the image data. In another embodiment, at least some of workflow data 106 can be received from an audio monitoring system configured to receive and evaluate audio, including speech, in real-time. For example, the audio monitoring system can determine words spoken, actions, performed and the like, based on analysis of the audio.

The clinician data 108 can include real-time information associated with respective clinicians that can influence their ability to provide quality patient care. In this regard, the clinician data 108 can identify the current clinicians that are available for performing patient care (e.g., clinicians that are on the clock, clinicians that are on-call), current locations of respective clinicians, and current activities being performed by clinicians (e.g., administering anesthesia to patient John Doe in operating room 303), and the like. The clinician data 108 can also track the current workload of a clinician, including the number of patients being treated and scheduled to be seen, type of extent of treatment required by the clinician for each patient, and the like. The clinician data 108 can also include information regarding the current physiological and mental status of clinicians (e.g., fatigue, stress levels, etc.).

The types of dynamic healthcare delivery data sources 102 from which the clinician data 108 is received can vary. In some embodiments, at least some of the clinician data 108 can be received from one or more devises worn by or otherwise physically coupled to the clinicians. For example, clinician data 108 including information regarding the physiological and/or mental states of the clinicians can be received from various types of biofeedback sensors worn by the clinicians. In another example, information regarding current locations of clinicians can also be tracked by devices worn by or coupled to the clinicians. The locations of clinicians can also be determined using various other automated object location tracking techniques. In another example, information regarding current workloads of clinicians (e.g., including number of patients being treated, type of treatment required, etc.) can be received from scheduling systems, patient tracking systems, and the like.

The facility data 110 can include dynamic contextual data regarding a current context or state of a healthcare facility. This can include contextual information that can change over the course of a minute, an hour, a day, and the like. For example, the facility data 110 can include real-time information regarding the status and availability of resources provided by the facility, including rooms, medical equipment and medical supplies. The facility data 110 can also include real-time activity information that tracks the events and activities occurring throughout the healthcare facility in real-time (e.g., what clinical and non-clinical actions are being performed at respective locations of the healthcare facility). The types of dynamic healthcare delivery data sources 102 from which the facility data 110 is received can vary. For example, the facility data can be received from automated video monitoring systems, inventory monitoring systems, and the like.

In the embodiment shown, the live healthcare delivery guidance module 132 can include monitoring component 134, AI evaluation component 136, and AI response component 142. The monitoring component 134 can be configured to regularly and/or continuously monitor the live feedback information 154 provided by the one or more dynamic healthcare delivery data sources 102 for processing by the AI evaluation component 136 and the AI response component 142 in real-time. In this regard, the processing can be considered real-time because the AI evaluation component 136 and the AI response component 142 can respectively be configured to generate an output based on the received live feedback information 154 substantially coinciding with the time that the live feedback information 154 is received. For example, the processing time between reception of the live feedback information 154 and generation of a response (e.g., a notification) to the live feedback information 154 can be between about 1.0 second and 60 seconds.

In some embodiments, the monitoring component 134 can be configured to monitor all information received by the reception component 126. In another embodiment, the monitoring component 134 can be configured to monitor subsets of the live feedback information 154 that are relevant to a course of care, medical procedure, clinical scenario, patient, and the like. For example, as described above, there are key data and decision points that can affect the outcome of the baby including lifelong cognitive and physical functions. Thus in some embodiments, for labor patients, the monitoring component 134 can be configured to selectively monitor information regarding these defined key data points (e.g., timing of onset of labor, timing of decision to induce, timing of the active phase, timing of rupture of the membrane, timing and dosage of certain administered pharmaceuticals, changes in dilation, fetal heart rate, fetal deceleration, maternal temperature, maternal hypertension, timing of hypoxia onset, and the like). Further, in some implementations of this embodiment, the specific subset of information (e.g., parameters) that the monitoring component 134 monitors for a patient, diagnosis, course of care, procedure, etc., can be predefined. In other implementations, the monitoring component 134 can determine or infer the parameters to monitor that are relevant to a current clinical scenario, course of care, patient, etc., based on evaluation of the live feedback information 154, the information provided by the one or more healthcare information sources 112, and/or the historical healthcare delivery information 148 using one or more machine learning techniques.

The AI evaluation component 136 can be configured to evaluate the monitored, live feedback information 154 in real-time to facilitate guiding clinicians in association with provision of medical care while preventing or reducing the occurrence of adverse outcomes. For example, the AI evaluation component 136 can evaluate a current clinical scenario to identify issues, and generate clinical observations about the scenario to facilitate making more intelligent and informed clinical decisions. In one or more embodiments, the AI evaluation component can include significant event/condition identification component 138 and risk/severity component 140.

The significant event/condition identification component 138 can be configured to evaluate the monitored feedback information to identify significant events or conditions reflected in the live feedback information 154. In this regard, a significant event or condition can include substantially any event or condition reflected in the patient data 104, workflow data 106, clinician data 108 and/or facility data 110, that warrants attention and/or a response. A significant event or condition can be related to a single patient, a group of patients, a single clinician, a group of clinicians, an area of a healthcare facility, an entire healthcare facility, and the like. In general, a significant condition can correspond to a state or status of a patient, group of patients, a clinician, a group of clinicians, an area of a healthcare facility, and/or of an entire healthcare facility, that warrants attention and/or a response. A significant event can correspond to the occurrence of something that happens over a course of care of a patient or at a healthcare facility in general that warrants attention and/or a response. In some implementations, a significant event can involve the development or change in a condition. For example, a change in a condition of a patient can correspond to a significant event.

For example, with respect to laboring patients, significant events or conditions can include the key data and decision points noted above. Similarly, key data and decision points associated with treatment of a medical condition, performance of a surgical procedure and the like can also be considered significant events or conditions. In another example, a significant event or condition can include detection of a physiological parameter, parameter value, and/or combination of different physiological parameters/parameter values monitored for a patient (e.g., the mother and/or the infant in labor scenarios), that warrants further monitoring and/or requires a clinical response (e.g., performance of a medical procedure, change in dosage and/or provision of a pharmaceutical). According to this example, significant events/conditions can include the detection of a particular physiological parameter alone (e.g., detection of a pathogen present in the body), a change in a specific physiological parameter (e.g., decrease in blood pressure), detection of a value of a particular physiological parameter being above or below a set threshold and/or above or below the threshold for a defined duration of time (e.g., decrease in blood pressure below normal level for more than 1.0 minute), and the like. In another example related to patient data 104, a significant event or condition can include one or more physiological parameters and/or parameter values that correspond to a medical complication, or a defined physiological state the patient is experiencing (e.g., a parameter or combination of physiological parameters that reflect the patient has entered stage II of labor).

In another example, a significant event can include an error in the provision of medical treatment. In this regard, patient data 104, workflow data 106, clinician data 108 and/or facility data 110 that indicates an error in treatment has occurred can be considered a significant event. For example, an error in treatment can be based on improper performance of a SOP required for a current clinical scenario associated with a patient, failure to perform an aspect of an SOP required for a current clinical scenario, improper performance of a procedure or procedural step, and/or performance of unnecessary medical treatment (e.g., treatment not directed by a relevant SOP). With respect to clinician data 108 significant events or conditions can include a clinician demonstrating a level of fatigue or attentiveness that is below a level required for provision of quality care. In another example, feedback information that indicates a clinician is performing or about to provide medical treatment that the clinician is not authorized to perform or that the clinician has demonstrated low proficiency in performing correctly can be considered a significant event. In another example, a significant event can include an improper number and/or distribution of clinicians involved in a patient's care. For instance, a procedure may require the presence of an assisting nurse. With this example, live feedback information 154 that indicates the assisting nurse is absent can be considered a significant event. Further, a significant event or condition associated with a medical facility or area of a medical facility can involve an inadequate patient to clinician ratio, inadequate resources or distribution of resources for the needs of the current patient population, malfunction of a medical instrument that influences the ability to provide quality care to one or more current patients, and the like.

It should be appreciated that the significant events and conditions described above are merely exemplary and many additional type of events and conditions associated with healthcare delivery can be considered significant in the sense that the event or condition warrants performance of a response and/or that recognition of the occurrence of the event or condition is relevant to the clinical decision process for a current clinical scenario. Further, it should be appreciated that clinically significant events or conditions can involve a combination of different parameters associated with the patient data 104, the workflow data 106, the clinician data 108, and/or the facility data.

In some embodiments, one or more significant events or conditions can be predefined. In accordance with these embodiments, information defining parameters, parameter values and/or different parameter/value combinations that correspond to a significant event or condition can be stored in memory (e.g., memory 128) accessible to the significant event/condition identification component 138 and employed to automatically detect and characterize the occurrence of a significant event or condition based on the monitored live feedback information 154.

For example, using SOPs provided in the SOP data as an initial framework, the significant event/condition identification component 138 can be configured to characterize a violation to an SOP as a significant event or condition. In this regard, parameters in the live feedback information 154 that indicate an SOP applicable to a current clinical scenario has been violated (e.g., because a required workflow event was skipped, performed incorrectly, performed by an unauthorized clinician, because an additional or unnecessary event was performed, and the like) can be characterized as a significant event or condition. Various other significant events or conditions involving defined parameters, parameter values and/or combinations of parameters/values represented in the patient data 104, the workflow data 106, the clinician data 108 and/or the facility data 110 can also be predetermined to correspond to a significant event or condition. For example, with respect to laboring patients, the various key data points/decision points discussed above can be considered clinically significant event/conditions. In accordance with this example, based on the monitored feedback information, the significant event/condition identification component 138 can be configured to identify significant events/conditions including the onset of labor, the administration of a drug, the entrance into a phase of labor, a change in the dilation of the cervix, and the like. In another example, the drop in a clinician's attentiveness level below a certain threshold can be pre-defined as a significant event or condition. In another example, the lack of sufficient resources available to perform a clinical procedure can be predefined as a significant event or condition.

However, whether something associated with a patient, group of patients, clinician, group of clinicians, and/or medical facility as whole constitutes a significant event or condition in the medical context can be based on many context specific factors. For example, although there may be one or more SOPs defined for treating a patient in association with a procedure, course of care, or clinical scenario, these SOPs merely provide a guideline for treatment. In this regard, every possible clinical decision related to every clinical scenario cannot possibly be predetermined given the variability of parameters related to individual patients including their individual health histories and pathologies, the variability in factors related to the availability and capabilities of clinicians to treat the patients, the variability in factors related to the resources available at the healthcare facility for the treatment of the patients, and the like. In this regard, SOPs merely serve as one element that clinicians should consider when making clinical decisions. Every patient is different and the context of treatment for each patient varies. Thus, there are many other variables for a clinician to consider when evaluating a clinical scenario and determining an appropriate clinical response to perform for a patient. For example, clinical decision regarding how to care for a patient and/or whether and how to respond to a current condition of the patient can vary drastically, based on the medical history or of the patient, medications taken, allergies, a comorbidity status of the patient, complications associated with the patient, medical insurance held by the patient, preferences of the patient, and the like. In addition to variability in patient specific parameters, variability associated with the capabilities and status of available clinicians, the urgency of a clinical scenario, the resources available at the healthcare facility, and the like, can also impact clinical decisions. In this regard, something that could be considered a significant event or condition in one clinically context may not be a significant event or condition in another, and vice versa.

In view of the many variables that are involved in clinical decision making, it is evident that even the most skilled and educated clinician cannot possibly become aware of and consider every possible variable for every patient under every context. In accordance with various embodiments, the significant event/condition identification component 138 can employ AI to facilitate determining more accurate and comprehensive clinical reasoning based on live feedback information 154 by providing evidence based consideration of the many different factors impacting a current clinical scenario as learned from analysis of the collated, historical healthcare delivery information 148 in view of the information provided by the one or more healthcare information sources 112. Using one or more machine learning techniques, the significant event/condition identification component 138 can evaluate the historical healthcare delivery information 148 and/or the information provided by the one or more healthcare information sources 112 to learn specific patterns in the data that correspond to events or conditions that warrant attention and/or a response in order to facilitate prevention and/or reduction in adverse outcomes in different clinical context. Thus, the significant event/condition identification component 138 can employ AI to evaluate the many different factors having an impact on the outcome of a current clinical scenario to identify and characterize significant events or conditions as specifically tailored to a patient, clinician, set of clinicians, healthcare environment and the like. The significant event/condition identification component 138 can further facilitate identifying significant events and conditions in situations that these significant events or conditions might be overlooked or are incapable of being accurately and consistently detected due to various limitations associated with a clinical environment. The significant event/condition identification component 138 can further characterize the parameters and/or the parameter values that correspond to an identified significant event or condition in a context that can vary based on the historical health history and pathology of the patient, the capabilities of the available clinicians, the resources available at the healthcare facility, and the like. The significant event/condition identification component 138 can further detect these parameters corresponding to a significant event or condition in the live feedback information 154 to automatically identify and characterize a significant event or condition in real-time over the course of patient care.

Accordingly, in one or more embodiments, the significant event/condition identification component 138 can employ the historical healthcare delivery information 148 and/or the information provided in the one or more healthcare information sources 112 to learn what events or conditions should be considered significant (e.g., meaning they trigger acknowledgment and/or a response by a clinician to facilitate reducing or preventing adverse outcomes) based on the context of a current clinical scenario. In this regard, the significant event/condition identification component 138 can employ one or more machine learning techniques to evaluate the data to uncover correlations between the many contributing factors to identify significant events/conditions associated with a particular clinical scenario, including contextual factors related to the relevant SOPs, individual patients, clinicians involved, resources involved, state of the facility and the like.

In some implementations, the machine learning techniques can begin by looking for issues, complications, or areas attributed to financial and/or clinical loss in the available data. The significant event/condition identification component 138 can further correlate these errors to specific events and conditions. For example, in one or more embodiments, the significant event/condition identification component 138 can evaluate the historical healthcare delivery information 148 and the information provided by the one or more healthcare information sources to identify events or conditions that are attributed to these adverse clinical and/or financial outcomes in different clinical contexts. Using one or more machine learning techniques, the significant event/condition identification component 138 can compare historical information for same or similar courses of care, procedures, clinical scenarios and the like in view of the relevant SOP data 114, the EMR/EHR data 116, the medical literature 118, the HR data 120, the finance data 122 and the inventory data 124 to learn correlations between events or conditions associated with SOPs, patient pathology, physiological states, medical histories, medical resources used, clinician capabilities, different workflows followed for procedures, different clinical actions performed in response to medical complications, drugs administered, and the like, that have a direct or indirect effect on adverse clinical and financial outcomes. For example, the significant event/condition identification component 138 can identify correlations between parameters associated with changes in a patient's condition and the clinical workflow events performed over the course of care that result in adverse outcomes. The AI system can also identify correlations between human based factors and adverse clinical/financial outcomes. In this regard, the human based factors can relate to the individual performance of clinicians involved in patient care, the abilities of clinicians, the workload of the clinicians, the number of clinicians associated with an outcome, the fatigue levels of clinicians, and the like. For example, in one implementation, the significant event/condition identification component 138 can infer that an event involving a clinician performing or initiating performance (e.g., based on the live feedback information 154) of a procedure or procedural step is significant because the clinician has demonstrated a tendency to perform the procedure or procedural step incorrectly (e.g., based on historical performance information included in the HR data 120).

In other embodiments, using machine learning, the significant event/condition identification component 138 can examine the historical data and the information provided by the one or more healthcare information sources 112 to identify events or conditions associated with patient physiological parameters, patient pathologies, patients conditions, SOPs, workflows followed, treatment provided, identities of number of clinicians involved, number of clinicians involved, capabilities of the clinicians involved, resources used, and the like that caused a clinician to perform a response, which if not performed, results in an adverse clinical or financial outcome. These event or conditions can be considered significant. Still in other embodiments, using machine learning, the significant event/condition identification component 138 can evaluate the available data to uncover key data and decision points associated with a clinical scenario, course of care, procedure, SOP and the like, in view of different contextual factors associated with a patient's diagnosis, condition, medical history, clinicians involved, capabilities of the clinicians, resources involved, and the like.

In some embodiments in which the SOP data 114 comprise SOPs for same or similar procedures developed and applied by one or more disparate medical organizations, the significant event/condition identification component 138 can employ machine learning to converge on optimized SOPs for different scenarios. For example, based on analysis of different SOPs applied by different institutions for a same or similar clinical scenario, the significant event/condition identification component 138 learn what aspects of certain SOPs apply in different contexts and learn new ways for reducing adverse outcomes. In this regard, the significant event/condition identification component 138 can uncover new significant events or conditions that should be considered significant (or not) based on alternative protocols that involve acknowledging an event or condition or responding to another event or condition in a specific that results in reduction of adverse outcomes in different clinical contexts.

In association with identifying significant events or conditions, in some implementations, the significant event/condition identification component 138 can characterize and event or condition with a defined medical term or name/characterization that is used to refer to the type of event or condition in the medical field (e.g., generally by all medical practitioners or internally by a medical organization). For example, a condition expressed by a patient can be identified by a defined medical term for the condition (e.g., a diagnosis, a phase of labor, a medical term for a state of the patient etc.). In another example, an event can be characterized with a defined nomenclature for the event (e.g., onset of labor). In one or more embodiments, the significant event/condition identification component 138 can learn what certain event or conditions are referred to as based on information defining the event or condition included in the SOP data 114, the medical literature 118, and/or the historical healthcare delivery information 148.

In some embodiments, the AI evaluation component 136 can employ the risk/severity component 140 to facilitate determining whether an observed event or condition should be considered significant. With these embodiments, using the information provided by the one or more healthcare information sources 112 and the historical healthcare delivery information 148, the risk/severity component 140 can employ one or more machine learning techniques to determine or infer a level or risk or severity associated with failure to acknowledge and/or respond to a particular event or condition in association with the context of specific clinical scenario (e.g., impacted by factors related to the individual patients involved, the clinicals available, the capabilities of the clinicians, the resources available, and the like). The level of risk/severity can reflect a probability that one or more complications or adverse reactions will arise based on failure to acknowledge and/or respond to the event or condition, as well as a degree of severity of the one or more corresponding complication or adverse reaction. For example, if a patient expresses blood pressure higher than the normal level, if this is an initial observation, failure to call attention to it could be associated with a low risk because there is low probability of an associated complication. However, if the patient has expressed high blood pressure for several consecutive measurements, this could be attributed to a higher probability of a more significant complication. Thus, in this example, an initial spike in blood pressure may be considered an insignificant event that does not warrant attention because it is associated with low risk, while the occurrence of consistently high blood pressure after a X number of consecutive readings could be considered significant as it is associated with a higher risk, especially if the patient as other comorbidities that places the patient at higher risk for heart disease.

In some implementations, the degree of severity can reflect solely a level of clinical severity associated with the complication or adverse reaction, meaning a degree to which the complication or adverse reaction will impact the overall quality of life. In some scenarios, multiple complications and adverse reactions could be involved. The level of clinical severity can be based on the type of complication or adverse reaction as well as the medical history of the patient, the demographic of the patient (e.g., age, gender), preferences of the patient and the like. With these scenarios, the number of complications and adverse reactions can also affect the degree of severity. In other embodiments, the degree of severity can also reflect a financial component. In this regard, the risk/severity component 140 can also be configured to determine whether an event or condition is considered significant based on a probability that an adverse reaction or complication may occur if attention to the event/condition is not made and/or a response to the event/condition is not provided and a degree of clinical severity, as well as a cost attributed to the adverse reaction or complication. In this regard, the higher the cost, the higher the level of risk/severity. For example, in some embodiments the cost can be based on a cost to the healthcare provider or healthcare organization for failure to address the significant event or condition. According to this example, the risk/severity component 140 can evaluate the finance data 122 as well as the historical healthcare delivery information to determine a predicted level of cost associated with the potential complication or adverse reaction that the healthcare provider would be responsible for. This cost component can include for example, costs associated with correction of the error in terms of resource utilization (e.g., medical instruments and tools as well as human resources), costs associated with length of stay (LOS), costs associated with potential liability and litigation, and the like.

Costs associated with resource utilization and waste can also play a role when determining whether an event or condition should be considered significant. For example, a clinical event or condition could be failure to provide a clinician with an assistant during a procedure. The cost component associated with this event could be attributed to an increased cost associated with an increased probability of error by the clinician without the assistant (e.g., as determined based on historical performance information for the clinician in the HR data 120), an increased probability that the clinician will drop tools and waste resources (e.g., as determined based on historical performance information for the clinician in the HR data 120), and the fact the clinician will be required to be paid at a higher rate when working without the assistant (e.g., as determined based on the finance data 122 describing a payment schedule for the clinician). Thus, depending in part on the cost attributed to the failure to provide the clinician with an assistant, the event could be considered significant.

In some embodiments, the risk/severity component 140 can be configured to determine and associate a risk/severity score with an identified event or condition. According to these embodiments, the significant event/condition identification component 138 can be configured to determine whether to classify the event or condition as significant based on its associated risk/severity score. For example, the significant event/condition identification component 138 can be configured to determine that events or conditions associated with a risk/severity score above a threshold value can be considered significant. In other embodiments, the risk/severity component 140 can classify different events or conditions based on their risk/severity score. For example, the risk/severity component 140 can be configured to classify events or conditions as low risk, medium risk, or high risk, based on their risk/severity score. It should be appreciated that other classification schemes including two or more categories of risk/severity can be employed. In other embodiments, the significant event/condition identification component 138 can also distinguish between events and conditions that warrant attention or acknowledgment by a clinician (e.g., for further monitoring or otherwise considering in association with clinical decision making) verses events and conditions that warrant an actual clinical response by a clinician (e.g., performance of a procedure, administration of a drug, etc.).

The AI response component 142 can be configured to determine or infer and provide one or more responses to significant events or conditions based on identification of the significant events or conditions by the significant event/condition identification component 138. For example, in one or more embodiments, an appropriate response to an identified significant event or condition can include but is not limited to: tracking a parameter associated with the clinically significant event or condition via a GUI, determining a new parameter for tracking that is related to the significant event or condition and automatically beginning tracking of the new parameter via a GUI, notifying a clinician regarding the significant event or condition, requiring a clinician to respond to and/or acknowledge the notification, determining a recommended action in response to the significant event or condition for performance by one or more clinicians, determining and recommending a specific clinician that is most adapt or appropriate to perform the recommended response, and the like.

In various embodiments, a response determined by the AI response component 142 can be manifested at one or more client devices (e.g., client device 150). For example, as discussed in greater detail infra with reference to FIGS. 5-11, in some embodiments, the AI response component 142 can provide a tracking tool that can be configured to generate a GUI that includes a visual representation of tracked conditions and events for a patient over the course of care. The GUI can be rendered at a client device 150 via a display and can facilitate providing a visual representation of significant events and conditions related to a patient of the course of care. The visual representation can further be updated in real-time to reflect new tracked events and conditions that arise. With these embodiments, the AI response component 142 can respond to an identified significant event or condition by visually tracking the event or condition using the tracking tool. Further, in implementations in which the AI response component 142 determines or infers new relevant parameters for tracking, the AI response component 142 can facilitate automatically tracking the new parameter and providing a corresponding visual representation of the new tracked parameter in the GUI. In other implementations in which a response to an identified significant event or condition includes generation of a notification regarding the significant event or condition, the notification can be rendered to a user via the client device 150 (e.g., as a visual notification, as an audible notification, a sensory notification, or the like). Similar, responses including recommended actions and/or other related information associated with providing a recommended response to an identified significant event or condition can also be sent to and/or rendered at a client device 150 (e.g., via the rendering component 152). In some embodiments, in association with tracking, rendering or otherwise providing information regarding an identified significant condition or event, the AI response component 142 can describe the event or condition by its medical name or nomenclature (e.g., as determined by the significant event/condition identification component 138).

Some of the types of responses generated by the AI response component 142 discussed herein include rendering data (e.g., a GUI, a notification, etc.) in a visual format at the client device 150 via a display. It should be appreciated that the size, shape format and appearance of the visual data can be adapted based on the display capabilities of the client device 150. For example, as discussed above, the client device 150 can include a wide variety of mobile, stationary and wearable devices. These different types of devices above often have different capabilities and limitations (e.g., screen size, decoders . . . ). In an aspect, the rendering component 152 can provide presentation options in accordance with different device capabilities or limitations. For example, data rendering capabilities may be more limited in a mobile device (e.g., a smart-phone, a HUD device, etc.,) than in a fixed computing device (e.g., a desktop computer). In addition, because displays of various mobile devices are often smaller than displays in fixed computing devices, it may be possible only to display a relatively small amount of information at any given time on a mobile device. Accordingly, the size, appearance and features of visual data provided by the AI response component 142 (e.g., the patient tracking interface, a notification, etc.) can be adapted to optimize the display of options and content based on respective client device capabilities (e.g., based on screen size, screen resolution, input capabilities of the devices, processing capabilities etc.).

Further, in some implementations, a response can include a recommended action for performance by a machine, such as an IMD, a medical instrument, a medical device and the like, that can be configured to perform automated actions in response to control commands (e.g., dispensing medication, applying a medical treatment, moving a blade or needle relative to a body of a patient, etc.). With these implementations, the AI response component 142 can be configured to provide the corresponding control commands to such machines for execution thereby.

In some embodiments, the response generated by the AI response component 142 for a significant event or condition can be predefined. For example, in one implementation, the AI response component 142 can be configured to provide predetermined responses for specific types of events or conditions. For instance, the AI response component 142 can be configured to simply update a GUI to reflect significant conditions regarding changes in a physiological parameter expressed by a patient. On the other hand, the AI response component 142 can be configured to generate a notification regarding a significant event or condition that corresponds to onset of a medical complication. In another implementation, the AI response component 142 can be configured to determine and provide one or more predefined responses to identified significant events or conditions based their risk/severity score. For example, the AI response component 142 can be configured to merely visually track (over a timeline) the occurrence of events or conditions that are low risk (e.g., based on their risk/severity score relative to a threshold score). On the other hand, the AI response component 142 can be configured to generate and provide a notification for an event or condition that is considered high risk. Further, the entity to which the AI response component 142 provides the notification can be based in part on the type of event or condition, the level of risk/severity, and a role of an entity responsible for monitoring and/or responding to the event or condition. For example, the AI response component 142 can be configured to notify a nurse of a low risk condition and notify the attending physician if the condition is high risk.

In other embodiments, The AI response component 142 can further employ one or more machine learning techniques to determine appropriate responses to an identified significant event or condition based on historically appropriate responses for same or similar events or conditions determined based on analysis of the historical healthcare delivery information 148 and/or the information provided in the one or more healthcare information sources 112. In this regard, the AI response component 142 can employ one or more machine learning techniques to determine or infer one or more appropriate responses to an identified significant event or condition selected from a defined group of possible responses. For example, these possible responses can include but are not limited to: tracking a parameter associated with the clinically significant event or condition via a GUI, determining a new parameter for tracking that is related to the significant event or condition and automatically beginning tracking of the new parameter via the GUI, notifying a clinician regarding the significant event or condition, requiring a clinician to respond to and/or acknowledge the notification, determining a recommended action in response to the significant event or condition for performance by one or more clinicians, and determining and recommending a specific clinician that is most adapt to perform the recommended response.

Further, in embodiments in which an appropriate response includes a recommended action for performance by one or more clinicians (e.g., including a medical device, IMD, medical instrument, etc.), the AI response component 142 can further learn and infer appropriate clinical actions for responding to an identified clinically significant event or condition using machine learning analysis of the information provided by the one or more healthcare information sources 112 and/or the historical healthcare delivery information 148. In this regard, the AI response component 142 can employ machine learning to learn whether and how to respond to various significant events or conditions. Using machine learning analysis of these data sources, the response can be tailored based on the various contextual factors associated with the significant event or condition, including contextual factors associated with the patient (e.g., medical history, preferences, demographics, insurance, etc.), the clinicians involved, the clinicians available, the state and distribution of resources at the facility, and the like.

Figure 5:
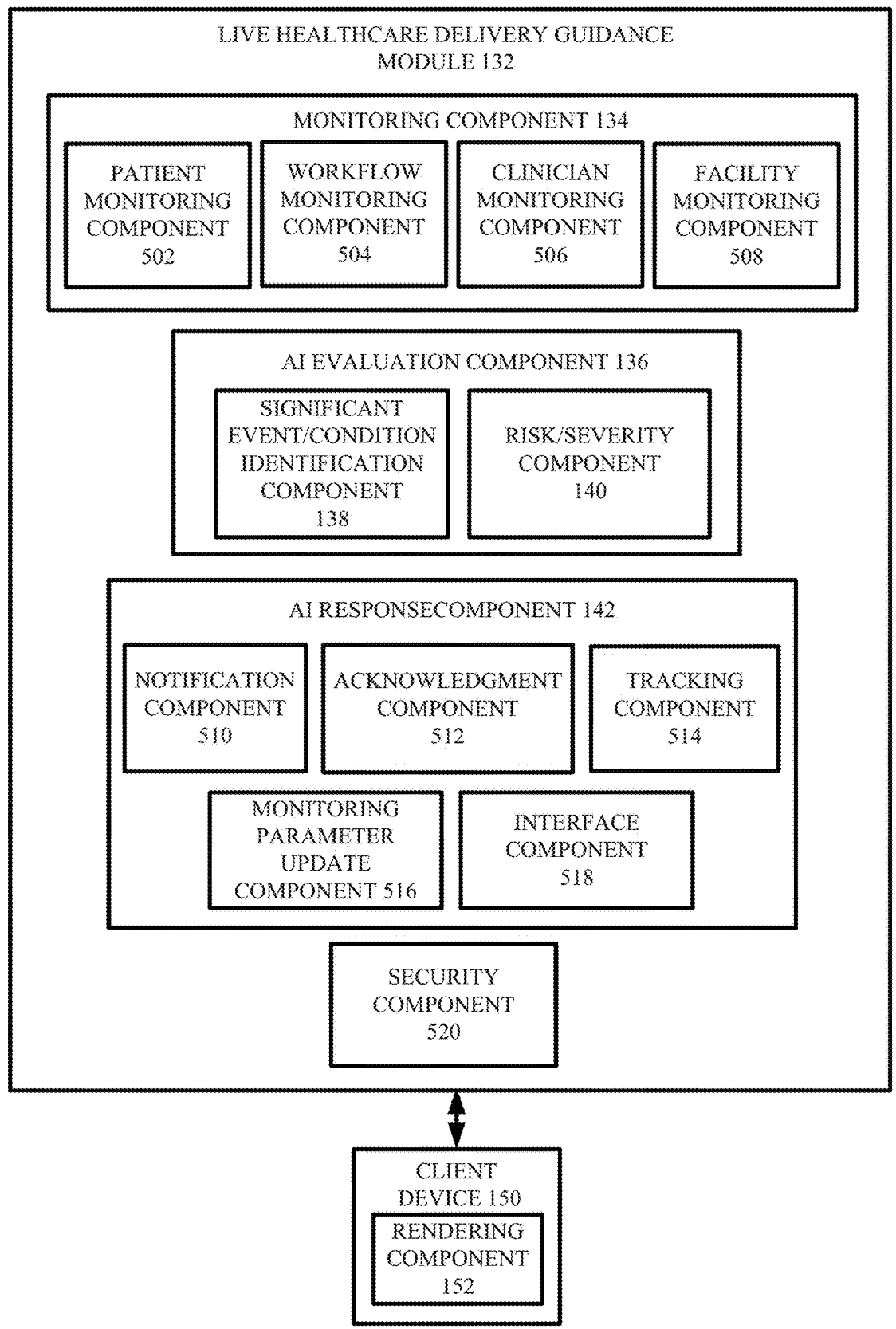
FIG. 5 illustrates an example live healthcare delivery guidance module that provides AI tactics to facilitate healthcare delivery in accordance with various aspects and embodiments described herein.
Figure 12:
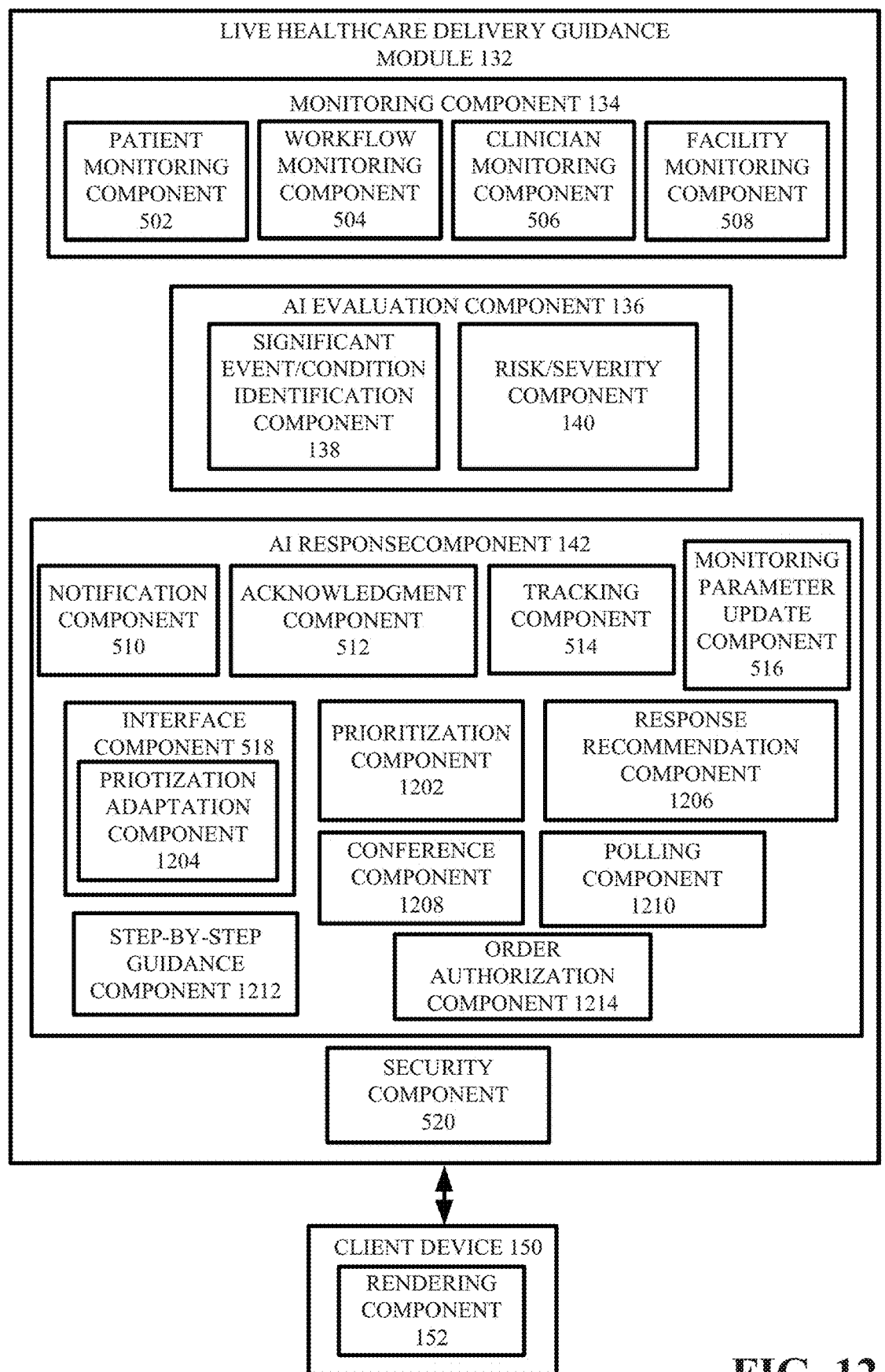
FIG. 12 illustrates an example live healthcare delivery module that provides AI tactics to facilitate healthcare delivery in accordance with various aspects and embodiments described herein.

Additional information regarding the responses that can be provided by the AI response component 142 and the way the AI response component 142 determines and infers appropriate responses for provision are discussed in greater detail infra with reference to FIGS. 5 and 12.

Figure 2:
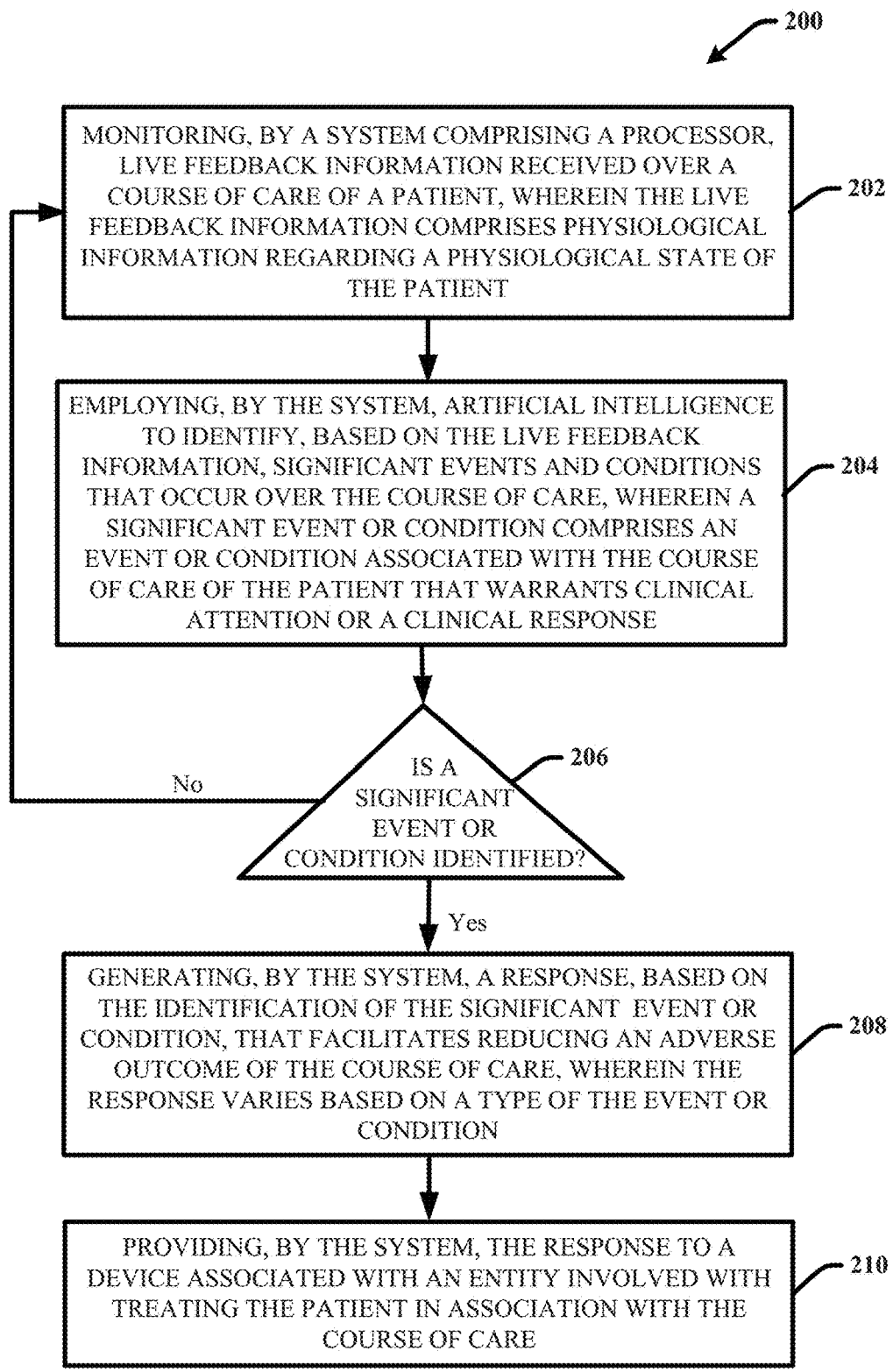
FIG. 2 presents a high-level flow diagram of an example method for facilitating healthcare delivery using AI tactics in accordance with various aspects and embodiments described herein.

FIG. 2 presents a high-level flow diagram of an example method 200 for facilitating healthcare delivery using AI tactics in accordance with various aspects and embodiments described herein. Method 200 presents a high-level flow diagram of an example implementation of system 100 to facilitate providing clinicians with evidence based evaluations of a current clinical scenario to facilitate making informed clinical decisions about the current clinical scenario while reducing adverse outcomes. Repetitive description of like elements employed in respective embodiments is omitted for sake of brevity.

With reference to FIGS. 1 and 2, at 202, a system comprising a processor (e.g., system 100) monitors live feedback (e.g., live feedback information 154) received over a course of care of a patient (e.g., via monitoring component 134), wherein the live feedback comprises physiological information regarding a physiological state of the patient. At 204, the system employs AI to identify, based on the live feedback information, significant events and conditions associated with the course of care of the patient, wherein a significant event or condition comprises an event or condition associated with the course of care of the patient that warrants clinical attention or a clinical response (e.g., via the AI evaluation component 136). At 206, the system determines whether a significant event or condition is identified. If not, the system continues to monitor the live feedback. However, if a significant event or condition is identified, then at 208, the system generates a response (e.g., via the AI response component 142), based on the identification of the significant event or condition, that facilitates reducing an adverse outcome of the course of care, wherein the response varies based on a type of the event or condition. Then at 210, the system provides the response to a device associated with an entity involved with treating the patient in association with the course of care (e.g., via the AI response component 142).

Many of the disclosed embodiments of the monitoring component 134, the AI evaluation component 136 and the AI response component 142 described herein employ machine learning analysis of the historical healthcare delivery information 148 and/or the information provided by the one or more healthcare information sources 112 to make determinations and/or inferences about the live feedback information 154. In this regard, the determinations and/or inferences can be based on entirety or a subset of the data included in the one or more healthcare information sources 112 and the historical healthcare delivery information 148 and can provide for reasoning about or inferring states of the system (e.g., system 100 and the like), environment, etc. from a set of observations as captured via events and/or data. For example, an inference can be employed to identify a specific context or action, or can generate a probability distribution over states, for example. The inference can be probabilistic (e.g., the computation of a probability distribution over states of interest can be based on a consideration of data and events). An inference can also refer to techniques employed for composing higher-level events from a set of events and/or data. Such an inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x4, x4, xn), to a confidence that the input belongs to a class, such as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

The type of machine learning employed by the live healthcare delivery guidance module 132 to make determinations and/or inferences about the live feedback information 154 in view of the information provided by the historical healthcare delivery information and/or the information provided by the one or more healthcare information sources 112 can vary. For example, the monitoring component 134, the AI evaluation component 136 and/or the AI response component 142 can employ unsupervised machine learning, supervised machine learning, semi-supervised machine learning or a combination thereof. In this regard, the live healthcare delivery guidance module 132 can make inferences about the live feedback information 154 by applying machine learning analysis of all or a subset of the information provided by the healthcare information sources 112 and/or the historical healthcare delivery information 148 prior to reception of the live feedback information 154 and/or coinciding with the time of reception of the live feedback information.

Figure 3:
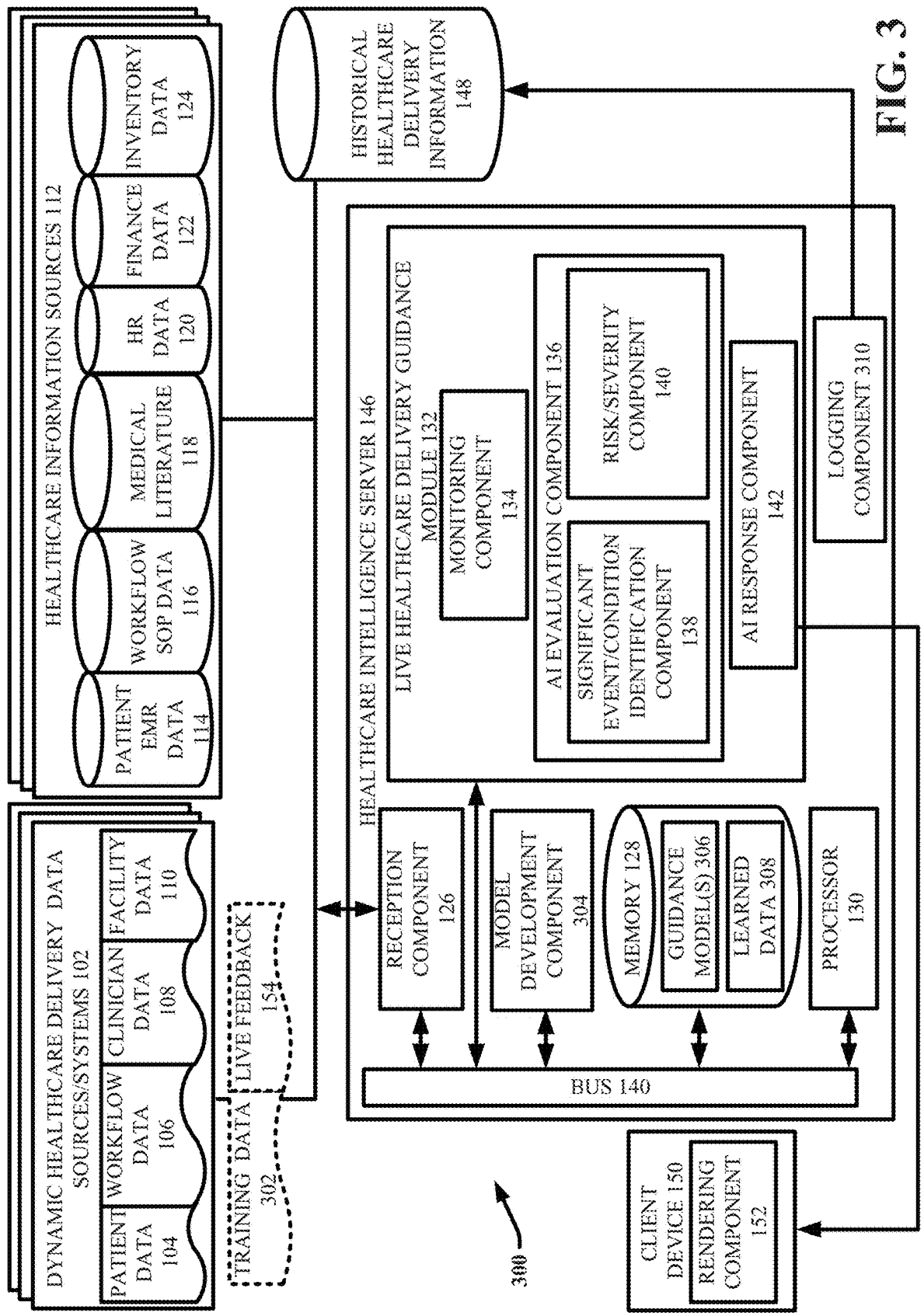
FIG. 3 illustrates an example system that facilitates developing and applying AI tactics to facilitate healthcare delivery in accordance with various aspects and embodiments described herein.

FIG. 3 illustrates another example system 300 that facilitates developing and applying AI tactics to facilitate healthcare delivery in accordance with various aspects and embodiments described herein. System 300 can include same or similar features and functionalities as system 100. System 300 provides some additional features and functionalities associated with applying supervised, semi-supervised, and unsupervised machine learning to facilitate making determinations and inferences about the live feedback information 154 by the live healthcare delivery guidance module 132.

In accordance with one embodiment, system 300 can employ supervised or semi-supervised machine learning to develop one or more guidance models 306 prior to application of system 300 to facilitate reasoning about and providing responses to the live feedback information 154. In this regard, the one or more guidance models 306 can include one or more mathematical models that have been trained and developed by the model development component 304 using training data 302 and the information provided by the healthcare information sources 112 and the historical healthcare delivery information. The training data 302 can include same or similar data as the live feedback information 154. These guidance models can be configured to facilitate providing guidance with respect to making clinical decisions associated with one or more defined procedures, SOPs, clinical scenarios, medical conditions, or the like. In this regard, the one or more guidance models 306 can be configured to receive live feedback information 154 as input and generate output information including but not limited to: an identified significant event or condition, a risk/severity of the significant event or condition, and/or an appropriate response to the identified significant event or condition. According to this embodiment, the AI evaluation component 136 and/or the AI response component 142 can employ the one or more guidance modules that have been previously developed by the model development component 304 based on the training data 302, the information provided by the one or more healthcare information sources 112 and/or the historical healthcare delivery information 148, when evaluating the live feedback information 154.

In accordance with system 300, the healthcare intelligence server 146 can also include logging component 310. In one or more embodiments, the logging component 310 can be configured to generate a log or report of the information received and processed by the live healthcare delivery guidance module 132. For example, the logging component 310 can log the live feedback information 154 monitored by the monitoring component 134, including information regarding patient data, workflow data, clinician data, and facility data 110 monitored for a patient, group of patients, clinician, group of clinicians and the like, over a course of care. The logging component 310 can further log information regarding the significant events/conditions identified by the significant event/condition identification component 138, responses provided by the AI response component, and information regarding actual responses performed by clinicians based on the information provided by the AI response component 142 as well as corresponding clinical and financial outcomes. The information logged by the logging component 310 can further be added to and collated with the existing, historical healthcare delivery information 148 and used to optimized and further tailor further decisions made by the live healthcare delivery guidance module 132. For example, in some embodiments, the model development component 304 can continuously or regularly optimize or adapt the one or more guidance models 306 based on the new logged historical healthcare delivery information. Accordingly, as more and more cases are logged, the live healthcare delivery guidance module 132 can continue learning and tailoring inferences and decisions about what constitutes a significant event or condition, and how to respond to that significant event or condition to facilitate reducing adverse outcomes and improving the accuracy and specificity of clinical decisions.

In some implementations, in association with applying unsupervised or semi-supervised learning, the live healthcare delivery guidance module 132 can regularly evaluate the information provided by the one or more healthcare information sources 112 and the regularly updated, historical healthcare delivery information 148 to learn new correlations and patterns in the data that relates to significant event or conditions, the severity/risk of significant events or conditions, and appropriate responses to the significant events or conditions. The learned information can further be stored in memory 128 as learned data and employed by the live healthcare delivery guidance module 132 to improve processing time associated with identifying and characterizing significant events and conditions based on the live feedback data and determining appropriate responses to the significant events and conditions.

Figure 4:
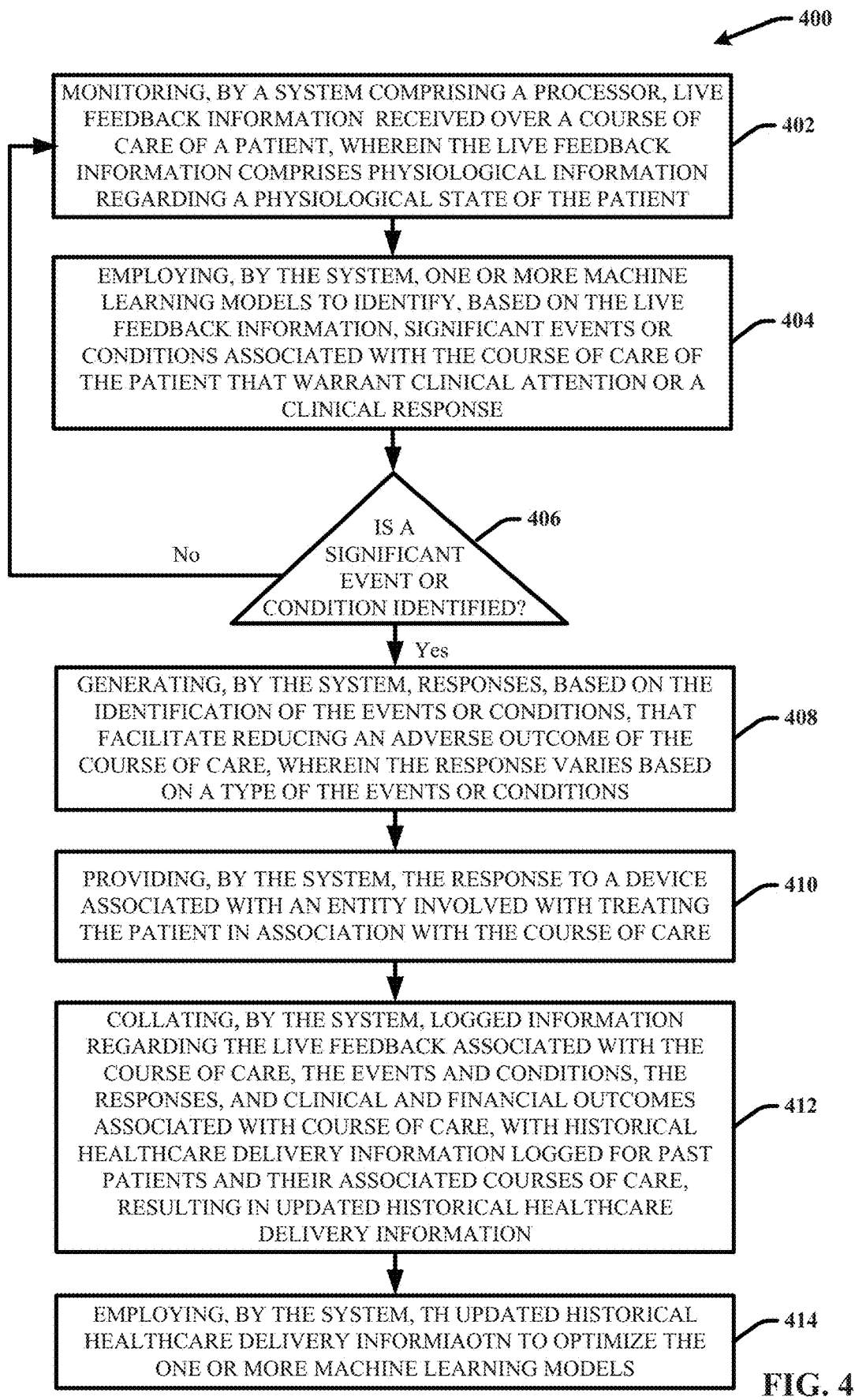
FIG. 4 presents a high-level flow diagram of an example method for developing and applying AI tactics to facilitate healthcare delivery in accordance with various aspects and embodiments described herein.

FIG. 4 presents a high-level flow diagram of another example method for developing and applying AI tactics to facilitate healthcare delivery in accordance with various aspects and embodiments described herein. Method 400 presents a high-level flow diagram of an example implementation of system 300 to facilitate providing clinicians with evidence based evaluations of a current clinical scenario to facilitate making informed clinical decisions about the current clinical scenario while reducing adverse outcomes. Repetitive description of like elements employed in respective embodiments is omitted for sake of brevity.

With reference to FIGS. 3 and 4, at 302, a system comprising a processor (e.g., system 300) monitors live feedback (e.g., live feedback information 154) received over a course of care of a patient (e.g., via monitoring component 134), wherein the live feedback comprises physiological information regarding a physiological state of the patient. At 404, the system employs one or more machine learning models (e.g., guidance models 306) to identify, based on the live feedback information, significant events or conditions associated with the course of care of the patient that warrant clinical attention or a clinical response (e.g., via the AI evaluation component 136). At 406, the system determines whether a significant event or condition is identified. If not, the system continues to monitor the live feedback. However, if a significant event or condition is identified, then at 408, the system generates responses (e.g., via the AI response component 142), based on the identification of the event or conditions, that facilitate reducing an adverse outcome of the course of care, wherein the responses vary based on types of the events or conditions. At 410, the system provides the responses to a device associated with an entity involved with treating the patient in association with the course of care (e.g., via the AI response component 142). At 412, the system collates logged information regarding the live feedback associated with the course of care, the events and conditions, the responses, and clinical and financial outcomes associated with course of care, with historical healthcare delivery information (e.g., historical healthcare delivery information 148) logged for past patients and their associated courses of care, resulting in updated historical healthcare delivery information (e.g., via logging component 310). At 414, the system employs the updated historical healthcare delivery information to optimize the one or more machine learning models (e.g., via model development component 304).

Although example methods 200 and 400 are described with respect to employing AI to evaluate and guide a single clinical scenario, it should be appreciated that system 100, system 300 and additional systems described herein can be employed by a healthcare organization to monitor, manage and guide healthcare delivery for many different patients, procedures, clinical scenarios, etc., occurring at the healthcare organization simultaneously. With these embodiments, the healthcare intelligence server 146 can employ various techniques to manage and distinguish between the different patients, procedures, clinical scenarios, etc. For example, in some implementations, different instances of the live healthcare delivery guidance module 132 can be set up to handle the different patients, procedures, clinical scenarios, and the like.

Turning now to FIG. 5, presented is another example embodiment of the live healthcare delivery guidance module 132 in accordance with various aspects and embodiments described herein. Repetitive description of like elements employed in respective embodiments is omitted for sake of brevity.

With reference to FIGS. 1 and 5, in the embodiment shown, the monitoring component 134 has been subdivided into a plurality of components that can respectively be configured to monitor different types of the live feedback information. In particular, the monitoring component 134 can include patient monitoring component 502 to monitor parameters associated with patient data 104 such as physiological parameters associated with a patient, parameters related to expressed symptoms and side effects expressed by the patient, parameter related to pain experienced by the patient, parameters related to the mental state or mood of the patient, parameters related to the condition of the patient, parameters related to the appearance of the patient, parameters related to the current location of the patient, and the like. The monitoring component 134 can include workflow monitoring component 504 to monitor parameters associated with workflow data 106, such as but not limited to, parameters related to actions performed by clinicians relative to a course of care for the patient, procedures performed, steps of the procedures performed, characteristics of the steps of the procedures performed (e.g., instruments and supplies used, location and size of incision, relative location of instrument to patients body, etc.), timing and order of the procedures and/or procedural steps performed and the like. The clinician monitoring component 506 can be configured to monitor parameters associated with clinician data 108, such as parameters identifying respective clinicians that perform respective actions, their workloads (e.g., number of current patients being treated and types of treatment required), their physiological and mental state, their availability, their current location and the like. Further the facility monitoring component 508 can be configured to monitor parameters related to the current context of a clinical scenario with respect to the facility based on facility data 110. For example, the facility monitoring component 508 can monitor parameters related to the status, location and availability of resources at the healthcare facility, including medical supplies and equipment, personnel, and rooms available.

As discussed supra, the AI response component 142 can be configured to determine or infer and provide one or more responses to a significant event or condition identified by the significant event/condition identification component 138 based on the monitored live feedback information 154. In one or more embodiments, an appropriate response can include generating and sending a notification concerning an identified significant event or condition, requiring an entity to provide feedback acknowledging the notification, and/or tracking one or more parameters associated with the significant event or condition tracking a parameter associated with the clinically significant event or condition, and determining a new parameter for tracking that is related to the significant event or condition and automatically beginning tracking of the new parameter. In accordance with these embodiments, the AI response component 142 can include notification component 510, acknowledgment component 512, tracking component 514, monitoring parameter update component 516, and interface component 518.

The notification component 510 can be configured to generate and send a notification to an appropriate entity regarding an identified significant event or condition (e.g., as identified by the AI evaluation component 136). For example, in implementations in which the significant event or condition is related to a patient, the notification component 510 can be configured to generate and send a notification for rendering at one or more client devices (e.g., client device 150) associated with one or more clinicians responsible for treating the patient. In another example, in an implementation in which the notification concerns a clinician, such as a notification regarding a violation of an SOP associated with a current clinical scenario involving the clinician, or a notification indicating the clinician has expressed a level of fatigue that renders the clinician unfit to perform a particular medical procedure, the notification component 510 can send the notification to the clinician or an entity responsible for managing the performance of the clinician.

In some embodiments, the notification can include an electronic notification in the form of a text message, an email, a push-notification and the like. With these implementations, the notification can be configured for rendering at the client device 150 (e.g., via rendering component 152) in a suitable format. For example, the notification can include visual content configured for rendering in a visual format via a display. The notification can also include an audible notification, (e.g., an alarm), a sensory notification (e.g., a vibration), and the like. The notification can include information that identifies or indicates the reason for the notification, including but not limited to: the specific event or condition observed, timing of occurrence of the event or condition, the patient associated with the significant event or condition, the clinician associated with the significant event or condition, and the like. In some embodiments in which the risk/severity component 140 determines a risk/severity score for the significant event or condition, the notification can also include the risk/severity score.

In some embodiments, the notification component 510 can be configured to generate and send notifications regarding all identified significant events and conditions. In other embodiments, the notification component 510 can be configured to generate and provide notifications for certain types of significant events or conditions while forgoing generation and provision of notifications for other types of significant events or conditions. For example, the notification component 510 can be configured to provide notification for events that involve a violation of an SOP relevant to a current clinical scenario, but forgo sending notifications for changes in certain physiological parameters monitored for a patient, or vice versa. In another example, the notification component 510 can be configured to send notifications for significant events or conditions that warrant an action for performance by a clinician (e.g., administering a drug, performing a procedure, etc.), while forgoing generation and/or sending of notifications regarding significant events or conditions that do not warrant an action. With these embodiments, the types of significant events or conditions that warrant generation and provision of notifications can be predefined. In yet another embodiment, the notification component 510 can be configured to generate and send notifications based on a risk/severity score associated with an identified significant event or condition. For example, the notification component 510 can be configured to generate and send notification for events or conditions having a risk/severity score above a threshold score. Still in other embodiments, the notification component 510 can be configured to generate and provide different types of notifications to reflect a type of condition or event for which a notification is based and/or to reflect a level of risk/severity associated with the condition or event. For example, notifications associated with different risk/severity levels can be associated with different, visual properties, sounds, symbols, vibrations, etc. that indicates the level of risk/severity associated with the event or condition for which the notification is based.

In one embodiment, the notification component 510 can further determine an entity for which to provide a notification regarding a significant event or condition based on the type of significant event or condition and/or the risk/severity associated with the significant event or condition. For example, in scenarios in which several different clinicians having different roles and responsibilities are involved in a patient's care, the different clinicians can be responsible for assessing and/or responding to different types of events or conditions. In this regard, a nurse can be responsible for monitoring changes in a patient's blood pressure while the attending physician may be responsible for administering medication. In another example, a nurse can be responsible for reviewing and/or responding to low risk events or conditions while the attending physician may be responsible for responding to high risk events or conditions. With this embodiment, the notification component 510 can determine the appropriate entity for providing a notification concerning an identified significant event or condition based on the type of the event or condition and/or a risk/severity score associated with the event or condition and the roles and responsibilities of clinicians at the healthcare facility.

In some embodiments, in association with providing a notification concerning an identified significant event or condition, the acknowledgment component 512 can facilitate ensuring that the notification was in fact received and acknowledged by an appropriate entity by requiring the entity to provide feedback acknowledging receipt. As a result, the live healthcare delivery guidance module 132 can ensure clinicians become informed of and acknowledge significant events or conditions thereby minimizing the possibility of adverse outcomes that could result from failure to acknowledge such significant events or conditions. The acknowledgment component 512 can further facilitate recording or otherwise documenting (e.g., by the logging component 310) that acknowledgment was received, timing of receipt, and who the acknowledgment was received from, so that the entity providing the acknowledgment can be held accountable. Accordingly, if an adverse outcome does arise, the live healthcare delivery guidance module 132 can provide documentation regarding whether failure to acknowledge the significant event or condition was a contributing factor. Likewise, the live healthcare delivery guidance module 132 can identify scenarios where a clinician acknowledged a significant event or condition yet did not respond appropriately or in a manner otherwise directed by an SOP associated with the clinical scenario. In this regard, the clinician can be held accountable for potential negligence in the event an adverse outcome arises that can be attributed to the inappropriate response.

In some embodiments, the acknowledgment component 512 can be configured to request or require provision of feedback acknowledging all notifications generated and provided by the notification component 510. In other embodiments, the acknowledgment component 512 can be configured to selectively choose which notifications require acknowledgment based on the type of the event or condition and/or a level of severity associated with the event or condition for which the notification is based. Further, in some implementations, the acknowledgment component 512 can require an entity to sign-off on or otherwise acknowledge a notification regarding a significant event or condition based on the type of the significant event or condition and/or a risk/severity score associated with the event or condition. For example, for a notification regarding a low risk/severity event, acknowledgment by a nurse may suffice, while a notification regarding a high risk/severity event may require acknowledgment from the attending physician. In some implementations, to ensure the correct entity acknowledges a notification, the acknowledgment component 512 can receive feedback including a unique code, name, identifier or the like, that represents the entity. With these implementations, the notification component 510 can be configured to resend the notification or otherwise keep a notification active (e.g., in the forefront of the display screen, or if an alarm, continuing to sound) until feedback information is received comprising the unique code, name, identifier, etc., that indicates the authorized entity has signed-off on the event.

The way feedback acknowledging a notification is received can vary. In one implementation, a notification generated and sent by the notification component 510 can include or be associated with a mechanism for receiving feedback to indicate the notification was received and acknowledged. For example, the notification can be configured to remain visible in an area of a GUI in a pop-up display window or the like until input is received dismissing the notification. According to this example, the acknowledgment component 512 can receive a response indicating the notification was acknowledged based on user input dismissing the notification. The acknowledgment component 512 can further determine the entity from which the acknowledgment was received based on the client device and/or user account from which the acknowledgment was received. In another example in which the notification comprises a text message sent to ta mobile device, the notification can include a prompt directing the user to respond to the text message to indicate the notification was received.

In addition to providing notifications in response to identification of significant events or conditions, in other embodiments, an appropriate response to an identified significant event or condition can include tracking or otherwise documenting information regarding occurrence of the significant event or condition. For example, in some embodiments, the tracking component 514 and/or the logging component 310 can generate a record of every (or in some cases one or more) identified signification event or condition, even if the significant event or condition does not warrant notification and/or acknowledgment in real-time. For instance, implementation in which performance of workflow events are considered significant events, the tracking component 514 can track information regarding what workflow events were performed, when they were performed, who they were performed by, the outcomes of the workflow events, and the like. The tracking component 514 and/or the logging component 310 can also track information regarding significant conditions associated with a patient, including when they occurred, responses taken and by whom. In this regard, the tracking component 514 and/or the logging component 310 can develop a detailed record regarding all aspects of a course of care of a patient.

In other embodiments, the tracking component 514 and the interface component 518 can provide a tracking tool that facilitates visually tracking information regarding significant events or conditions in real-time. The tracking tool includes a GUI with a dynamic visualization that facilitates tracking and monitoring significant events and conditions associated with a course of patient care, a procedure, a clinical environment, and the like, thereby enabling health care providers to efficiently and effectively manage care of their patients.

In one or more embodiments, the interface component 518 can be configured to generate a GUI including a visualization that resembles a chart having a plurality of input compartments defined by a first axis having columns corresponding to sequential points in time over the course of the care and a second axis having rows respectively corresponding to patient care events or patient conditions associated with the course of the care. Based on received information regarding the occurrence or a characteristic of a significant event or condition associated with the course of patient care, the interface component 518 can fill one or more input compartments respectively corresponding to a point or period associated with the occurrence event or condition. For example, in some implementations, the interface component 518 can be configured to automatically fill a compartment corresponding to a patient care event or condition based on identification of the patient care event or condition by the AI evaluation component 136. In other implementations, medical personnel can input information regarding an event or condition directly via the GUI. Thus, the GUI can chart up to date information regarding conditions of the patient (e.g., heart rate, blood pressure, temperature, etc.) and events (e.g., administration of a drug) associated with care of the patient from the time of admittance to a current point in time. As a result, the graphical user interface can depict a complete timeline picture of the various aspects of a course of patient care from the time of admittance to a current point in time.

The GUI can be presented to a clinician at client device (e.g., client device 150) that is accessible to medical personal involved in the patient care. For example, the patient tracking GUI can be provided on a device located in a patient's hospital room, a personal mobile device associated with respective clinicians (e.g. a handheld device, a heads-up display, a VR device, an AR device, and the like). In some implementations, the client device 150 can receive direct input provided by clinicians regarding patient care events and conditions over the course of care (e.g., via touch screen, keypad, voice to text, or the like).

Figure 6:
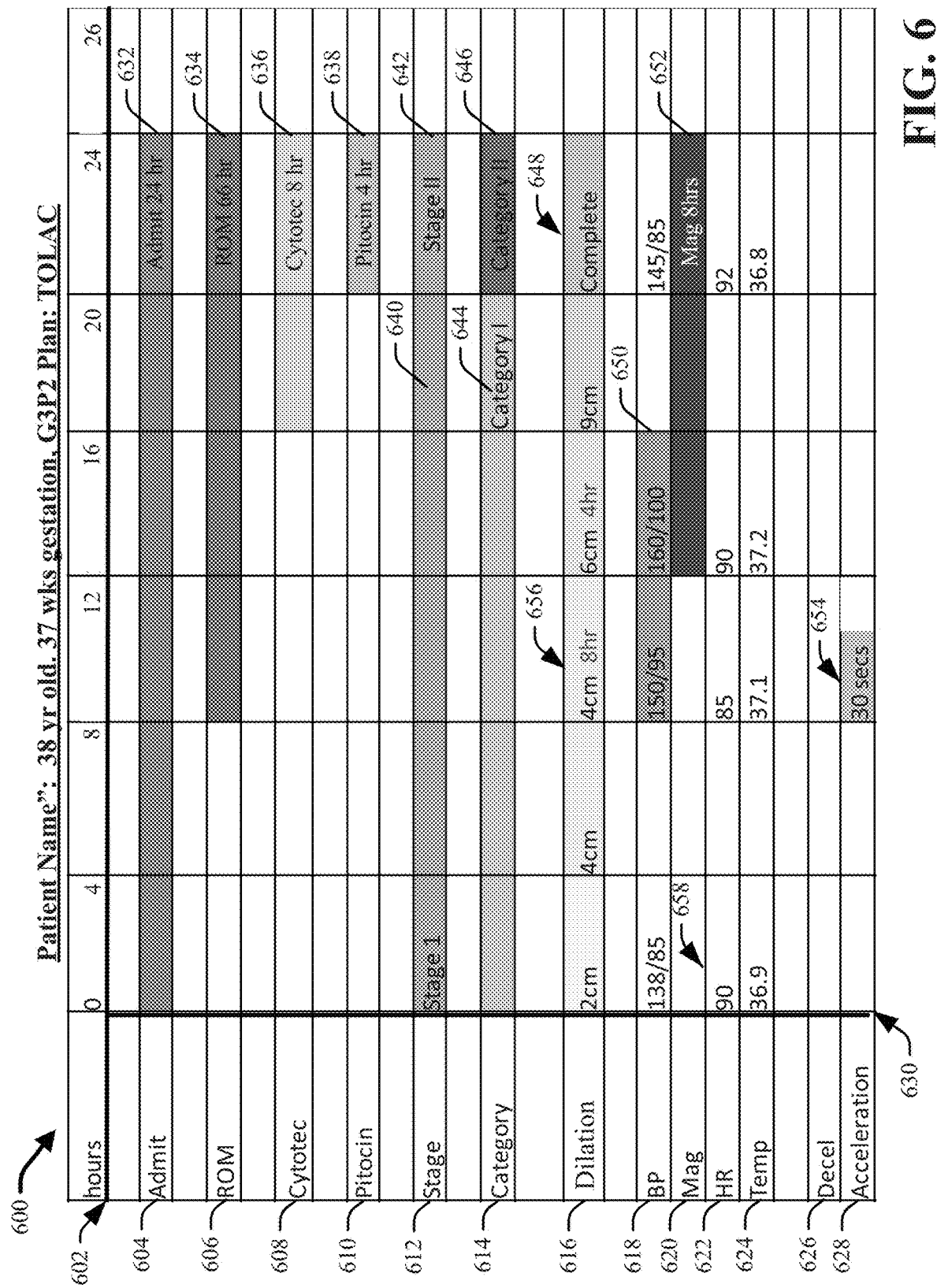
FIG. 6 illustrates a block diagram of an example user interface facilitates tracking and displaying patient information over the course of care in accordance with various aspects and embodiments described herein.

For example, FIG. 6 depicts an example GUI 600 that facilitates tracking patient care events and patient conditions over the course of labor in accordance with aspects and embodiments described herein. In one or more embodiment GUI 600 can be generated by the tracking component 514 and the interface component 518 and rendered at a client device 150 via rendering component 152 in association with the course of care of a patient. Although GUI tracks a course of care of a patient in labor, it should be appreciated that the feature and functionalities of GUI 600 can be applied to track patient events and conditions related to various other types of medical procedure, diagnosis, conditions and course of patient care.

GUI 600 organizes and presents information associated with care of a patient over the course of labor as a function of time. In the embodiment shown, the GUI 600 graphically depicts various patient care events and conditions that occurred over the course of labor up until a current time of 24 hours after admittance of the patient. The GUI 600 includes a plurality of compartments or cells defined by a first axis 602 and a second axis 630. The first axis 602 corresponds to a timeline and includes a plurality of columns respectively associated with sequential points in time, beginning with a time at which the patient was admitted. For example, the first axis 602 includes a plurality of columns respectively associated with four hour increments of time following admittance of the patient. The second axis 630 includes a plurality of rows respectively associated with a data input fields corresponding to patient care events or conditions. In particular, the second axis 630 includes a plurality of rows that correspond to various patient care events and conditions associated with labor, including admittance 604, rupture of membranes (ROM) 606, provision of cytotec 608, provision of pitocin 610, stages of labor 612 (e.g., associated with the mother and/or the infant), categories of labor 614 (e.g., associated with the mother and/or the infant), dilation 616, blood pressure (BP) 618, magnesium (Mag) or maternal hypertension 620, fetal heart rate (HR) 622, maternal temperature 624, deceleration of fetal HR 626, and acceleration of fetal HR 628.

It should be appreciated that the data fields corresponding to the respective rows of GUI 600 are not limited to those described above. A data field in GUI 600 can be adapted to correspond to any possible patient care event or condition associated with a course of labor. For example, one or more of the data fields listed above and depicted in GUI 600 can be removed and/or additional data fields can be added. For instance, row 620 corresponding to Mag monitoring could be removed and a new row could be added corresponding to fetal station that facilitates tracking information regarding fetal station. In an aspect, GUI 600 can be divided into two sections, one having data input rows corresponding to patient care events and conditions associated with the mother and another corresponding to patient care events and conditions associated with the infant.

In one or more embodiments, the GUI 600 can be updated in real-time or substantially real-time to include and display information that corresponds to a current point in time over the course of labor. In this regard, as time progresses beyond 24 hours, the GUI 600 can add columns corresponding to new points in time. It should be appreciated that the number of columns added respectively corresponding to new points in time can be unlimited such that the GUI 600 can be continuously updated to reflect a course of care over any duration of hours or days. In some implementations, based on display size restrictions, the number of columns that can be displayed on a single screen or display window can be limited. With these implementations, the GUI 600 can display the columns corresponding to the most recent points in time and the display window can include a scrolling mechanism that allows a user to scroll back in time to view previous time columns and associated data.

With reference to FIGS. 5 and 6, a tracking GUI such GUI 600 can facilitate visually tracking, (e.g., in real-time or substantially real-time), the occurrence of significant events or conditions over the course of care as a function of time. The tracking GUI can also track information regarding characteristics associated with significant events or conditions that occur, such as information regarding a value or level of a tracked physiological parameter, an entity (e.g., a clinician and/or medical device) that provided treatment corresponding to an event, an outcome of an event, and the like. In some implementations, the interface component 518 can be configured to automatically add data to the tracking GUI to reflect the occurrence of a significant event or conditions identified by the significant event/condition identification component 138. In other implementations, the tracking component 514 can selectively determine what events and conditions to track via the GUI that are relevant to a current course of care or clinical scenario. The tracking component 514 can also selectively determine what events and conditions to track via the GUI based on a type of the event or condition and/or a risk/severity score associated with the event or condition.

Still in various other embodiments, the tracking GUI can receive user input that defines one or more events or conditions for tracking and further identifies information regarding the occurrence and/or a characteristic of a significant event or condition. For example, the tracking component 514 and/or the interface component 518 can receive user input (e.g., via reception component 126) directed towards a cell/compartment of a patient tracking interface indicating occurrence and/or a characteristic of a patient care event or patient condition represented by the cell/compartment at a time corresponding to the cell/compartment. In another example, the tracking component 514 and/or the interface component 518 can receive user input (e.g., via reception component 126) merely identifying occurrence and/or a characteristic of a patient care event or patient condition. According to this example, based on the received input, the interface component 518 can provide data (e.g., text, a color, a symbol) into the appropriate cell or cells of a patient tracking interface that correspond to the patient care event or patient condition at the time at which the input was received. The data can include text, a fill color, and/or a symbol representative of the occurrence and/or a characteristic of the patient care event or patient condition. In an aspect, when input is received for a new patient care event or condition that is not represented by the patient tracking interface, interface component 518 can automatically generate a new data input field/row corresponding to the new patient care event or condition. The tracking component 514 and/or the interface component 518 can receive user input (e.g., via reception component 126) defining a data input field/row for inclusion in a patient tracking interface and/or defining time segments for association with respective columns of the patient tracking interface.

For example, the tracking GUI can allow a user to select a cell (e.g., cell 656) corresponding to a time or hour increment (e.g., 12 hours) and data input field (e.g., dilation 616) and enter information for display in the cell indicating occurrence and/or a characteristic of the patient care event or condition represented by the data field at the time or hour increment (e.g., 4 centimeters (cm) for 8 hours. For example, using a data interfacing tool (e.g., soft keys, touch screen, voice detection, etc.), a user can select an input compartment defined by a row and a column and enter information representative of the patient care event or condition associated with the row at a time represented by the column. The entered information can include a fill color and/or text indicating occurrence of the patient care event or condition and/or identifying a characteristic of the patient care event or condition.

In one or more embodiments, the interface component 518 can be configured to fill one or more input compartments of a patient tracking interface (e.g., GUI 600 and the like) to reflect one or more aspects associated with tracked events or conditions. For example, in some implementations, the interface component 518 can fill one or more compartments of a patient tracking interface that respectively corresponds to a point or period of time associated with occurrence of a patient care event or patient condition in response to reception input identifying occurrence of the patient care event or patient condition. For example, in response to reception of information indicating intravenous magnesium was started on the patient at time of 1:23 pm, the interface component 518 can provided data into a cell/compartment of the patient tracking interface corresponding to a data input field/row for intravenous magnesium at time of 1:23 pm. The data can include text, color, and/or a symbol indicating that intravenous magnesium has been administered. In example, the interface component 518 can fill one or more compartments of a patient tracking interface that respectively corresponding to a point or period of time associated with occurrence of a patient care event or patient condition with data representative of a characteristic of the patient care event or patient condition in response to reception of input identifying the characteristic. For example, in response to reception of information identifying a degree of dilation of 3 cm of a patient at time 12:45 pm, the interface component 518 can input data into a cell/compartment of the patient tracking interface corresponding to a data input field/row for dilation at time 12:45 pm. The data can include text, color, and/or a symbol indicating the patient has a degree of dilation of 3 cm.

The tracking component 514 can also be configured to track progression of time over the course of care. For example, the tracking component 514 can include a clock that identifies a time when patient care begins and tracks passage of time over the course of care. The tracking component 514 can thus determine a current point in time, and/or an amount of time passed following initiation of the course of care, associated with receipt of information identifying occurrence and/or a characteristic of a patient care event or patient condition. The tracking component 514 can further determine the appropriate area of a timeline (e.g., column) to include data identifying the occurrence and/or a characteristic of the patient care event or patient condition based in part on a time of receipt of the input.

In some embodiments, the tracking component 514 can receive information regarding a patient care event or patient condition identifies a time of onset of a patient care event or patient condition that is ongoing. According to these embodiments, the tracking component 514 can track progression of time over the course of care and the interface component 518 can automatically fill input compartments of a row corresponding to the patient care event or patient condition over the course of care until new input is received that identifies a change in the patient care event or patient condition or until the course of patient care ends. For example, following receipt of data indicating that a patient has entered stage I of labor, the interface component 518 can automatically fill compartments/cells of a row corresponding to stage I of labor to indicate that the patient is currently in stage I of labor as time progresses until new information is received that the patient is no longer in stage I of labor. In another aspect, following receipt of data indicating that a patient care event or patient condition (e.g., ROM) has occurred, the interface component 518 can automatically fill compartments/cells of a row corresponding to the patient care event or patient condition to indicate an amount of time elapsed following occurrence of the patient care event or patient condition The interface component 518 can employ various types of visual data to indicate occurrence and/or a characteristic of the patient care event or condition. For example, the interface component 518 can display text characters, symbols and/or colors in various compartments/cells to mark occurrence or a characteristic associated with a patient care event or patient condition. In an aspect, compartments associated with various patient events or conditions are filled with a color to indicate occurrence and/or a characteristic of the patient care event or condition at a time associated with the input compartment. Different colors can be used to distinguish between different patient care events or conditions and/or characteristics of the patient care events or conditions. For example, in GUI 600, each cell corresponding to an amount of time passed following admittance of the patient is filled with blue, each cell corresponding to an amount of time passed following ROM is filled with green, each cell corresponding to an amount of time passed following administration of cytotec is filled with yellow, etc.

In an aspect, different colors or color shades can be employed to indicate a characteristic of the information represented thereby. For example, different shades of yellow can be employed to distinguish between different degrees of dilation. As seen in GUI 600, as dilation increases from 2 cm to 9 cm, the shade of color associated with each cell including the dilation information intensifies. For example, a change in color from bright yellow to lime green in cell 648 can be used to indicate dilation is complete. In another example, different colors can be employed to distinguish between different stages associated with labor (e.g., stage I is marked by light green, stage II marked by light purple) and different categories associated with labor (e.g., category I is marked by pink and category II is marked by red).

In some embodiments, the interface component 518 can provide data within a single cell, (or portion of a single cell), to mark a fixed event or condition or a characteristic associated with on ongoing event or condition at a specific point or period. For example, cell 656 includes color data and text data identifying a degree of dilation at time 12 hours. In another example, cell 654 includes color data and text data identifying an amount of time (e.g., 30 seconds) associated with heart rate acceleration between 8 and 12 hours following patient admittance. In yet another example, cell 658 includes text data identifying a maternal heart rate at 4 hours after admittance.

Further, in association with patient care events or condition that are ongoing, the interface component 518 can fill sequential cells or compartments of a row corresponding to the times the event or condition occurs with a same solid or color, resulting in the creation of a horizontal color bar. These color bars can establish a visual timeline for the duration of a patient care event or condition and/or a duration from onset of occurrence of the event or condition. For example, color bar 632 corresponds to an amount of time elapsed following admittance of the patient, color bar 634 corresponds to an amount of time elapsed following ROM, color bar 636 corresponds to an amount of time elapsed following administration of cytotec, color bar 638 corresponds to an amount of time elapsed following administration of pitocin, color bar 640 corresponds to an amount of time elapsed while the patient was in stage I of labor, color bar 642 corresponds to an amount of time elapsed while the patient was in stage II of labor, color bar 644 corresponds to an amount of time elapsed while the patient was in category I of labor, color bar 646 corresponds to an amount of time elapsed while the patient was in category II of labor, color bar 650 correspond to an amount of time where the maternal blood pressure was high (e.g., above 145/90), and color bar 652 corresponds to an amount of time elapsed following administration of magnesium.

In an aspect, the interface component 518 can be configured to automatically populate cells following the onset of a certain defined event or condition as time progresses to generate a visual timeline marking the duration of time passed from the onset. For example, after information is received and/or determined that marks the onset or occurrence of a patient care event or condition, cells associated with the patient care event or condition following the time the data is initially received can automatically be filled (with a same color) to indicate an amount of time elapsed following onset of the patient care event or patient condition and/or an amount of time during which the patient event or condition persists. For example, when a patient is admitted, the interface component 518 (or a user via direct input to the GUI) can mark or fill the initial cell at time 0 hours and field admittance 604 (or otherwise provide input data indicating when the patient was admitted for association/display in admittance field 604). Respective cells associated with the admittance field/row 604 can then auto populate as time progresses with data (e.g., the color blue) until data is received indicating the patient has been released. According to this aspect, a clock can be employed to detect passage of time in association with auto filling of cells.

In addition, key information associated with a color bar can be displayed in text at the tip of the color bar. For example, as shown in GUI 600, color bar 632 includes text at the tip thereof indicating the patient has been admitted for 24 hours, color bar 634 includes text at the tip thereof indicating it has been 16 since ROM, color bar 636 includes text at the tip thereof indicating cytotec has been applied 8 hours ago, etc. In an aspect, the interface component 518 can dynamically update the information included within a color bar to reflect progression of time. For example, information identifying an amount of time represented by the color bar can be included at the tip of the color bar and be automatically updated or calculated based on a current point in time.

In another aspect, data fields associated with ongoing patient conditions/events are configured to automatically populate cells associated therewith as time progresses until new input indicating a change in the patient condition/event is received. For example, when a patient enters stage I of labor, the interface component 518 (or a user via direct input) can mark or fill the initial cell at time 0 hours and data field/row stage 612 (or otherwise provide input data indicating when the patient entered stage I of labor for association/display in stage field 612). The interface component 518 can further automatically fill respective cells associated with data field/row stage 612 as time progresses with data (e.g., the color light green) until new data is received indicating the patient is no longer in stage I of labor. For example, regarding generation of GUI 600, after the passage of 20 hours, new data can be received indicating the patient has entered stage II of labor. At this point, the color bar 640 associated with stage I of labor is fixed and a new color bar 642 associated with stage II of labor is initiated.

In addition to data fields corresponding to patient care events or patient conditions, the interface component 518 can be configured to automatically add columns corresponding to new points or segments of time as the points or segments of time occur. For example, each time a new period of 4 hours passes or is initiated, the interface component 518 can generate a new column corresponding to the new period of 4 hours. It should be appreciated that columns associated with the horizontal timeline axis can be associated with various increments of time and are not limited to 4 hour increments. For example, columns associated with axis 102 can respectively correspond to sequential time segments of 15 minutes, 30 minutes, one hour, two hours, etc.

As previously noted, in one aspect, a user can select a specific row, column or cell and input data (e.g., a color, text, a symbol) into the specific row, column or cell. For example, a user can select a cell corresponding to a patient care event or condition occurring at a point in time and input data or fill the cell to identify occurrence and/or a characteristic of the patient care event or condition. In another example, only those cells associated with a current point in time can be activated for selection/receipt of input. According to this example, a user cannot go back in time and change previously entered data and/or skip ahead in time to input data. Also, according to this example, because data input for a data field will be automatically associated with a cell corresponding to a current point in time, rather than selecting the cell, the user can merely select the data field for which input is desired. For example, a user can provide input (or the input can be received automatically from a medical device or other device) indicating the patient's current temperature is 37.2° C. Based on timing of receipt of the input, the interface component 518 can automatically enter the input into the appropriate cell located at a column corresponding to the timing of receipt and a row or data input field corresponding to temperature (e.g., data input field/row 624 at column 16 hours). In an aspect, to facilitate efficient user entry of data into a tracking interface (e.g., GUI 600), one or more data fields or cells can be associated with a drop-down menu that is activated upon selection of the data field or cell. The drop-down menu can provide various data input options that can be selected for entry into the data field or cell.

In some embodiments, the various data fields (e.g., data fields 604-628) of a patient tracking interface (e.g., GUI 600) can be pre-defined or defined based on user input. For example, patient tracking interface that facilitates tracking a patient undergoing labor can include one or more pre-defined data fields corresponding to key data points (e.g., significant physiological parameters, events, conditions, etc.) known to be relevant to a course of care of a patient undergoing labor. In another example, a GUI that facilitates tracking a patient suffering from acute coronary syndrome can include a plurality of pre-defined data fields known to be relevant to a course of care of a patient suffering from acute coronary syndrome. In yet another example, a user can provide input defining respective data fields associated with a course of patient care. According to this example, a user can add any number N of data fields to correspond to a relevant patient condition or patient care event that can be tracked over a course of care to facilitate making clinical decision. For example, each time a new drug is administered to the patient, a new data field corresponding to the drug can be added.

In various additional embodiments, the tracking component 514 and/or the interface component 518 can be configured to automatically generate and adapt a patient tracking interface (e.g., GUI 600 and additional patient tracking interfaces described herein) without receiving user input. For example, based on identification of a significant event or condition by the significant event/condition identification component 138, the tracking component 514 and/or the interface component 518 can be configured to automatically generate and fill one or more compartments respectively corresponding to a point or period of time associated with the occurrence of the significant event or condition. The interface component 518 can also automatically generate and integrate visual symbols, texts, color changes and the like in the tracking interface to provide some description regarding one or more relevant details or characteristics associated with the tracked condition or event. The interface component 518 can further automatically create a timeline associated with the occurrence of the significant event or condition when appropriate, such as for condition or events that are ongoing and/or for conditions or events wherein the duration of time passed from onset is relevant to clinical decision making. In some implementation, such conditions or events can be predefined. In other embodiments, the tracking component 514 can employ machine learning to determine when to create a timeline for a significant event or condition.

In one or more embodiments, a tracking interface can be set up by the tracking component and the interface component 518 to track a defined clinical scenario and the tracking component 514 and the interface component 518 can be configured to automatically track, via the tracking interface, information regarding significant events and conditions identified by the significant event/condition identification component 138. For example, a tracking interface can be tailored to track information that is relevant to a patient, a clinician (e.g., including information pertaining to multiple patients the clinician is treating over a same period), an area of a healthcare facility, a clinical scenario involving a plurality of patients, clinician, supplies, and the like. In some implementation, in association with setting up a tracking interface for a clinical scenario, the tracking component 514 and/or the interface component 518 can receive input defining the boundaries of the clinical scenario. In this regard, the tracking component 514 and/or the interface component 518 can receive input requesting a tracking interface for a patient, group of patients, clinician, group of clinicians, area of the healthcare facility (e.g., the emergency room, the intensive care unit, etc.), and the like. Based on the received input, the tracking component 514 and the interface component 518 can generate a tracking interface (e.g., GUI 600 and the like), that is tailored to visually track information regarding significant events and conditions that are relevant to the defined clinical scenario.

In some embodiments, the tracking component 514 and/or the interface component 518 can be configured to automatically track all identified event and conditions relevant to a specific clinical scenario that the tracking interface is designed to track. In this regard, in association with tracking a course of patient care (e.g., in association with a procedure, a series of procedures, a clinical consultation, arrival at the emergency room, initiation of treatment, etc.), the tracking component 514 and/or the interface component 518 can be configured to automatically track, via the tracking interface, information regarding all significant events or conditions that are identified by the significant event/condition identification component 138.

In other embodiments, the tracking component 514 can selectively track information regarding a subset of significant events or conditions associated with a clinical scenario. With these embodiments, the tracking component 514 can be configured to determine or infer which significant events and conditions to track that are relevant to a clinical scenario via the tracking interface. In some implementations, to determine which significant events and/or conditions to track for a clinical scenario, the tracking component can employ machine learning analysis of the information provided by the historical healthcare delivery information 148 and/or the information provided in the one or more healthcare information sources 112 and the information describing the boundaries of the tracking interface. In some embodiments, the tracking component 514 can employ information regarding the diagnosis of a patient, the condition of a patient, the role of the clinicians, the procedures involved, and the like to facilitate automatically determining what significant events and conditions to track via the tracking interface. For example, based on a determination that a patient has begun labor (e.g., as determined by the significant event/condition identification component 138 based on the live feedback information), the tracking component 514 can determine that this significant event should be tracked based on predefined information indicating this event should be tracked (e.g., stored in memory 128 and accessible to the tracking component 514), and/or based on machine learning evaluation of the historical healthcare delivery information 148 and/or the information provided by the one or more healthcare information sources.

In some embodiments, the AI response component 142 can include monitoring parameter update component 516 to provide for automatically determining or inferring (e.g., using machine learning) one or more additional parameters related to an identified significant event or condition that should also be tracked using the tracking tool based on a significant event or condition identified by the significant event/condition identification component 138. For example, based on a determination that a patient has begun labor, the monitoring parameter update component 516 can determine or infer (e.g., using machine learning) that the heart rate of the infant is a relevant physiological parameter that should be tracked over the course of labor. The monitoring parameter update component 516 can further automatically add the additional parameter to the tracking interface and update the tracking interface in real-time to reflect tracking of the new parameter. In one or more embodiments, the monitoring parameter update component 516 can employ one or more machine learning techniques to determine or infer, based on information included in the historical healthcare delivery information 148 and/or the information provided in the one or more healthcare information sources, one or more additional parameters for tracking via the tracking interface that are relevant to an identified significant event or condition.

In another example, the monitoring parameter update component 516 can determine one or more significant events over the course of care based on anticipated patient conditions or events. For example, the monitoring parameter update component 516 can determine using machine learning analysis of the historical healthcare delivery information 148 and/or the information provided in the one or more healthcare information sources 112, that based on occurrence of condition "ABC" at time $T_A$, condition "XYZ" is likely to occur at time $T_B$, (where time $T_B$ follows time $T_A$). The monitoring parameter update component 516 can further direct the interface component 518 to generate a new data field corresponding to condition "XYZ." In yet another example, the monitoring parameter update component 516 can direct the interface component 518 to add data fields to a tracking interface based on a predefined relationship between a data field selected for a patient care event or patient condition and other patient care events or patient conditions. For example, when a data field is added that corresponds to a patient care event "DEF," the monitoring parameter update component 516 can be configured to add one or more additional sub-data fields related to patient care event "DEF." These one or more sub-data fields can be determined by the monitoring parameter update component 516 using one or more of the machine learning techniques described herein.

In some embodiments, the AI evaluation component 136 can be configured to analyze a patient tracking interface based on data entered therein, a course of patient care, and a current point in time to facilitate determining or inferring clinical decisions associated with caring for the patient. For example, the AI evaluation component 136 can determine or infer when data is missing from a patient tracking interface regarding a patient care event or patient condition based on information learned from the historical healthcare delivery information and/or the information provided by the one or more healthcare information sources 112 regarding relationships between significant events or conditions, a course of patient care, a current point during the patient care, and the like. In response to a determination of missing data regarding a patient care event or patient condition, the tracking component 514 can call attention to a medical caregiver to perform the patient care event and/or check and enter information regarding the patient condition.

For example, the AI evaluation component 136 can determine or infer that based on a course of patient care and a current point in time, data should have been received regarding occurrence of patient care event "WRT." Accordingly, the AI evaluation component 136 can direct the notification component 510 and/or the tracking component 514 to notify a medical caregiver to perform patient care event "WRT" and enter data regarding performance of the patient care event. In another example, the AI evaluation component 136 can determine or infer that based on data received indicating patient care event "UYT" was performed, information regarding patient condition "345" should have been received. Accordingly, the AI evaluation component 136 can direct the notification component 510 and/or the tracking component 514 to notify a medical caregiver to check patient condition "345" and enter data regarding the patient condition. In yet another example, the AI evaluation component 136 can determine or infer that based on data indicating a patient condition has fallen below an unsatisfactory level, information regarding performance of a patient care event "JHG" should have been received. Accordingly, the AI evaluation component 136 can direct the notification component 510 and/or the tracking component 514 to notify a medical caregiver to perform patient care event "JHG" and enter data regarding performance of the patient care event.

In another aspect, the AI evaluation component 136 can determine or infer issues associated with a patient condition based on relationships between patient care events and/or patient care conditions, a course of patient care, and a current point during the patient care. For example, the AI evaluation component 136 can analyze data entered into a patient tracking interface and infer or determine that based on the collective information, the patient is in an unsatisfactory state. For instance, the AI evaluation component 136 can determine or infer that based on data regarding various vital signs of the patient and/or the infant and information indicating drug "XCR" was administered, the patient should be responding in a different manner. In response to a determination of an unsatisfactory patient state based on data received or entered into a patient tracking interface, the AI evaluation component 136 can direct the notification component 510 and/or the tracking component 514 to call attention to a medical caregiver and notify the medical caregiver of the unsatisfactory state of the patient and the basis for the determination that the patient is in an unsatisfactory state.

The tracking component 514 can employ various techniques to notify a medical caregiver regarding missing data from a patient tracking interface and/or regarding an issue associated with a state or condition of the patient. For example, the tracking component 514 can cause the interface component 518 to highlight a data field/row or cell associated with missing information to call attention of the medical caregiver to that data field/row and indicate that information is missing therefrom. In another example, the interface component 518 can cause the data field/row or cell to flash. In an aspect, when the missing information is associated with a patient care event or patient condition for which a data field/row is not provided in the patient tracking interface, the monitoring parameter update component 516 can instruct the interface component 518 to create or add the data field/row.

In another example, the tracking component 514 can facilitate sounding an alarm to notify a medical caregiver regarding missing data from a patient tracking interface and/or regarding an issue associated with a state or condition of the patient. In yet another example, the tracking component 514 can direct the notification component 510 to send a notification message to the medical caregiver (e.g., in the form of an electronic message such as a text message, an email, or other form of electronic message) regarding missing data from a patient tracking interface and/or regarding an issue associated with a state or condition of the patient.

In some embodiments, the live healthcare delivery guidance module 132 can further include security component 520 to police access of monitored patient information to only authorized clinicians. For example, the security component 520 can be configured to restrict access to a patient tracking interface and/or restrict devices/users from which information can be received for input into a patient tracking interface. For example, security component 520 can provide an authentication/authorization mechanism that allows only authorized users (medical staff) to access and/or manipulate data associated with a patient tracking interface (e.g., GUI 600 and the like).

FIGS. 7A-7E present an example patient tracking interface 700 (capable of being generated by the tracking component 514 and/or the interface component 518) as it evolves from a default shell or form over a course of patient care in accordance with various aspects and embodiments described herein. Although the example patient tracking interface 700 demonstrates tracking patient care events and conditions associated with a course of labor, it should be appreciated that various aspects of the interfaces described herein can be employed to track other type of patient care scenarios. Further, it should be appreciated that the patient care events and conditions monitored in these example interfaces are not intended to limit the scope of possible patient care events and conditions that can be monitored via the subject patient tracking tool. In particular, a data field provided in a row of the interfaces described herein can be adapted to correspond to any possible patient care event or condition associated with a course of labor. In addition, one or more of the data fields provided in the respective interfaces can be removed and/or additional data fields can be added. Repetitive description of like elements employed in respective embodiments of systems and interfaces described herein are omitted for sake of brevity.

With reference to FIG. 7A, the example patient tracking interface 700 is presented in shell form prior to reception of information regarding tracked events or conditions associated with a course of care of a patient. In the embodiment shown, the patient tracking interface 700 includes a plurality of compartments (e.g., the cells/compartments collectively identified by numeral 712) defined by a first axis 710 having columns corresponding to sequential periods (e.g., 4 hour periods) of time over the course of patient care and a second axis 708 having one or more rows respectively corresponding to one or more patient care events or patient conditions. Row 702 corresponds to admittance of the patient. Rows 704 and 706 include undefined fields. In an aspect, a user can select row 704 and/or row 706 to define a data field for the row associated with a patient care event or patient condition. It should be appreciated that any number N of data fields/rows can be added.

In an aspect, patient tracking interface 700 can be modified or configured to track any course of patient care that involves caring for a patient over a period of time. In some implementations, the data fields or rows can be fully or partially defined by a user. In other implementations, the data fields can be pre-defined for tracking a specific course of patient care (e.g., labor). According to this aspect, one or more of the data fields/rows can be preconfigured to represent a known patient care event and/or patient condition associated with the specific course of care. Still in other implementations, the specific data fields that are added to the patient tracking interface 700 over time can be determined automatically by the tracking component 514 to reflect one or more significant events or conditions identified by the significant event/condition identification component 138.

Still in yet another embodiment, one or more data fields/rows for addition to the patient tracking interface 700 can be determined by the monitoring parameter update component 516. For example, in response to addition/inclusion of a data field to the patient tracking interface 700 corresponding to a first patient care event or patient condition, one or more additional sub-data fields related to or dependent on the first patient care event or condition can be automatically added to patient tracking interface 700. In another example, in response to receipt of data associated with an occurrence and/or a characteristic of a first patient care event or patient condition, one or more additional sub-data fields related to the occurrence or the characteristic of the first patient care event or condition can be added. For instance, if a patient has a temperature above X degrees, based on known factors related to the patient and the course of care, an appropriate medical response can include administration of drug Y. Accordingly, in response to received data indicating the patient has a temperature above X degrees, a data field corresponding to administration of drug Y can automatically be added to the patient tracking interface 700. Still in yet another example, one or more data fields can be automatically added to the patient tracking interface 700 in response to passage of various amounts of time in view of a course of patient care for which the interface can be configured to track. For example, in association with a particular course of care, after the patient has been admitted 8 hours, the patient should receive X and Y treatment. Thus, in response to passage of 8 hours following admittance, data fields for treatments X and Y can be added to the patient tracking interface 700 automatically (e.g., via interface component 518).

FIG. 7B depicts another exemplary embodiment of patient tracking interface 700 in association with usage thereof to track the course of care of a patient throughout labor. In the embodiment shown, the patient tracking interface 700 has been updated based on reception of information regarding patient conditions and events up to admittance of the patient for 8 hours. According to this embodiment, default data fields 704 and 706 have respectively been changed to data fields 714 and 716. Data field 714 corresponds to stages of labor and data field 716 corresponds to categories of labor. Stages of labor and categories of labor can include stages and categories of labor associated with a condition of the mother and/or the infant. For exemplary purposes, date input field 714 corresponding to stages of labor indicates a descriptive stage of a state associated with the infant and input field 716 corresponding to categories of labor indicates a descriptive category of a state associated with the mother. In an aspect, data fields 714 and 716 can be defined by a user. In another aspect, data fields 714 and 716 can be automatically created based on reception of information (monitored by the monitoring component 134 and/or determined by the AI evaluation component 136) indicating the patient has been admitted, and indicating the infant is currently in stage I, and the patient's condition reflects a category I of labor.

For example, in an aspect, upon admittance of the patient, information can be received indicating she has been admitted, has entered category I of labor and her infant can be in stage 1. This information can be entered by a medical caregiver. In response to entry of the information, color bars 718, 720 and 722 are respectively initiated or generated (e.g., by tracking component 514). Color bars 718, 720 and 722 are configured to represent timelines respectively indicating the amount of elapsed time following admittance of the patient, duration of time the infant can be in stage I, and duration of time the patient can be in category I of labor. In an aspect, color bar 718 can be configured to automatically continue horizontally (e.g., to the right) across the patient tracking interface 700 in response to passage of time until information can be received indicating the patient can be no longer admitted. Similarly, color bars 720 and 722 can also be configured to automatically continue horizontally (e.g., to the right) across the patient tracking interface 700 until new information can be received indicating the infant can be no longer in stage 1 or the patient can be in category I of labor, respectively.

FIG. 7C depicts another example embodiment of the patient tracking interface 700 in accordance with aspects and embodiments described herein. In an aspect, the embodiment shown in FIG. 7C is an extension of the patient tracking interface 700 following admittance of the patient for 12 hours. In the embodiment shown, the patient tracking interface 700 includes a new data field 724 corresponding to ROM. The patient tracking interface 700 further includes a new color bar 726 indicating that the patient's membranes ruptured following 8 hours of admittance (e.g., or sometime between 8 and 12 hours after admittance). In an aspect, data field 724 and color bar 726 was added to the patient tracking interface 700 based on user input defining and adding the data field and indicating that the patient's membrane ruptured at a the 8 hour time mark following admittance of the patient. In another aspect, data field 724 and color bar 726 was added to the patient tracking interface 700 in response to a determination (e.g., by the AI evaluation component 136) that the patient's membrane ruptured at a time between 8 and 12 hours of time following admittance of the patient (e.g., based on live feedback information 154).

As seen when comparing the progression of the patient tracking interface 700 from FIGS. 7A to 7C color bars 718, 720, and 722 have automatically (e.g., without additional user input) extended horizontally across the patient tracking interface 700 in response to passage of time. In an aspect, color bar 726 can be also configured to automatically continue horizontally (e.g., to the right) across the patient tracking interface 700 in response to passage of time until information can be received indicating the patient can be no longer admitted.

FIG. 7D depicts another example embodiment of the patient tracking interface 700 in accordance with aspects and embodiments described herein. In an aspect, the embodiment shown in FIG. 7D is an extension of the patient tracking interface 700 as shown in FIG. 7C following admittance of the patient for 20 hours. In the embodiment shown, the patient tracking interface 700 includes a new data field 728 corresponding to cytotec. The patient tracking interface 700 further includes a new color bar 730 indicating that the patient was administered cytotec between 16 and 20 hours following admittance and new color bar 606 indicating the patient has entered category II of labor. In an aspect, data field 728 and color bar 730 were added to the patient tracking interface 700 based on user input defining and adding the data field and indicating that the patient was admitted cytotec at the 16 hour time mark following admittance. In another aspect, data field 728 and color bar 730 were added to the patient tracking interface 700 in response to a determination (e.g., by the AI evaluation component 136 based on monitored live feedback information 154) that patient was administered cytotec between 16 and 20 hours following admittance. In addition, color bar 722 was capped and color bar 732 was initiated in response to receipt of new data indicating the patient has entered category II of labor.

As seen when comparing the embodiments of the patient tracking interface 700 from FIG. 7C to FIG. 7D, color bars 718, 726, 720, ad 722 have automatically (e.g., without additional user input) extended horizontally across the patient tracking interface 700 in response to passage of time. In an aspect, color bar 730 can be configured to automatically continue horizontally (e.g., to the right) across the patient tracking interface 700 in response to the passage of time until information can be received indicating the patient can be no longer being administered cytotec. Similarly, color bar 732 can be configured to automatically (e.g., to the right) continue across the patient tracking interface 700 in response to passage of time until information can be received indicating the patient can be no longer in category II of labor.

FIG. 7E depicts another embodiment of the patient tracking interface 700 in accordance with aspects and embodiments described herein. In an aspect, the embodiment shown in FIG. 7E is an extension of the patient tracking interface 700 from the embodiment shown in FIG. 7D following admittance of the patient for 24 hours. In the embodiment shown, the patient tracking interface 700 includes a new data field 734 corresponding to pitocin. The patient tracking interface 700 further includes a new color bar 736 indicating that the patient was administered pitocin between 20 and 24 hours following admittance and new color bar 738 indicating the infant has entered stage II. In an aspect, data field 734 and color bar 736 were added to the patient tracking interface 700 based on user input defining and adding the data field and indicating that the patient was admitted pitocin between 20 and 24 hours following admittance. In another aspect, data field 734 and color bar 736 were added to the patient tracking interface 700 in response to a determination (e.g., by the AI evaluation component 136 based on monitored live feedback information 154) that the patient was administered pitocin between 20 and 24 hours following admittance. In addition, color bar 720 was capped and color bar 738 was initiated in response to receipt of new data indicating the infant has entered stage II.

As seen when comparing the embodiments of the patient tracking interface 700 from FIG. 7D to FIG. 7E, the color bars 718, 726, 730, and 732 have automatically (e.g., without additional user input) extended horizontally across the patient tracking interface 700 in response to passage of time. In an aspect, color bar 736 can be configured to automatically continue horizontally (e.g., to the right) across the patient tracking interface 700 in response to the passage of time. Similarly, color bar 738 can be configured to automatically (e.g., to the right) continue across the patient tracking interface 700 in response to passage of time until information can be received indicating the infant can be no longer in stage II.

Figure 8C:
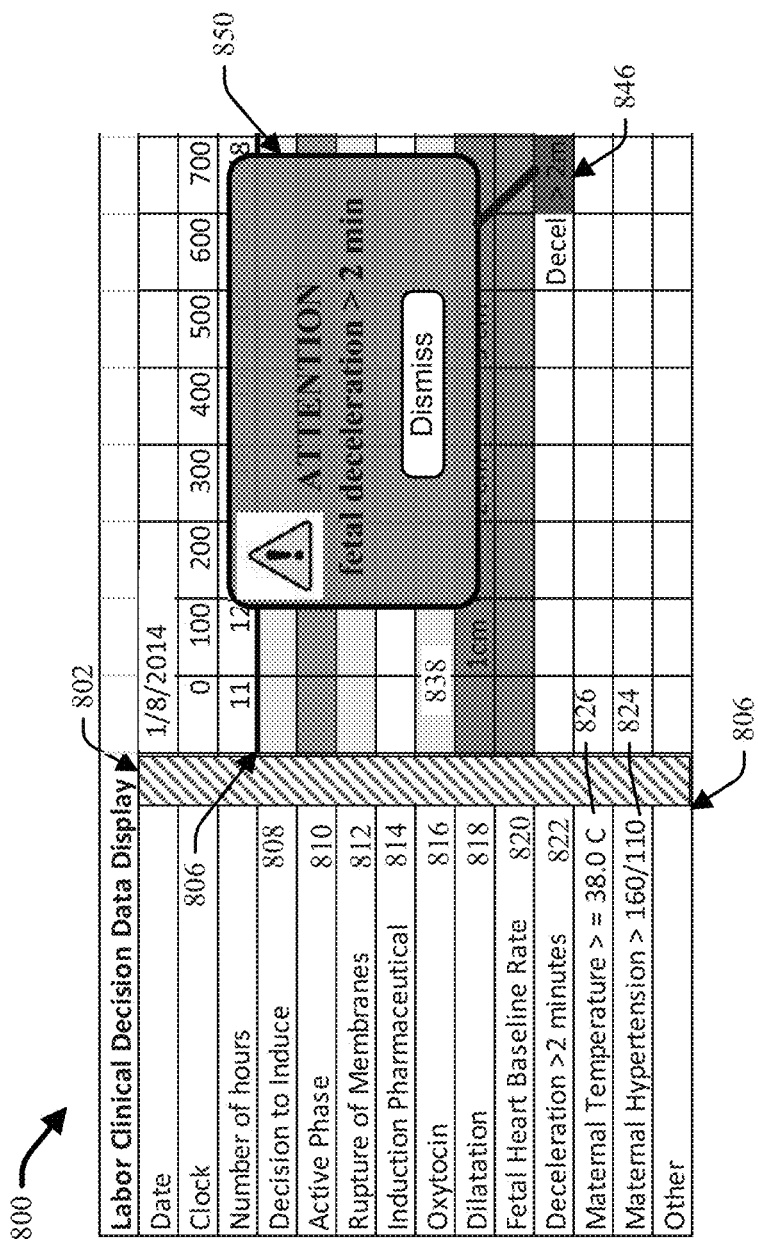

FIGS. 8A-8C present another example patient tracking interface 800 in accordance with aspects and embodiments described herein. Patient tracking interface 800 depicts a completed interface following tracking of a patient in labor over the course of 25 hours and two days. FIG. 8A includes information for the first day (Jan. 7, 2014) following admittance at time 1500 hours, and FIG. 8B includes information for the second day (Jan. 8, 2014). Interface 800 is divided over FIGS. 8A and 8B merely for lack of space due to restrictions in page dimensions. It should be appreciated that interface 800 can be displayed as a single continuous chart that can be displayed on one screen. In other implementations, the display window can include a sliding bar that allows a user to scroll through different parts of the interface 800 that do not fit entirely within the dimensions of a single window. Bar 802 correspond to a marker that indicate how interface 800 in FIG. 8A connects to interface 800 in FIG. 8B.

In the embodiment shown, interface 800 includes a plurality of compartments (defined by a first axis 804 having columns corresponding to sequential hours of time (in military time) and/or sequential hours passed, and a second axis 806 having a plurality of rows respectively corresponding to patient care events and patient conditions. Row 808 corresponds to a decision to induce. Data included in row 808 depicts the actual elapsed time from onset of induction. For example, grey color bar 828 marks the elapsed time following the decision to induce. In an aspect, grey color bar 828 moved horizontally across row 808 with each passing hour marked as a fixed point following initial data input indicating the decision to induce.

Row 810 corresponds to active phase. Data included in row 810 depicts the actual elapsed time from the beginning of the active phase of labor. For example, green color bar 830 marks the elapsed time following beginning of active phase. In an aspect, green color bar 830 moved horizontally across row 810 with each passing hour marked as a fixed point following initial data input indicating the beginning of active phase at time 2100. Row 812 corresponds to rupture of membranes. Data included in row 820 depicts the actual elapsed time following rupture of the membranes. For example, beige color bar 832 marks the elapsed time following rupture of membranes. In an aspect, beige color bar 832 moved horizontally across row 812 with each passing hour marked as a fixed point following initial data input indicating the rupture of membranes.

Row 814 corresponds to induction pharmaceutical. Data included in row 814 depicts blocks of time during which an induction pharmaceutical was administered. For example, yellow bar 834 indicates that a first dose of cytotec was administered beginning at time 1500 and ending at time 1700. Yellow bar 836 indicates a second dose of cytotec was administered beginning at time 2000 and ending at time 2400. In an aspect, various types of induction pharmaceuticals can be administered to a patient. Accordingly, text can also be included in association with data input to row 814 (e.g., the yellow fill) to indicate which induction pharmaceutical was administered. In an aspect, data field/row 814 can include a drop-down menu that can be displayed upon selection of data field/row 814 and provides options of induction pharmaceuticals to select from for ease of date entry. In another aspect, different induction pharmaceuticals can be associated with different fill colors.

Row 816 corresponds to oxytocin. Data included in row 816 depicts blocks of time during which oxytocin was administered. For example, grey bar 838 indicates that a first dose of oxytocin was administered beginning at time 2300 on Jan. 7, 2014 and ending at time 200 on Jan. 8, 2014. Grey bar 844 indicates a second dose of oxytocin was administered beginning at time 700 on Jan. 8, 2014. In an aspect, an oxytocin can be an intravenous drug that can be started and stopped multiple times during labor. Grey bars 838 and 844 can indicate blocks of time when the drug can be infusing. Text data indicating the "rate of infusion" can also be included in association with respective fill blocks indicating times when the drug can be infused. In an aspect, text data indicating rate of infusion can be included when the rate of infusion can be above a threshold rate (e.g., 20 or greater).

Row 818 corresponds to dilation. Data included in row 818 depicts blocks of time during which the patient was dilated. For example, pink color bar 840 indicates blocks of time during which the patient was dilated, beginning at 2300 on Jan. 7, 2014. Text data can be associated with fixed cells indicating a degree of dilation of the patient at the respective times associated with the cells (e.g., 1 cm, 2 cm, 3 cm, etc.).

Row 820 corresponds to fetal heart rate. Data included in row 820 depicts a measured baseline fetal heart rate that includes a fixed number of beats per minute. In an aspect, after the baseline fetal heart rate can be selected and/or entered, a color bar (e.g., blue color bar 842) can be initiated and moves across row 820 as time passes to indicate what the baseline fetal heart rate was.

Row 822 corresponds to deceleration of the fetal heart rate. Data included in row 822 can be entered in response to a deceleration of the fetal heart rate from the baseline fetal heart rate. For example, a color bar (e.g., red color bar 836) can be generated to indicate a fixed time or period during which the fetal heart rate decelerates. In an aspect, data can be entered in row 822 in response to deceleration of the fetal heart rate for a period greater than 2 minutes. Information indicating a total amount of time during which the fetal heart rate decelerated can also be included in associated with a fill color in row 822.

Row 824 corresponds to maternal temperature. Data included in row 824 can include a fixed color bar indicating a point in time or period during which the maternal temperature exceeded a threshold temperature (e.g., 38° C.). In an aspect, in response to entry of data in row 824, interface 800 can be configured to generate a pop-up display asking the caregiver if an antibiotic was administered. The caregiver can then provide additional input indicating whether an antibiotic was administered or not and what type of antibiotic was administered if an antibiotic was administered. In an aspect, this additional information can be associated with the color block included in row 824 associated with the spike in temperature. In another aspect, in response to an indication that an antibiotic was administered, interface 800 can generate an additional data field/row corresponding to the antibiotic and information regarding administration of the antibiotic can be included in this new data field/row.

Row 828 corresponds to maternal hypertension or blood pressure. Data included in row 828 can include a fixed color bar indicating a point in time or period during which the maternal blood pressure (e.g., systolic or diastolic) increased or decreased with respect to threshold values. In an aspect, in response to a second increase in blood pressure above a threshold value, interface 800 can be configured to generate a pop-up display asking the caregiver if intravenous magnesium has been started. The caregiver can then provide additional input indicating whether intravenous magnesium was administered or not. In an aspect, this additional information can be associated with row 828 where data can be provided indicating the rise in blood pressure. In another aspect, in response to an indication that intravenous magnesium was started, interface 800 can generate an additional data field/row corresponding to intravenous magnesium and a color bar can be generated in this additional data field/row indicating the amount of time intravenous magnesium was provided.

FIG. 8C presents an embodiment of patient tracking interface 800 including a notification 850 regarding a significant event or condition reflected in the data tracked by the patient tracking interface 800. In the embodiment shown, the current point in time associated with the course of labor being track is hour 700 on Jan. 8, 2014. The notification 850 calls attention to the fact that a fetal deceleration greater than 2.0 minutes has occurred. With reference to FIGS. 8C and 5, in one or more embodiments, notification 850 provides an example notification generated by the notification component 510 in response to a determination that the significant event involving the occurrence of a fetal deceleration greater than 2.0 minutes (e.g., as determined by the significant event/condition identification component 138) warrants sending a notification requiring acknowledgment by a clinician involved in the patient's care (e.g., the attending physician). For example, in one implementation, the risk/severity component 140 can have determined that a fetal deceleration greater than 2.0 minutes is a high risk/severity event and associate a high risk/severity score with the event (e.g., relative to a defined scale representative of varying degrees of risk). According to this example, the notification component 510 can be configured to generate a notification such as notification 850, for any event classified with a high risk/severity score (e.g., above a threshold score). The notification 850 also include a dismiss widget associated therewith. In one embodiment, the notification 850 can be configured to remain in the forefront of the display until it is positively acknowledged by an appropriate clinician, which can be assumed based on selection of the dismiss widget. In this regard, selection of the dismiss widget can result in provision of information to the acknowledgment component 512 indicating that the notification was acknowledged. The acknowledgment can further track information regarding the time when the acknowledgment was received, who (e.g., based on a device identifier) it was received from, and the like.

Figure 9:
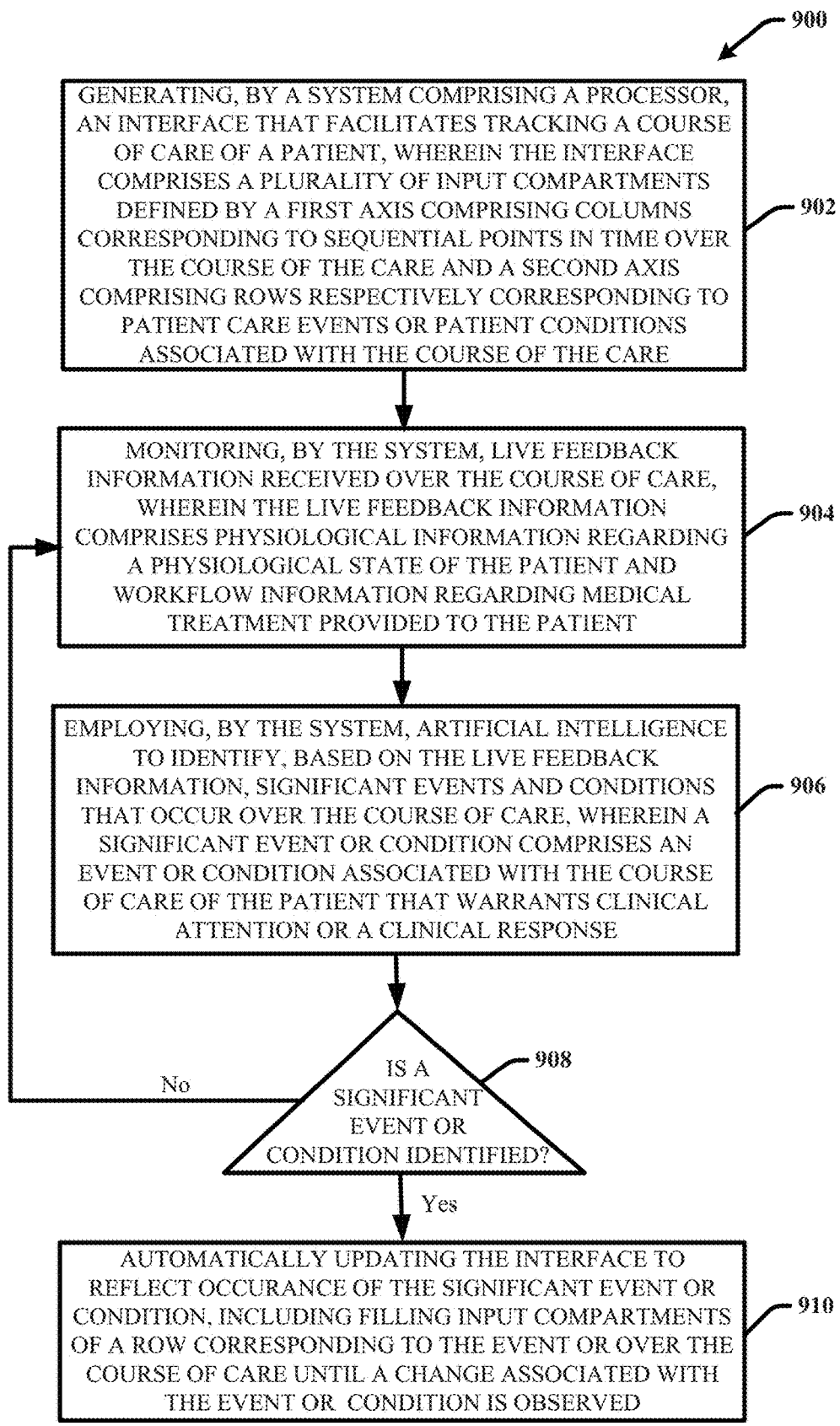
FIG. 9 illustrates a flow chart of an example method for tracking and displaying patient information over the course of care in accordance with various aspects and embodiments described herein.

FIG. 9 presents a flow diagram of an example method 900 for facilitating healthcare delivery using AI tactics in accordance with various aspects and embodiments described herein. Repetitive description of like elements employed in respective embodiments is omitted for sake of brevity.

At 902, a system comprising a processor (e.g., system 100, system 300 and the like), generates an interface that facilitates tracking a course of care of a patient (e.g., via interface component 518 and/or tracking component 514). The interface includes a plurality of input compartments defined by a first axis having columns corresponding to sequential points in time over the course of the care and a second axis having rows respectively corresponding to patient care events or patient conditions associated with the course of the care. At 904, the system monitors live feedback information (e.g., live feedback information 154) received over the course of care (e.g., via monitoring component 134), wherein the live feedback information comprises physiological information regarding a physiological state of the patient and workflow information regarding medical treatment provided to the patient. At 906, the system employs AI to identify, based on the live feedback information, significant events and conditions associated with the course of care of the patient, wherein a significant event or condition comprises an event or condition associated with the course of care of the patient that warrants clinical attention or a clinical response (e.g., via the AI evaluation component 136). At 908, the system determines whether a significant event or condition is identified. If not, the system continues to monitor the live feedback information. However, if at 908, a significant event or condition is identified, then at 910, the system automatically updates the interface to reflect occurrence of the significant event or condition, including filling input compartments of a row corresponding to the event or condition until a change associated with the event or condition is observed.

Figure 10:
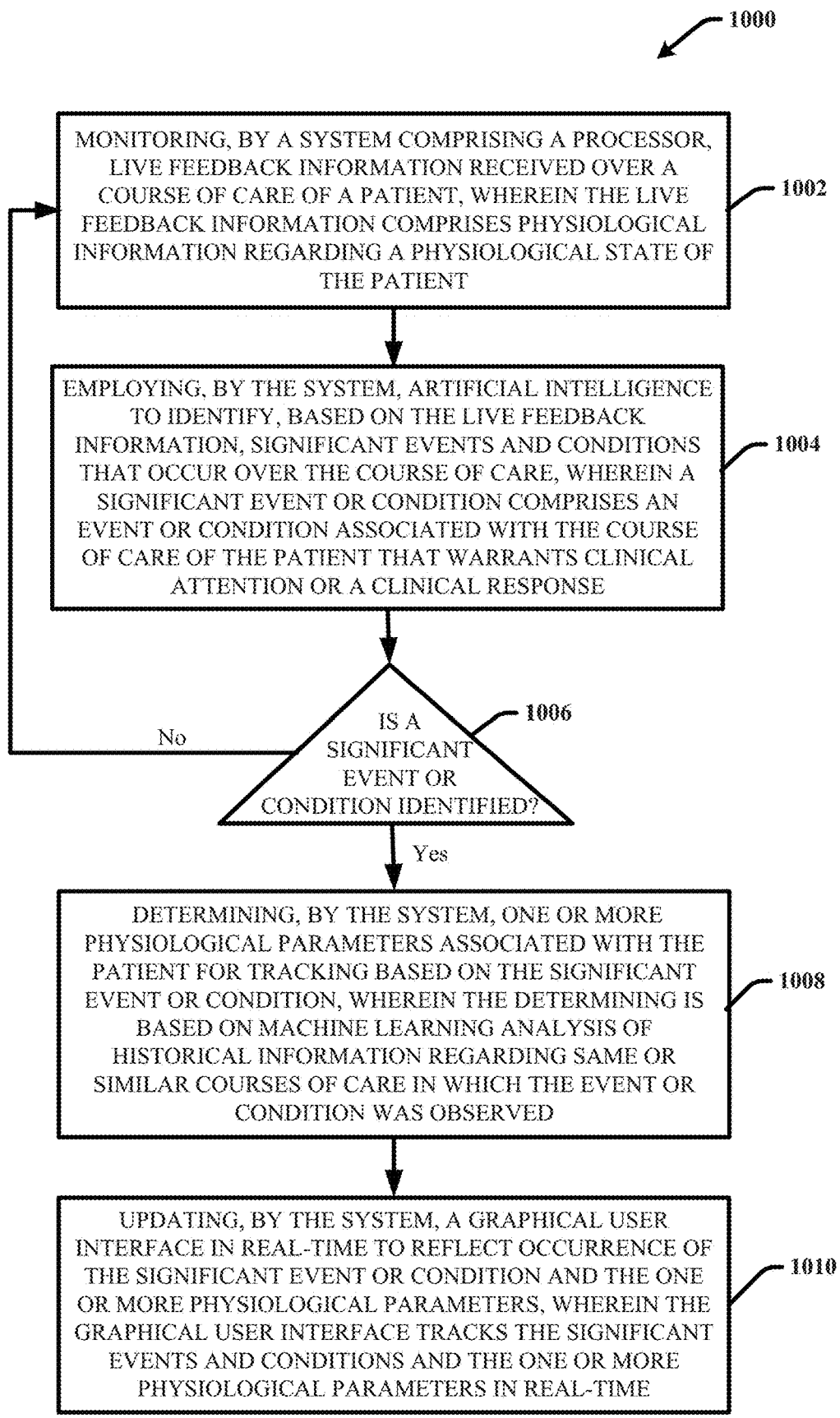
FIG. 10 illustrates a flow chart of another example method for tracking and displaying patient information over the course of care in accordance with various aspects and embodiments described herein.

FIG. 10 presents a flow diagram of an example method 1100 for facilitating healthcare delivery using AI tactics in accordance with various aspects and embodiments described herein. Repetitive description of like elements employed in respective embodiments is omitted for sake of brevity.

At 1002, a system comprising a processor (e.g., system 100, system 300 and the like) monitors live feedback information (e.g., live feedback information 154) received over a course of care of a patient (e.g., via monitoring component 134), wherein the live feedback information comprises physiological information regarding a physiological state of the patient. At 1004, the system employs AI to identify, based on the live feedback information, significant events and conditions associated with the course of care of the patient, wherein a significant event or condition comprises an event or condition associated with the course of care of the patient that warrants clinical attention or a clinical response (e.g., via the AI evaluation component 136). At 1006, the system determines whether a significant event or condition is identified. If not, the system continues to monitor the live feedback information. However, if at 1006, a significant event or condition is identified, then at 1008, the system determines one or more physiological parameters associated with the patient for tracking based on the significant event or condition (e.g., via monitoring parameter update component 516), wherein the determining is based on machine learning analysis of historical information regarding same or similar courses of care in which the event or condition was observed. Then at 1010, the system updates a GUI in real-time to reflect occurrence of the event or condition and the one or more parameters, wherein the GUI tracks the events and conditions and the one or more parameters in real-time (e.g., via the interface component 518 and the tracking component 514).

Figure 11:
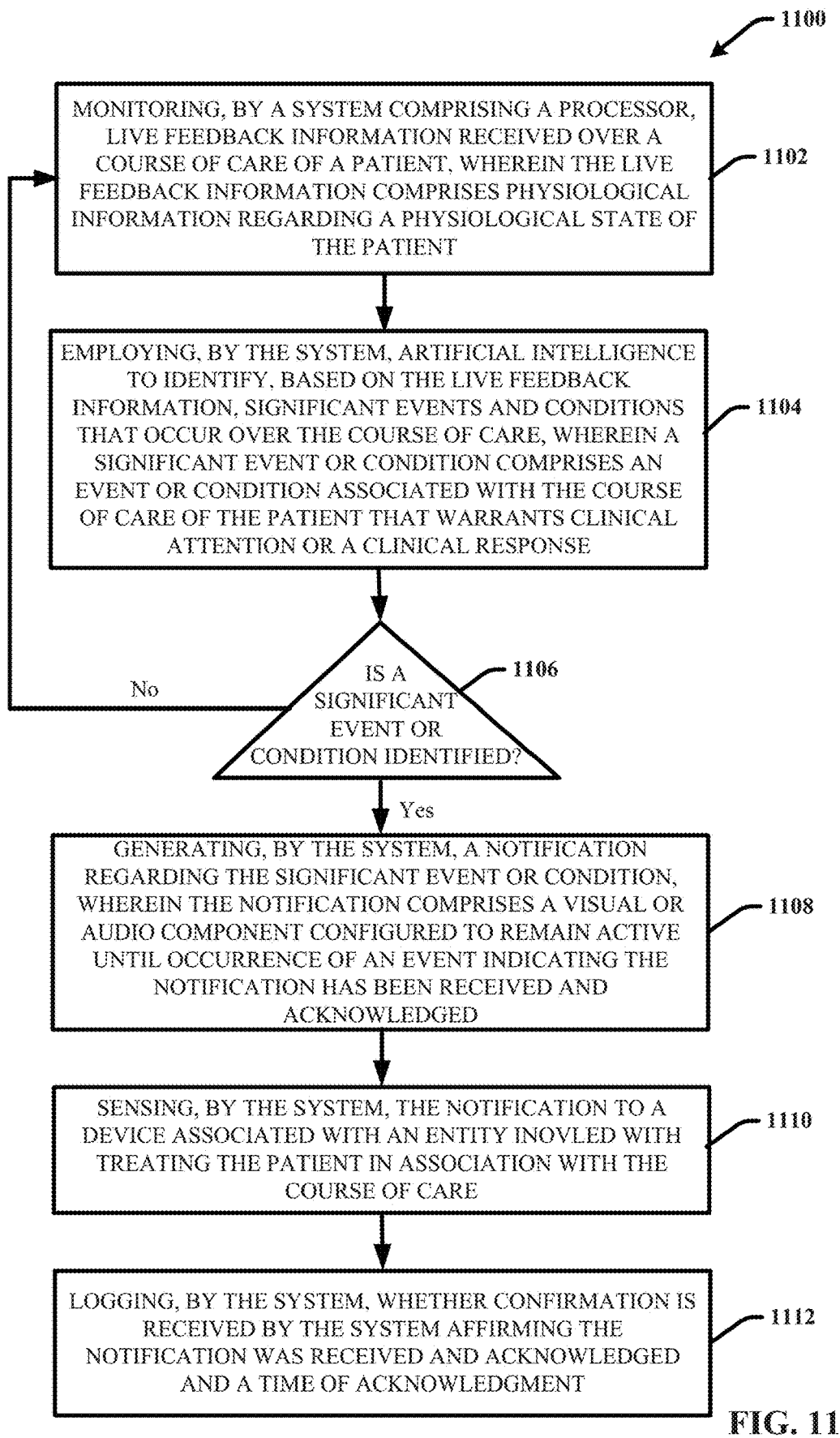
FIG. 11 illustrates a flow chart of an example method for ensuring recognition and acknowledgment of significant conditions or events associated with a course of patient care in accordance with various aspects and embodiments described herein.

FIG. 11 illustrates a flow chart of an example method 1100 for ensuring recognition and acknowledgment of significant conditions or events associated with a course of patient care in accordance with various aspects and embodiments described herein.

At 1102, a system comprising a processor (e.g., system 100, system 300 and the like) monitors live feedback information (e.g., live feedback information 154) received over a course of care of a patient (e.g., via monitoring component 134), wherein the live feedback information comprises physiological information regarding a physiological state of the patient. At 1104, the system employs AI to identify, based on the live feedback information, significant events or conditions associated with the course of care of the patient, wherein a significant event or condition comprises an event or condition associated with the course of care of the patient that warrants clinical attention or a clinical response (e.g., via the AI evaluation component 136). At 1106, the system determines whether a significant event or condition is identified. If not, the system continues to monitor the live feedback. However, if a significant event or condition is identified, then at 1108, the system generates a notification regarding the event or condition, wherein the notification comprises a visual or audio component configured to remain active until occurrence of an event (e.g., dismissing the pop-up notification) indicating the notification has been received and acknowledged (e.g., via notification component 510). At 1110, the system sends the notification to a device associated with an entity involved with treating the patient in association with the course of care (e.g., via notification component 510). Then at 1112, the system logs whether confirmation is received by the system (e.g., via acknowledgment component 512) affirming the notification was received and acknowledged and a time of acknowledgement.

FIG. 12 presented is another example embodiment of the live healthcare delivery guidance module 132 in accordance with various aspects and embodiments described herein. Repetitive description of like elements employed in respective embodiments is omitted for sake of brevity.

With reference to FIGS. 1 and 12, as discussed supra, the AI response component 142 can be configured to determine or infer and provide one or more responses to a significant event or condition identified by the significant event/condition identification component 138 based on the monitored live feedback information 154. For example, some appropriate responses discussed supra can include generating and sending a notification concerning an identified significant event or condition, requiring an entity to provide feedback acknowledging the notification, and/or tracking one or more parameters associated with the significant event or condition tracking a parameter associated with the clinically significant event or condition, and determining a new parameter for tracking that is related to the significant event or condition and automatically beginning tracking of the new parameter. In the embodiment shown, the AI response component 142 further includes prioritization component 1202, prioritization adaptation component 1204 (as part of the interface component 518), response recommendation component 1206, conference component 1208, polling component 1210, step-by-step guidance component 1212, and order authorization component 1214, to provided various additional responses based on identification of a significant event or condition by the significant event/condition identification component.

In one or more embodiments, the prioritization component 1202 can be configured to evaluate the significant events and/or conditions associated with a patient, procedure, clinical scenario, and the like, to determine a priority order of the significant events and conditions. Further, with respect to significant events or conditions that warrant a clinical response (e.g., provision of medical treatment to the patient), the prioritization component 1202 can also determine a priority order of the clinical responses. For example, with respect to a patient undergoing labor, as discussed supra, several different key data points and events/conditions associated with the mother and the infant can arise over the course of labor. Many of these key data points reflect significant events or conditions associated with the mother and/or the infant that occur simultaneously or concurrently. According to this example, some of the events or conditions may be more significant than others with respect to either a need for monitoring the event/condition, noting the time elapsed since occurrence of the event/condition, and/or providing a clinical response to the event or condition. In this regard, the prioritization component 1202 can be configured to employ one or more machine learning algorithms to evaluate the significant events and conditions detected for a patient to determine a priority order of the significant events and conditions. In some embodiments, the prioritization component 1202 can be configured to determine a priority order for only the significant event/conditions associated with a patient that are relevant to the current point in time. In this regard, the prioritization component 1202 can be configured to determine a priority order for events/ conditions that are concurrently occurring at the present point in time. In other embodiments, the prioritization component 1202 can be configured to determine a priority order for both past and present significant event/conditions detected for a patient.

In one or embodiments, the prioritization component 1202 can determine the priority order of the respective event/conditions based on one or more parameters including but not limited to: a time of occurrence of the significant event/condition, whether the significant event/condition is ongoing, a level of risk/severity associated with the significant event/condition (e.g., as determined by the risk/severity component 140), whether the significant event/condition warrants a clinical response, the type of the clinical response, a level or risk/severity associated with the clinical response, and a time at which the clinical response should be performed. For example, the prioritization component 1202 can evaluate the historical healthcare delivery information 148 and/or information provided by the one or more healthcare information sources 112 using one or more machine learning algorithms to determine a level of priority to associate with the respective events and conditions (e.g., past and present) associated with a current patient based on one more of these parameters. In this regard, the prioritization component 1202 can determine a priority level or score for the respective events/conditions and sort or rank the events/conditions according to their priority score (e.g., wherein events or conditions are listed in an ascending order of priority).

In some embodiments, the prioritization component 1202 can apply different weights to the one or more factors used to determine a priority level of an event or condition associated with a patient relative to other event/conditions (e.g., past and present) associated with the patient. For example, in some embodiments, if an event or condition requires a clinical response, this parameter can have more weight and thus increase the priority level or score of the event or condition relative to a parameter representative of the event or condition requiring monitoring. In one implementation, the weights applied to the respective parameters can vary based on the clinical scenario affecting the patient. For example, the weights applied to the respective parameters used for determining a priority level of an event/ condition associated with a patient can vary based on a condition/diagnosis of the patient, a procedure being performed, and the like.

Further, in some embodiments, the live healthcare delivery guidance module 132 can monitor, manage and guide healthcare delivery for many different patients, procedures, clinical scenarios, etc., occurring at the healthcare organization simultaneously. With these embodiments, the prioritization component 1202 can further be configured to compare events and/or conditions associated with two or more patients, and determine a priority order of the events and/or conditions associated with the two or more patients. In this regard, the prioritization component 1202 can determine in real-time, what patient of the two or more patients is highest priority and should be addressed first based on the priority level of the event/conditions currently associated with all patients. For example, with respect to a clinician attending to several patients in labor, the prioritization component 1202 can determine which patient at any point in time is associated with a highest priority event/condition relative to the other patients. The notification component 510 can further provide the clinician with feedback informing the clinician which patient to address first based on the priority level of the respective events/conditions affecting all patients.

In the embodiment shown, the interface component 518 can further include prioritization adaptation component 1204 to provide for adapting a patient tracking interface to display information representative of tracked events and conditions in a manner determined based on the priority of the events and conditions. For example, the interface component 518 can be configured to generate and provide various formats or types of patient tracking interfaces in addition to those presented with reference to FIGS. 6-8C. For example, with respect to a single patient, the interface component 518 can be configured to generate a visualization with various visual objects (e.g., blocks, elements, shapes), etc. representative of different patient events or conditions associated with a patient. In some implementations, these visual elements can be arranged in accordance with a timeline representative of an order of occurrence. In other implementations, these visual elements can be arranged in a manner that reflects their priority order. For example, in one embodiment, the visual elements can be arranged in three-dimensions, wherein visual elements corresponding to higher priority event/conditions can be positioned in the forefront of the view while lower priority events/conditions can be presented in the distance. According to this example, a clinician can easily look at the visualization to determine what event/conditions associated with the patient are of highest priority at the current point in time based on their location/arrangement in the GUI. The prioritization adaptation component 1204 can be configured to dynamically adapt these visual elements based on the current priority levels of the event/conditions that they respectively represent.

Further, in implementations in which multiple patients are being monitored, the respective patients can be associated with different windows or global visual elements in a tracking interface. The prioritization adaptation component 1204 can further dynamically adapt and arrange the positions of the different windows or global visual elements in the tracking interface to reflect the priority order of the different patients as determined based on the priority levels of the events/conditions associated with the different patients.

In some embodiments, a significant event or condition identified by the significant event/condition identification component 138 can prompt performance of an action or response by one or more clinicians, such as performance of a medical procedure, administration of a drug, application of pressure on a wound, ordering of an imaging study, ordering of a laboratory study, etc. In one or more embodiments, the response recommendation component 1206 can be configured to evaluate significant events and conditions identified by the significant event/condition identification component 138 to determine if the significant event or conditions warrants or requires a response or action for performance by one or more clinicians (e.g., including medical devices/machines). If a response or action is warranted, the response recommendation component 1206 can further determine what the response should be and recommend the response to one or more appropriate clinicians for performance. For example, the recommended response can be provided to one or more appropriate clinicians in the form of a visual notification including text identifying and/or describing the response, in the form of a spoken instruction, and the like. In some implementations, if a significant event or condition is associated with a recommended response, the notification component 510 can be configured to generate and provide a notification identifying the significant event or condition and including information describing the recommended response.

In some embodiments, response information identifying one or more known significant events or conditions that warrant a response by a clinician, and the response that should be performed, can be predetermined and accessible to the response recommendation component 1206 (e.g., in memory 128). For example, SOPs defined for various clinical scenarios, procedures, course of care, and the like can include information that defines how to respond to certain clinical events or conditions. In another example, many clinical reactions to certain patient conditions and events can be standard clinical reactions that generally apply to all patients, regardless of the medical history of the patient, the current physiological status of the patient, and the like. With these embodiments, the response recommendation component 1206 can employ the response information to determine whether an event or condition requires a response, and if so, what that response should be. The response recommendation component 1206 can further provide an appropriate clinician with information recommending the response.

However, in many clinical scenarios, whether a significant event or condition associated with a patient, procedure, clinical scenario, etc., warrants or requires a clinical response and/or if so, what the most appropriate response would be, varies based on the particular patient involved (e.g., including the medical history of the patient, the current state of the patient, the preferences of the patient, insurance of the patient, etc.), and many other contextual factors associated with the current clinical scenario, including factors related to clinicians (e.g., the capabilities, physiological/mental state, and availability of clinicians to perform the response, the timing at which the clinician will be available to perform the response, etc.), the state and availability of resources at the healthcare facility, and the like. In this regard, whether a response is necessary, and if so, the best response to a significant event or condition will vary based on many contextual factors involved, including factors specific to the patient, the clinicians, the resource available and/or the context of the clinical facility as whole. Further, there may be many possible actions or responses that can be performed in response to a significant event or scenario that can result in a positive outcome. Accordingly, in one or more embodiments, in addition to employing response information identifying known significant events or conditions that warrant responses and/or the known responses to be performed, the response recommendation component 1206 can employ AI to facilitate evaluating the many context specific factors associated with a current clinical scenario to determine or infer whether a clinical response (e.g., a response involving performance of an action by one or more clinicians) to an identified significant event or condition is appropriate, and if so, what that response should be. For example, with respect to a patient in labor, based on the occurrence of a second fetal deceleration below a defined threshold (e.g., which can be a significant event identified by the significant event/condition identification component 138), the current state of the mother, the medical history of the mother, and based on previous patient care events and conditions leading up to the current point in time (e.g., including time elapsed associated with patient care events and conditions), the response recommendation component 1206 can determine that an emergency cesarean section (C-section) should be performed. The response recommendation component 1206 can further provide the attending physician with an urgent notification recommending performance of the emergency C-section.

In this regard, the response recommendation component 1206 can evaluate the significant event or condition and one or more contextual parameters associated with the clinical scenario for which the significant event or condition is based. These contextual parameters can include parameters related to, but not limited to: the current physiological state of a patient involved, preferences of the patient, the medical history of the patient (e.g., including the immediate history involving a course of care leading up to the occurrence of the significant event or condition), demographic characteristics of the patient, a pain level and pain tolerance level of the patient, one or more clinicians available to perform the response, a current workload/schedule of the one or more clinicians, performance capabilities of the one or more clinicians (e.g., including level of proficiency in performing the potential response, authorization to perform the potential response and the like), preferences of the one or more clinicians, physiological status of the one or more clinicians (e.g., level of fatigue, level of stress, etc.), resources available at the healthcare facility, status of the resources (e.g., in use, working/broken, etc.), and the like. Information regarding these contextual parameters can be included in and/or determined based on the live feedback information 154, as well as information included in the one or more healthcare information sources 112 (e.g., the EMR/EHR data 116, the HR data 120, and the inventory data 124).

In one or more embodiments, based on the one or more contextual parameters associated with a current significant event or condition associated with a patient in a current clinical scenario, the response recommendation component 1206 can employ one or more machine learning techniques to learn from same or similar clinical scenarios involving the same or similar significant events or conditions under similar contexts to determine or infer if a response is warranted and what the most appropriate response should be, based on information included in the historical healthcare delivery information 148 as well as information included in the one or more healthcare information sources 112. For example, the response recommendation component 1206 can employ one or more machine learning techniques to identify significant events and conditions included in the historical healthcare delivery information 148 and/or the information provided by the one or more healthcare information sources 112 (e.g., the SOP data and the medical literature 118) that prompt or prompted a response involving some type of clinical action. The response recommendation component 1206 can further learn correlations associated with performance of specific actions to specific events or conditions that result in a positive clinical/financial outcome. In this regard, the response recommendation component 1206 can learn specific actions that should be performed in response to certain significant events and conditions that result in a positive clinical and/or financial outcome. The response recommendation component 1206 can further learn hidden correlations between the context of events or conditions and a specific action performed in response to the event or condition under the specific contexts that resulted in a positive outcome. Accordingly, the response recommendation component 1206 can employ machine learning analysis of the historical healthcare delivery information 148 and the information provided by the one or more healthcare information sources 112 (e.g., the SOP data, the medical literature 118, etc.) to learn how to tailor appropriate response to the context of a current clinical scenario. For example, although performance of a particular surgical procedure may be the ideal response to a particular clinical condition, as defined by an SOP associated with the clinical condition, historical data involving responding to the clinical condition, medical literature 118 defined for the clinical condition, etc., the current context of the clinical scenario may not have the resources (e.g., skilled clinicians, medical instruments, etc.) to perform the particular surgical procedure for this patient. Accordingly, the response recommendation component 1206 can determine an alternative action for responding to the clinical condition. In this regard, based on determination that a significant even or condition warrants or requires performance of an action by one or more clinicians, the response recommendation component 1206 can evaluate contextual information regarding the current status of the patient, the medical history of the patient, the preferences of the patient, the clinicians available to perform the response, the capabilities of the clinicians, the fatigue level of the clinicians, the resource available, and the like to determine the best action for responding to the significant event or condition.

In some embodiments, the response recommendation component 1206 can determine whether a clinical response to an identified significant event or condition is warranted and, if so, what that response should be, using risk analysis. In this regard, the response recommendation component 1206 can determine that a response is warranted if failure to perform the response would result in a higher probability of an adverse clinical and/or financial outcome than performance of the response. In one or more embodiments, the response recommendation component 1206 can evaluate a significant event or condition to initially determine a distribution of potential responses based on one or more suggested responses to the same or similar events or conditions based on information included in the SOP data 114, in the medical literature 118, and/or based on historical responses to same or similar significant events or conditions that have been known to result in a positive clinical and/or financial outcome.

The response recommendation component 1206 can further evaluate the potential responses based on the current context of the clinical scenario (e.g., in view of the various context based parameters discussed herein). For example, in some implementations, the response recommendation component 1206 can filter the list of potential responses based on the context of the current clinical scenario. According to this example, responses that could not be performed based on restrictions associated with the current clinical scenario (e.g., a comorbidity of the patient, a negative interaction with another drug the patient is taking, an unavailability of necessary resources, an unavailability of a qualified clinician to perform a procedure, etc.) can be removed. In another implementation, the response recommendation component 1206 can change or adjust one or more elements of one or more potential response (e.g., change a tool used, change a step involved, etc.) to fit the context of the current clinical scenario. In association with changing or adjusting one or more elements of a potential response, in some implementations, the response recommendation component 1206 can also determine information regarding the entity that can perform the response (e.g., the most capable clinician among the available clinicians), and the timing of performance of the action.

The response recommendation component 1206 and/or the risk/severity component 140 can further perform a cost/risk analysis with respect to the remaining and/or adjusted potential responses. This cost/risk analysis can involve determining a level of cost/risk associated with not responding to the current significant event or condition. This cost/risk analysis can evaluate both the clinical and financial cost attributed to not performing any response. For each of the remaining and/or adjusted potential responses, the response recommendation component 1206 and/or the risk/severity component 140 can further determine a level of risk/cost associated with performing the response. This risk analysis can consider correlations between available clinicians, capabilities of the available clinicians, current physiological states and workloads of available clinicians, resources available and the like. In this regard, clinician performance can vary based on context, fatigue, type of tasks performed, the way different combinations of clinicians work together to achieve a result (e.g., a group of clinicians that work in harmony or disagreement with one another), and the like. Accordingly, the level of risk associated with a recommended response can vary based on hidden correlations associated with variable clinician performance capabilities, habits, tendencies and the like.

In some embodiments, the response recommendation component 1206 can determine to perform a response to a significant event or condition if at least one of the potential responses is attributed to a lower level or risk/cost than not performing any response at all. Further, if two or more potential responses are attributed to a lower level of cost/risk compared to performing no response at all, in some implementations the response recommendation component 1206 can recommend the two or more responses and allow the clinician to decide which response to perform. In association with providing two or more recommended responses, the response recommendation component 1206 can include information regarding the risk/cost associated with the respective responses. In another implementation, the response recommendation component 1206 can select the response among the potential responses that minimizes the risk/cost. It can be appreciated that some suitable responses may be associated with a higher level of financial cost/risk but a lower level of clinical cost/risk (e.g., pertaining to the clinical outcome of the patient and the impact on the outcome relative to the patient's quality of life), and vice versa. In some embodiments, the response recommendation component 1206 can be configured to favor reducing clinical cost/risk over financial cost/risk, or vice versa.

In various embodiments, in addition to monitoring and recording acknowledgment of a notification that notifies the occurrence of a significant event or condition, the acknowledgment component 512 can also be configured to monitor and record acknowledgment of notifications including one or more recommended responses to an identified significant event or condition. The way the acknowledgment component 512 receives acknowledgment of a recommended clinical response to a significant event or condition can be the same or like that discussed with reference to general notifications. In some embodiments, in association with responding to a recommended response, a clinician can provide feedback indicating that they either will or will not perform the recommended response. In some embodiments, if a clinician choses to forgo performing a recommended response, the clinician can be held personally responsible in the event a complication arises. For example, the notification including the recommended response can inform the clinician that failure to follow the recommended response will result in acceptance of personal liability (e.g., as opposed to coverage under the healthcare organizations insurance policy) for attributed complications. In another example implementation, the response recommendation component 1206 can trigger acceptance of personal liability for failure to perform recommended responses associated with a high cost/risk level. In this regard, the response recommendation component 1206 can trigger personal liability for failure to perform a recommended response only in situations where failure is attributed to a cost/risk level above a threshold cost/risk level (and/in some implementations in which the recommended response reduces the cost/risk level more than a defined percentage).

In various embodiments, the response recommendation component 1206 may not be able to determine whether a response to a significant event or condition is warranted and/or if so what the response should be, with sufficient accuracy. For example, the significant event or condition may be a rare event or condition for which little historical evidence is available. In another example, the significant event or condition may be associated with an unusual context, either related to the condition of the patient, the clinicians involved, the resource available, and the like. In these scenarios, using the cost/risk analysis discussed above, the response recommendation component 1206 may inaccurately determine that a response is not warranted either because the historical evidence, medical literature, SOP data and the like, does not recognize the event or condition and/or the historical evidence, medical literature, and/or SOP data does not recognize a response to the event or condition in the current context. In these scenarios, the response recommendation component 1206 may also determine that a response is warranted, but be unable to determine a response to recommend. Further, the response recommendation component 1206 may inaccurately recommend an inappropriate response (e.g., a response that leads to adverse an outcome).

Accordingly, in some embodiments, the response recommendation component 1206 can be configured to recognize scenarios in which the event or condition is unusual and/or the context of the event or condition is unusual. For example, the response recommendation component 1206 can determine that an event or condition in the current context is unusual based on the event or condition and context being excluded from the historical healthcare delivery information 148 and/or the information provided by the one or more healthcare information sources 112. In another example, the response recommendation component 1206 can determine that an event/condition and context is unusual based on low (e.g., with respect to a threshold) historical occurrence of the event/condition and context. The response recommendation component 1206 can further classify these types of events or conditions as rare or unusual. As discussed infra, the response recommendation component 1206 can be configured to employ the conference component 1208 and/or the polling component 1210 in these scenarios to further facilitate guiding clinicians when making clinical decisions about responding to such rare or unusual events/conditions and/or contexts.

The response recommendation component 1206 can also be configured to employ the conference component 1208 and/or the polling component 1210 in scenarios in which the cost/risk associated with not responding to a significant event or condition and/or the cost/risk associated with one or more potential responses is relatively high (e.g., with respect to a threshold). For example, in some scenarios, the cost/risk associated with failure to perform a response to an identified significant event or condition is high and the response recommendation component 1206 cannot determine an appropriate response (e.g., based on insufficient historical evidence and/or medical literature for the context associated with the clinical scenario). In another scenario, both the cost/risk associated with not performing a response and performing a recommended response may be high (e.g., relative to a threshold). In this regard, the difference in cost/risk associated with not performing a response and performing any of the potential responses may low (e.g., relative to a threshold). Accordingly, the response recommendation component 1206 can recognize that the confidence level that either choice is the correct choice is low. Thus, in scenarios in which cost/risk associated with not responding to a significant event or condition and/or the cost/risk associated with one or more potential responses is relatively high (e.g., with respect to a threshold), the response recommendation component 1206 can characterize these events/conditions as being associated with a high degree of sensitivity. The response recommendation component 1206 can further be configured to invoke the conference component 1208 and/or the polling component 1210 for events and conditions associated with a high degree of sensitivity to facilitate determining whether a clinician should respond to these events or conditions and if so, how to respond.

In this regard, the conference component 1208 can be configured to establish a live call (e.g., a voice and/or video call) with one or more clinicians that are remote from a current clinical scenario that is being facilitated by the live healthcare delivery guidance module 132 to receive live feedback from the one or more clinicians regarding the current clinical scenario. In this regard, the conference component 1208 can function as a direct automated help line to one or more expert or advisory clinicians that can remotely provide live assistance to one or more local clinicians in a current clinical scenario that need help. In one or more embodiments, the response recommendation component 1206 can be configured to automatically establish a call with one or more expert clinicians in response to a determination that an identified event or condition is rare or unusual and/or that the event or condition is associated with a high degree of sensitivity. In some implementations, in association with establishing the call, the conference component 1208 can brief the called clinicians regarding the clinical scenario and the current event or condition for which their expert advice is needed.

Further, in some embodiments, the conference component 1208 can employ AI to determine who to call. For example, the conference component 1208 can utilize information regarding the current clinical scenario, including information identifying the significant event or condition and various addition contextual parameters associated with the patient, the clinicians, the resources at the facility, and evaluate information regarding the past experiences of clinicians that were involved with treating patients in same or similar clinical scenarios (e.g., based on included in the HR data 120 and/or the historical healthcare delivery information 148). The conference component 1208 can further evaluate level of expertise, level of experience, level of proficiency in achieving positive outcomes, and the like (e.g., based on included in the HR data 120 and/or the historical healthcare delivery information 148). Accordingly, the conference component 1208 can determine one or a group of the most qualified clinicians to call for advice regarding the current clinical scenario based on proven evidence regarding their knowledge and experience in the relevant field.

The polling component 1210 can be configured to generate an instant poll regarding an unusual and/or sensitive (e.g., high cost/risk) event/condition associated with a clinical context. The poll can include a description of the clinical context, the event and/or the condition, and ask for advice regarding whether and how to respond. In some implementations, the poll can include two or more potential response options determined by the response recommendation component 1206 and ask for selection of a preferred response. The polling component 1210 can further send the poll to several skilled or expert clinicians that have relevant experience in the field. Like the conference component 1208, the polling component 1210 can also employ same or similar AI tactics to determine a group of the most qualified, knowledgeable and experienced clinicians in the field that are appropriate for providing advice for the unique and/or sensitive clinical scenario at hand. The polling component 1210 can further receive and collate the responses from the expert clinicians and provide the results to the one or more clinicians onsite that are responsible for responding to the significant event or condition. Accordingly, the polling component 1210 can automatically provide real-time collated opinions from specifically selected experts in the field regarding whether and how to respond to a current clinical scenario in situations when the local clinicians and the live healthcare delivery guidance module 132 are faced with uncertainty.

In addition to automatically identifying and calling attention to and/or providing recommended response to significant events or conditions that arise in various clinical scenarios, the live healthcare delivery guidance module 132 can also include step-by-step guidance component 1212 to provide step-by-step instruction regarding how to provide medical care in essentially any clinical scenario. In this regard, the step-by-step guidance component 1212 can essentially learn how to perform medical procedures, and how to treat patients in various clinical scenarios based on information included in the historical healthcare delivery information 148 and the one or more healthcare information sources 112. For example, in some embodiments, based on SOPs collated from various healthcare organizations that define protocols for performing a medical procedure or for responding to a clinical scenario, the step-by-step guidance component 1214 can determine an SOP that applies to a current clinical scenario, even when the SOP is borrowed from another institution, facility, etc. The step-by-step guidance module can further employ that SOP to guide a clinician in performing a procedure or responding to a clinical scenario that they have low or no experience in.

For example, in some implementations, a clinical scenario may arise that a clinician and/or healthcare facility has not had any or sufficient experience with addressing. However, given the urgency of the situation and/or the inability to bring in a more qualified clinician (e.g., based on time, location, cost, etc.). In this regard, the clinician may not know how to respond to certain scenarios, what to do, or how to interpret the feedback. In these embodiments, the step-by-step guidance component 1212 can aid in the clinical decision process by instructing the clinician what to do. For example, in one or more embodiments, the step-by-step guidance component 1212 can learn the SOPs for one or more healthcare organizations and/or facilities. The step-by-step guidance component 1212 can further receive a request from one or more clinicians requesting assistance in association with guiding healthcare delivery in a current clinical scenario. Based on reception of the request, the step-by-step guidance component 1212 can monitor delivery of healthcare care to a patient in real-time relative to the one or more SOPs applicable to the patient (e.g., an SOP that applies to a condition of the patient, an SOP that applies to a procedure being performed on the patient, and the like) based on received live feedback over the course of care. For example, the feedback can include information regarding monitored patient physiological states/conditions, information regarding workflow actions performed (or skipped) by respective clinicians for respective patients, and the like. Based on the monitored live feedback information 154 and the applicable SOPs, the step-by-step guidance component 1212 can determine the applicable SOPs, the step-by-step guidance component 1212 can instruct the one or more clinicians exactly what to do and when over the course or care. Accordingly, the step-by-step guidance component 1212 can guide clinical decisions in real-time to promote best practices and provide risk avoidance measures based on applicable SOPs.

In various implementations, the live healthcare delivery guidance module 132 can include order authorization component 1214 to facilitate automatically authorizing clinical decisions involving medical orders for clinical treatment. The medical orders can relate to essentially any clinical decision that warrants and/or requires pre-authorization based on the governing SOPs or rules of the healthcare organization. For example, the orders can relate to requests for imaging studies, laboratory studies, performance of certain clinical procedures, usage of certain pharmaceuticals, usage of certain medical supplies, and the like. The orders can be placed by clinicians in various roles with various levels of authorization with respect to making different clinical decisions. For example, many medical organizations can implement policies that require receiving authorization to perform actions that are costly, potentially outside a defined SOP for the clinical scenario, or otherwise not directed by the response recommendation component 1206. In this regard, a clinician may determine that an order for a medical study, procedure, instrument, etc., is necessary based on personal experience, expertise and interaction with the patient, even if the response recommendation component 1206 does not recommend the order or consider the order necessary. In these scenarios, time wasted and frustration dealing with the pre-authorization process can hinder the quality of care capable of being provided by the clinician to the patient and result in failure of achieving the most optimal clinical and financial result in hindsight.

In view of these scenarios, the order authorization component 1214 can employ machine learning to automatically evaluate various parameters associated with the time sensitivity of a submitted order, the level of risk/cost associated with the clinical scenario, and/or whether the clinical scenario is unusual/rare and/or highly sensitive, to automatically rule on whether to approve the order or not. In addition, the order authorization component 1214 can evaluate parameters related to the clinician that submitted the order to determine whether to approve or deny the order. For example, the order authorization component 1214 can look at the level of experience/expertise of the clinician, the duration of employment, the level of proficiency of the clinician in providing quality care in similar scenarios, ratings of the clinician from prior patients and colleagues, and the like. Accordingly, if the clinician has a track record for making the right decisions (in terms of clinical and/or financial outcome) in similar complex clinical scenarios, the order authorization component 1214 can automatically authorize the clinicians order, even if it may go against the SOP and/or recommended response suggested by the response recommendation component 1206.

Figure 13:
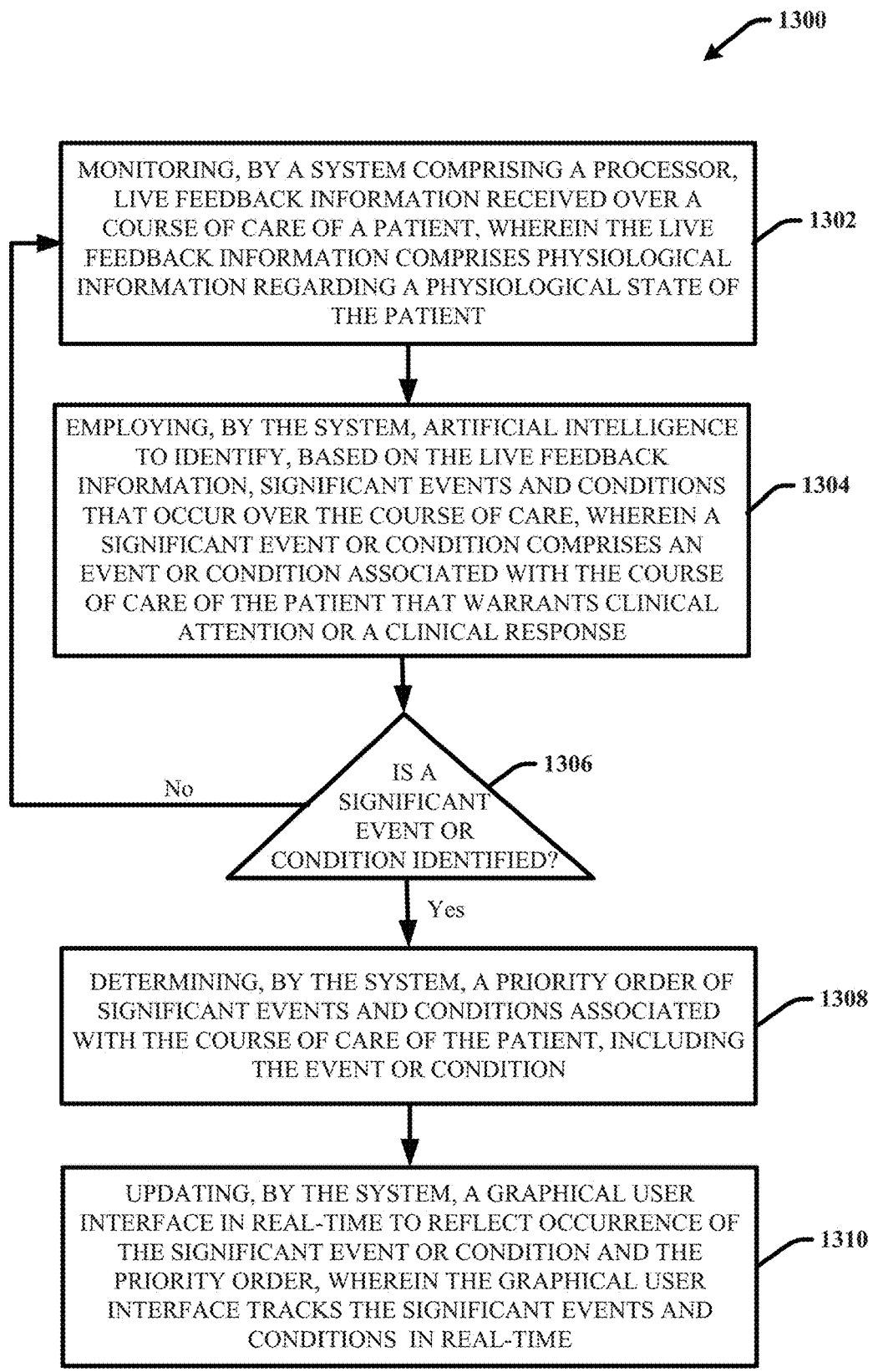
FIG. 13 presents a flow diagram of an example method for facilitating healthcare delivery using AI tactics in accordance with various aspects and embodiments described herein.

Referring now to FIG. 13, presented is a flow diagram of an example method 1300 for facilitating healthcare delivery using AI tactics in accordance with various aspects and embodiments described herein. Repetitive description of like elements employed in respective embodiments is omitted for sake of brevity.

At 1302, a system comprising a processor (e.g., system 100, system 300 and the like) monitors live feedback information (e.g., live feedback information 154) received over a course of care of a patient (e.g., via monitoring component 134), wherein the live feedback information comprises physiological information regarding a physiological state of the patient. At 1304, the system employs AI to identify, based on the live feedback information, significant events and conditions associated with the course of care of the patient, wherein a significant event or condition comprises an event or condition associated with the course of care of the patient that warrants clinical attention or a clinical response (e.g., via the AI evaluation component 136). At 1306, the system determines whether a significant event or condition is identified. If not, the system continues to monitor the live feedback information. However, if at 1306, a significant event or condition is identified, then at 1308, the system determines a priority order of events and conditions associated with the course of care of the patient, including the event or condition (e.g., via prioritization component 1202). Then at 1310, the system updates a GUI in real-time to reflect occurrence of the event or condition and the priority order, wherein the GUI tracks the events and conditions in real-time (e.g., via the interface component 518 and the prioritization adaptation component 1204).

Figure 14:
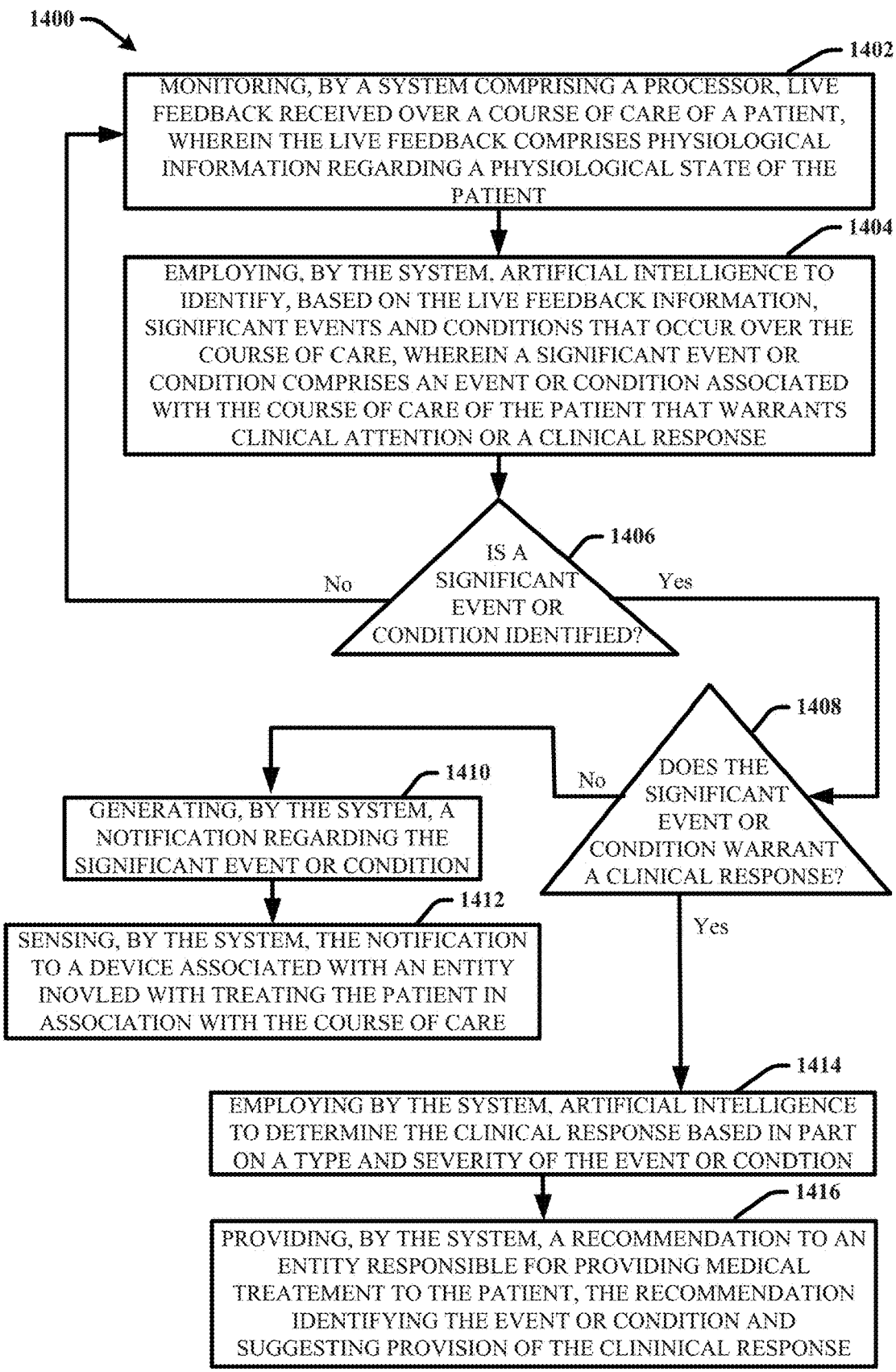
FIG. 14 presents a flow diagram of another example method for facilitating healthcare delivery using AI tactics in accordance with various aspects and embodiments described herein.

FIG. 14 presents is a flow diagram of another example method 1400 for facilitating healthcare delivery using AI tactics in accordance with various aspects and embodiments described herein.

At 1402, a system comprising a processor (e.g., system 100, system 300 and the like) monitors live feedback information (e.g., live feedback information 154) received over a course of care of a patient (e.g., via monitoring component 134), wherein the live feedback information comprises physiological information regarding a physiological state of the patient. At 1404, the system employs AI to identify, based on the live feedback information, significant events and conditions associated with the course of care of the patient, wherein a significant event or condition comprises an event or condition associated with the course of care of the patient that warrants clinical attention or a clinical response (e.g., via the AI evaluation component 136). At 1406, the system determines whether a significant event or condition is identified. If not, the system continues to monitor the live feedback. However, if a significant event or condition is identified, then at 1408, the system determines whether the significant event or condition warrants a clinical response (e.g., via the AI response component 138). If at 1408, the system determines the significant event or condition does not warrant a clinical response, then at 1410 the system generates a notification regarding the significant event or condition (e.g., via notification component 510), and at 1412, sends the notification to a device associated with an entity involved with treating the patient in association with the course of care. However, if at 1408, the system determines the significant event or condition warrants a clinical response, then at 1414 the system employs AI to determine the clinical response based in part on a type and severity of the event or condition (e.g., via the response recommendation component 1206). At 1416, the system further provides a recommendation to an entity responsible for providing medical treatment to the patient, the recommendation identifying the event or condition and suggesting provision of the clinical response (e.g., via the response recommendation component 1206 and/or the notification component 510).

Figure 15:
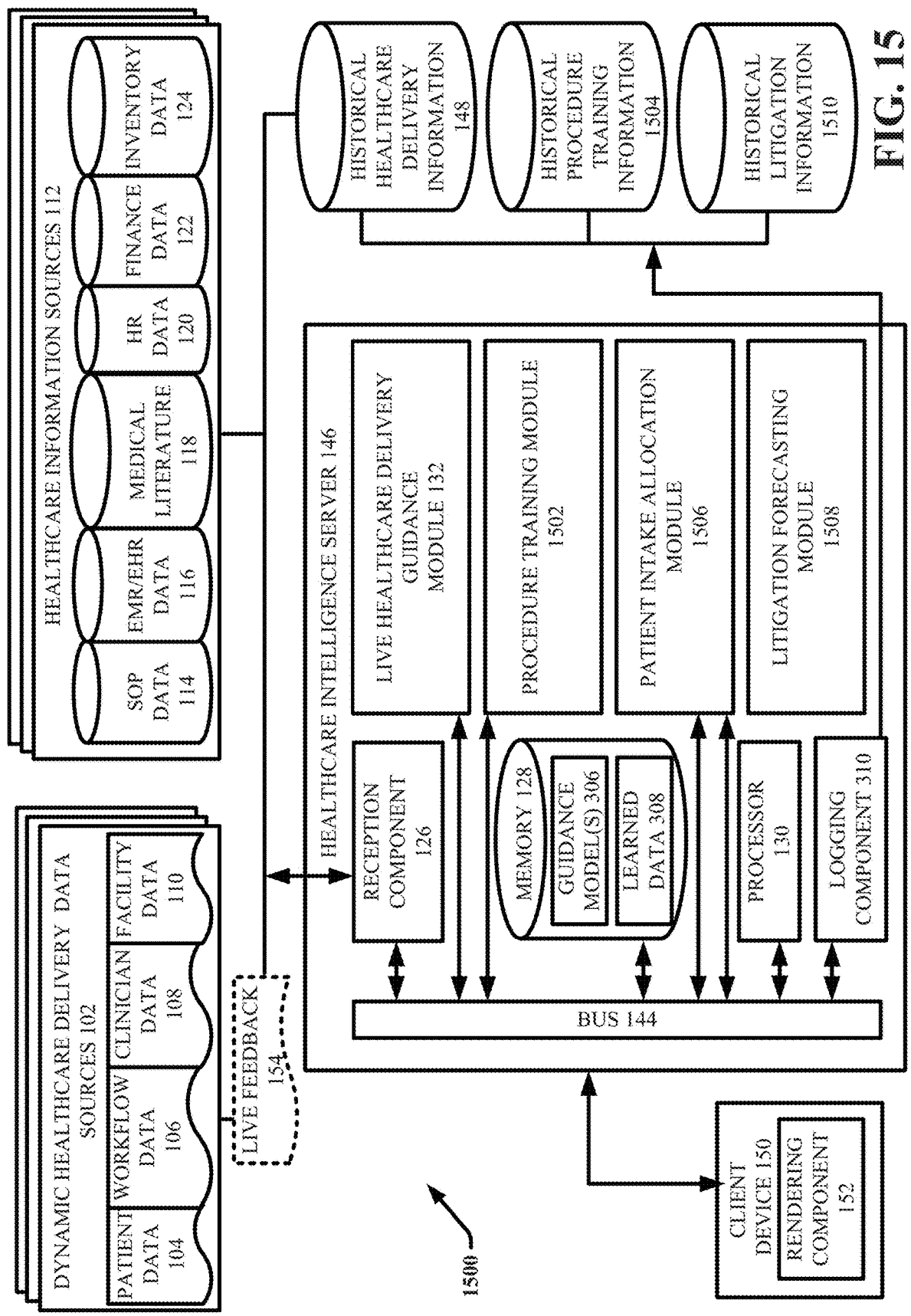
FIG. 15 illustrates another example system that facilitates developing and applying AI tactics to facilitate healthcare delivery in accordance with various aspects and embodiments described herein.

FIG. 15 illustrates another example system 1500 that facilitates developing and applying AI tactics to facilitate healthcare delivery in accordance with various aspects and embodiments described herein. System 1500 can include same or similar features and functionalities as system 100 and system 300 with the addition of some additional modules to the healthcare intelligence server 146, including procedure training module 1502, patient intake allocation module 1506, and litigation forecasting module 1508. System 1500 further includes historical procedure training information 1504 and historical litigation information 1510. Certain components or elements included in previous embodiments are omitted from system 1500 merely the sake of clarity and/or simplicity when explanations are not necessarily focused on the omitted components/elements. Repetitive description of like elements included in previous embodiments are omitted for the sake of brevity.

As discussed supra, in various embodiments, the live healthcare delivery guidance module 132 can employ machine learning analysis of the historical healthcare delivery information 148 and the information provided by the one or more healthcare information sources 112 to determine significant events and conditions associated with a clinical scenario, procedure, course of care, and the like, as well as appropriate clinical responses to the significant events and conditions. In this regard, the live healthcare delivery guidance module 132 can develop one or more guidance models 306 and/or learned data 308 for different clinical scenarios, procedures, courses of care and the like, that defines significant events and conditions associated therewith, appropriate responses to the significant events and conditions, and further correlates one or more parameters associated with patient data 104, workflow data 106, clinician data 108 and/or facility data 110 (e.g., parameters included in the live feedback information 154) used to identify the significant events or conditions. In one or more embodiments, the procedure training module 1502 can employ this information provided by the guidance models 306 and/or learned data 308, as well as SOP information for the clinical scenarios, procedures, courses of care, etc., (e.g., included in the SOP data 114), and historical healthcare delivery information 148 that records all aspects of past performed clinical scenarios, procedures, and courses of care, to develop and provide an interactive procedure training application for the respective clinical scenarios, procedures and courses of care. The interactive procedure training application can facilitate training a clinician and/or evaluating the clinician in association with performance of a particular clinical scenario, procedure, course of care, and the like, by providing the clinician with a simulated experience of the clinical scenario, procedure, or course of care. The interactive procedure training application can further monitor the clinician's performance over the course of the simulation to facilitate evaluating and training the clinician.

For example, in one embodiment, the procedure training module 1502 can develop and provide an interactive medical procedure simulation application that provides a clinician with information related to a hypothetical clinical scenario. The interactive application can further receive feedback from the clinician regarding their evaluation and/or clinical response (e.g., if a response is warranted) to the clinical scenario. The way the feedback is received can vary based on the medium via which the simulation is provided. For example, as discussed in greater detail below, in some implementations the feedback include user provided or selected answers to prompts asking the clinician to provide an evaluation and/or suggested response to a certain clinical scenario in association with an interactive software gaming type application. In other implementations, the feedback can also include monitored actions performed by the clinician in association with a virtual reality (VR) simulation in which the user performs actions via an avatar in a VR gaming application. In another implementation, the feedback can include actual physical actions performed by the clinician in an augmented reality environment.

The hypothetical clinical scenario can be based on an actual historical clinical scenario that occurred in the past (e.g., as included in the historical healthcare delivery information) or known exemplary clinical scenarios defined by SOP data 114 and/or in medical literature 118. The hypothetical clinical scenario can be related to a static event, a medical procedure that involves performance of several procedural steps, a course of care of a patient in association with a particular diagnosis or condition, and the like. For example, in some embodiments, the procedure training module 1502 can develop and provide an interactive training application that is directed to simulating an entire course of care of a patient admitted with a particular condition or diagnosis. In this regard, the procedure training module 1502 can develop and provide many different simulations, including simulations directed to various conditions and diagnosis. In another embodiment, the procedure training module 1502 can develop and provide interactive simulations that are directed to performing different types of medical procedures, different practice areas or specialties and the like.

For example, in some implementations, in association with simulating a clinical scenario, the interactive application can provide the clinician with the type of information included in the live feedback information 154. For example, in one implementation, the training application can provide a clinician with information regarding one or more physiological parameters and/or conditions of a patient and prompt the clinician to provide feedback regarding their evaluation and response of the patient current state, whether a clinical response is appropriate, and what that response should be. In various embodiments, the information provided describing the clinical scenario can focus on significant event or condition previously determined for and associated with the clinical scenario. For example, over a simulated course of care treating a patient undergoing labor, the simulation application can provide the clinician with information regarding physiological parameters, workflow parameters and the like that correlates to a known significant event or condition. According, the training application can train and evaluate a clinician's ability to recognize and respond appropriately to significant event or conditions known for a clinical scenario, procedure, course of care, and the like. In some implementations, the procedure training application can also provide the clinician with one or more contextual parameters related to the clinical scenario, such as contextual parameters associated with the patient (e.g., medical history information, preference information, demographic information, and the like etc.), associated with the clinician (e.g., level of fatigue), associated with the current state of a hypothetical environment at which the patient is being treated, and the like. Accordingly, the simulation of the clinical scenario can require the clinician to consider the many different variables (e.g., contextual parameter) associated with the hypothetical clinical scenario when providing feedback including an evaluation and/or recommended response to the clinical scenario.

The interactive medical procedure application can further monitor, and evaluate feedback provided by or received from the clinician performing the simulation and determine whether and to what degree the clinician's evaluation and/or clinical response to the clinical scenario is appropriate or otherwise clinically correct. In some implementations, the application can provide a response to the clinician regarding whether and to what degree the clinician's evaluation and/or clinical response was correct prior to continuing with the simulation. For example, if the clinician's evaluation and/or response is correct, the application can provide a response to the clinician informing the clinician that he/or she correctly evaluated and/or responded to the clinical scenario. On the other hand, if the clinician's evaluation and/or response is incorrect, the application can inform the clinician accordingly and provide the clinician with information describing the correct evaluation and/or response to the clinical scenario. The interactive procedure application can further continue to provide the clinician with additional information simulating a course of care of the patient that is reactionary to the clinician's preceding clinical evaluation and/or response. For example, based on feedback received from the clinician stating the hypothetical patient should be administered a particular drug, the application can provide the clinician with information describing a complication or negative reaction to the drug and ask the clinician how to respond (e.g., if the complication or negative reaction is the expected event as determined based on known or historical information regarding actual similar past clinical scenarios).

In various embodiments, the simulation can proceed to cover a course of care of a patient until the course of care has been completed based on a defined result for the course of care. For example, with respect to labor, the simulation can cover the entire labor process until the infant (or infants) is born and both the mother and infant are in a healthy stable condition. In this regard, the interactive application can provide the clinician with information simulating events and conditions associated with the patient, the infant, and one or more contextual parameters that may occur over a course of labor, and receive feedback from the clinician regarding whether and how to respond to the events and conditions. The interactive application can further evaluate the clinician's response and guide the clinician with what the correct responses should be if the clinician provides feedback that suggests an incorrect response, or feedback stating the clinician does not know how to respond. In another example embodiment, the simulation can simulate performance of an operation.

Accordingly, in various embodiments, the procedure training module 1502 can develop and provide an interactive procedure simulation application that can be or include a gaming type application that presents a clinician with information regarding a hypothetical clinical scenario, receives feedback from the clinician responding to events and conditions that arise in the hypothetical clinically scenario, evaluates the clinicians feedback, and dynamically adapts subsequent events and conditions based on the clinician's feedback.

The medium via which the interactive procedure simulation application operates can vary. For example, in one implementation, the application can include a software gaming application that presents the clinician with information (e.g., text, images, prompts, etc.) describing the events and/or conditions via a GUI rendered via a display at a client device 150, and/or via an interactive audio medium. According to this example, the application can receive feedback from the clinician via a suitable input mechanism of the client device (e.g., touchscreen, keypad, voice to text, etc.) regarding the clinician's evaluation and/or suggested response to the event, condition and parameters that arise over the simulation. In some embodiments, the interactive simulation application can be or include a virtual reality (VR) gaming application that provides the clinician with an immersive, real-world visual environment at which the hypothetical clinical scenario being simulated is occurring. For example, the environment can include one or more patients the clinician is treating in the hypothetical clinical scenario, the actual layout at the facility, tools, instruments, medications, other clinicians involved, and the like. The clinician can further receive visual, audible and/or text prompts regarding hypothetical, live feedback information 154 that is received related to the simulated clinical scenario. The clinician can further employ an avatar or the like and cause the avatar to respond to the clinical scenario based on the clinician's evaluation of the hypothetical feedback. According to these embodiments, feedback received from the clinician can be based on a manner in which the clinician's avatar interacts with graphical elements, objects, people, etc. depicted in the VR environment, as well as verbal feedback (e.g., natural language) provided by the clinician, and other input provided by the clinician.

In another example embodiment, the interactive simulation application can be or include an augmented reality (AR) application that presents the clinician with graphical elements, objects, people, etc., projected as overlays onto a real-world environment viewed by the clinician via an AR device. For example, the clinician can wear AR glasses, goggles, contact lenses, and the like, configured to display graphical elements thereon that are aligned with the clinician's real-world environment. For instance, a clinician can be located in an operating room with actual physical medical instruments, and operate on a virtual patient that is rendered via the AR display (or in some implementations as hologram). With these embodiments, the simulation application can receive feedback in the form of natural language spoken by the clinician, as well as sensory feedback regarding motions and/or movement of the clinician and/or the medical instruments used by the clinician relative to the projected AR elements (e.g. a virtual patient). For example, the interactive application can receive the workflow data 106, clinician data 108 and the like in the manners discussed infra with reference to system 100.

In various embodiments, the procedure training module 1502 can develop the information used to simulate the hypothetical live feedback information, events, conditions and contextual parameters associated with a clinical scenario (or procedure, course of care, etc.), and the correct evaluation and responses to the events and conditions based on the historical healthcare delivery information 148 and the information included in the one or more healthcare information sources 112. For example, the procedure training module 1502 can evaluate the SOP data 114 and historical healthcare delivery information 148, for a particular procedure, course of care, etc., and learn the different events/conditions, contextual parameters, etc. that occurred, the correct manner for reacting to the events and conditions that resulted in positive clinical/financial outcomes and the like. Using machine learning, the procedure training module 1502 can further develop a model for the procedure that defines a correct progression of event/conditions associated with the procedure, correct and incorrect clinical responses and evaluations of the events and/or conditions, complications and different scenarios that arise, the reactions to the complications, and the like. The procedure training module 1502 can further employ the model to generate information simulating a hypothetical progression of events and conditions associated with performance of the procedure. The procedure training module 1502, can further employ the historical healthcare delivery information 148 and the information provided by the one or more healthcare information sources 112 to determine, in real-time during a simulation, the reactionary events and conditions that have historically and/or been known to occur, in response to different evaluations and/or responses provided by the clinician during the simulation. In some implementations, the procedure training module 1502 can employ machine learning analysis of the historical healthcare delivery information 148 to identify historical procedural workflows that are associated with repeated mistakes or adverse outcomes. The procedure training module 1502 can employ these historical workflows to generate simulated re-plays of these workflow scenarios to train clinicians to provide the correct evaluations and reactions to significant events and conditions that have been attributed to the adverse outcomes.

In various embodiments, the disclosed procedure simulation application can facilitate training a clinician in real-time during a simulation by providing immediate feedback regarding correct and incorrect evaluations and responses to events and conditions that are presented to the clinician over the course of the simulation. In addition, the procedure training module 1502 can also be configured to log or record (e.g., using the logging component 310) information regarding a clinician's performance of the simulation, including what the clinician's evaluations and proposed (or simulated) responses to clinical scenarios, information regarding what the clinician did and did not do correctly, and the like, as historical procedure training information 1504. The procedure training module 1502 can further employ recorded historical procedure training information 1504 for various additional purposes.

For example, in one embodiment, the procedure training module 1502 can evaluate the historical procedure training information 1504 for a particular clinician using machine learning to determine a level of proficiency of the clinician in association with performing certain procedures, procedural steps, and the like. In this regard, the procedure training module 1502 can learn what the clinician is good at, where the clinician makes mistakes, frequency of the mistake, conditions associated with the mistakes and the like. The procedure training module 1502 can further update the HR data 120 for the clinician based on the historical procedure training information to describe the clinician's abilities and/or level of proficiency in certain medical practices, procedures, clinical scenarios, diagnosis, conditions, and the like. As discussed supra, in some implementations, the live healthcare delivery guidance module 132 can further employ the HR data 120 in association with determining appropriate responses for clinicians in a live clinical scenario. For example, in some implementations, the procedure training module 1502 can determine an appropriate clinician to perform a particular procedure, procedural step, and the like, based on the clinicians available and information regarding their capabilities and/or level of proficiency level with respect to the procedure or procedural step.

In another embodiment, the procedure training module 1502 can employ the historical procedure training information 1504 to facilitate tailoring simulations based to a clinician. In this regard, the procedure training module 1502 can tailor the simulation to focus on areas where the clinician needs practice or improvement. For example, the procedure training module 1502 can employ information regarding aspects of a clinical scenario, procedure, course of care and the like, that the clinician tends to perform incorrectly or poorly. The procedure training module 1502 can then tailor subsequent simulations to present the clinician with information pertaining to similar clinical events, conditions, contexts, etc., that the clinician is deficient in.

In various additional embodiments, the historical procedure training information 1504 can be employed to determine a level of proficiency or competency and expertise of a clinician in association with performing a procedure and/or responding to various clinical scenarios, including unforeseen clinical scenarios. The clinician's level of expertise and proficiency can further be employed in association with receiving authorization to perform the procedure in an actual patient setting, hiring and firing clinicians, determining salary, determining insurance premiums for the clinician and the like. The procedure training module 1502 can also employ recorded, historical healthcare delivery information 148 regarding clinician performance in an actual live or real patient setting to further tailor and continue to evaluate the clinicians level or proficiency, competency and expertise in association with clinical practice.

The patient intake allocation module 1506 can be configured to employ machine learning to determine an appropriate medical facility to send a patient and/or where a medical procedure required for the patient should be performed based on contextual factors including but not limited to: the current physiological state/condition of the patient, the location of the patient relative to one or more healthcare facilities, the medical services provided by the respective medical facilities, the capabilities of the respective medical facilities to provide the proper treatment to for the patient, the insurance held by the patient, the resources available at the respective healthcare facilities (e.g., including medical supplies, equipment and personnel) and the like. For example, in many emergency scenarios, the ambulatory services or paramedics are instructed to take the patient to the nearest healthcare facility having an emergency department. However, the nearest emergency room may not be the most appropriate place to take the patient based on the various contextual parameters noted above. For example, in one scenario, the waiting time before the patient can be seen at the nearest healthcare facility may be over two hours while the waiting time at a second healthcare facility another thirty minutes away may be less than five minutes. Further, based on the state of the patient, if the patient is forced to wait over two hours before being seen, the patient could begin to exhibit some severe complications. In this scenario, the second healthcare facility would be the most appropriate location to take the patient. In accordance with this example, the patient intake allocation module 1506 can receive live feedback regarding the context of the patient, live information regarding the state or context of the nearby healthcare facilities, information regarding locations of the healthcare facilities, and the like, and employ AI and machine learning to determine the most appropriate location to send the patient.

The litigation forecasting module 1508 can be configured to evaluate logged, historical healthcare delivery information 148 for respective patients regarding the treatment they received in association with a procedure, course of care, or the like, to make inferences or determination regarding a probability of the medical organization (or a clinician) receiving a lawsuit from the patient or beneficiary of the patient. The litigation forecasting module 1508 can also determine or infer a probability the medical organization or clinician would be held at fault at trial, a monetary amount the medical organization will likely be held liable for, whether the case should be tried or settled through negotiation, and the like. In this regard, following completion of a medical procedure or course of care of a patient, using machine learning analysis of the historical healthcare delivery information for the procedure or course of care, the litigation forecasting module 1508 can determine litigation review information, including information regarding but not limited to: if errors were made, if the procedure or course of care involved an adverse clinical outcome, a degree of severity of the adverse clinical outcome, whether errors were made that are or could be attributed to the adverse clinical outcome, and the like. If no errors and adverse complications or outcomes were identified, the litigation forecasting module 1508 can determine or infer the probability of litigation regarding the case is less than X % (e.g., 1.0%). However, if errors or complications are identified, the litigation forecasting module 1508 can compare the errors and/or complications to similar cases including similar errors and complications that were previously associated with a lawsuit. This information can be included in historical litigation information 1510.

For example, the historical litigation information 1510 can include information for past medical cases performed by the healthcare organization (or disparate healthcare organizations) that received a lawsuit, including the basis of the lawsuit, the facts of the case, the outcome of the lawsuit (e.g., dismissed, settled, settlement amount, tried, decision on trial, liable amount determined at trial if not dismissed, etc.), and the like. Using machine learning analysis of similar cases included in the historical litigation information 1510 involving same or similar errors and complications, the litigation forecasting module 1508 can determine or infer information included but not limited to: a probability the medical organization (or a particular clinician) will receive a lawsuit from the patient or beneficiary of the patient, a probability the medical organization or clinician would be held at fault at trial, a monetary amount the medical organization will likely be held liable for, whether the case should be tried or settled through negotiation, and the like.

In some embodiments, the litigation forecasting module 1508 can be configured to notify the medical organization or another entity (e.g., an insurance company of the medical organization, the patient, the beneficiary of the patient, the insurance company of the patient, etc.) regarding the evaluation of the case and the probability of litigation and associated information regardless of the outcome of the evaluation. In other implementations, the litigation forecasting module 1508 can be configured to flag cases with an evaluation associated with a probability of litigation above N % (e.g., above 40%, 50%, 75%, etc.) and/or a potential liability for a monetary amount above a threshold amount. The litigation forecasting module 1508 can further be configured to notify the medical organization (or another defined entity), regarding any flagged cases.

Example Operating Environments

The systems and processes described below can be embodied within hardware, such as a single integrated circuit (IC) chip, multiple ICs, an application specific integrated circuit (ASIC), or the like. Further, the order in which some or all the process blocks appear in each process should not be deemed limiting. Rather, it should be understood that some of the process blocks can be executed in a variety of orders, not all of which may be explicitly illustrated in this disclosure.

Figure 16:
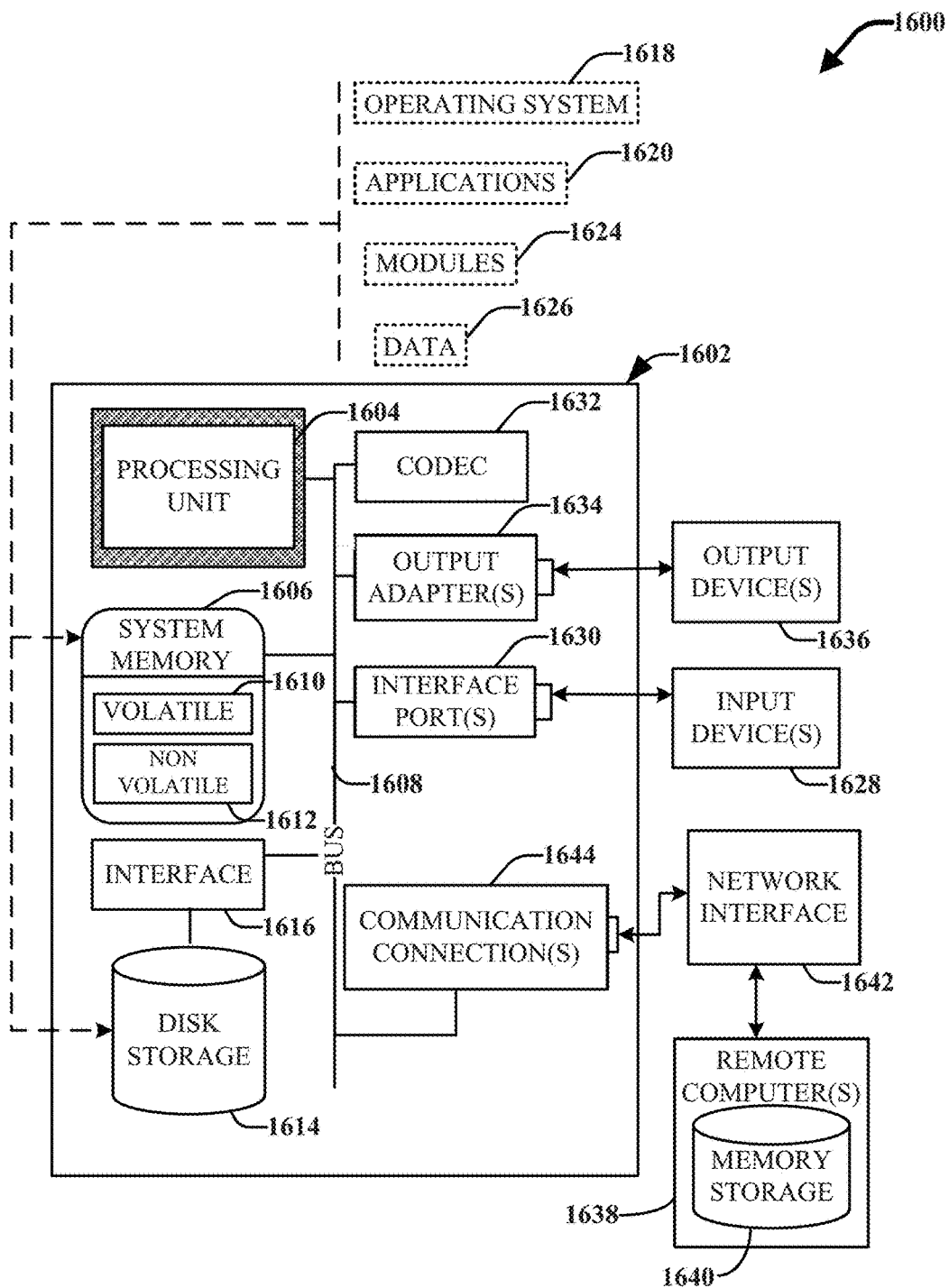
FIG. 16 is a schematic block diagram illustrating a suitable operating environment in accordance with various aspects and embodiments.

With reference to FIG. 16, a suitable environment 1600 for implementing various aspects of the claimed subject matter includes a computer 1602. The computer 1602 includes a processing unit 1604, a system memory 1606, a codec 1632, and a system bus 1608. The system bus 1608 couples system components including, but not limited to, the system memory 1606 to the processing unit 1604. The processing unit 1604 can be any of various available processors. Dual microprocessors and other multiprocessor architectures also can be employed as the processing unit 1604.

The system bus 1608 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1694), and Small Computer Systems Interface (SCSI).

The system memory 1606 includes volatile memory 1610 and non-volatile memory 1612. The basic input/output system (BIOS), containing the basic routines to transfer information between elements within the computer 1602, such as during start-up, is stored in non-volatile memory 1612. In addition, according to present innovations, codec 1632 may include at least one of an encoder or decoder, wherein the at least one of an encoder or decoder may consist of hardware, a combination of hardware and software, or software. Although, codec 1632 is depicted as a separate component, codec 1632 may be contained within non-volatile memory 1612. By way of illustration, and not limitation, non-volatile memory 1612 can include read only memory (ROM), programmable ROM (PROM), electrically programmable ROM (EPROM), electrically erasable programmable ROM (EEPROM), or flash memory. Volatile memory 1610 includes random access memory (RAM), which acts as external cache memory. According to present aspects, the volatile memory may store the write operation retry logic (not shown in FIG. 16) and the like. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM.

Computer 1602 may also include removable/non-removable, volatile/non-volatile computer storage medium. FIG. 16 illustrates, for example, disk storage 1614. Disk storage 1614 includes, but is not limited to, devices like a magnetic disk drive, solid state disk (SSD) floppy disk drive, tape drive, Jaz drive, Zip drive, LS-70 drive, flash memory card, or memory stick. In addition, disk storage 1614 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1614 to the system bus 1608, a removable or non-removable interface is typically used, such as interface 1616.

It is to be appreciated that FIG. 16 describes software that acts as an intermediary between users and the basic computer resources described in the suitable operating environment 1600. Such software includes an operating system 1618. Operating system 1618, which can be stored on disk storage 1614, acts to control and allocate resources of the computer system 1602. Applications 1620 take advantage of the management of resources by operating system 1618 through program modules 1624, and program data 1626, such as the boot/shutdown transaction table and the like, stored either in system memory 1606 or on disk storage 1614. It is to be appreciated that the claimed subject matter can be implemented with various operating systems or combinations of operating systems.

A user enters commands or information into the computer 1602 through input device(s) 1628. Input devices 1628 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1604 through the system bus 1608 via interface port(s) 1630. Interface port(s) 1630 include, for example, a serial port, a parallel port, a game port, and a universal serial bus (USB). Output device(s) 1636 use some of the same type of ports as input device(s). Thus, for example, a USB port may be used to provide input to computer 1602, and to output information from computer 1602 to an output device 1636. Output adapter 1634 is provided to illustrate that there are some output devices 1636 like monitors, speakers, and printers, among other output devices 1636, which require special adapters. The output adapters 1634 include, by way of illustration and not limitation, video and sound cards that provide a means of connection between the output device 1636 and the system bus 1608. It should be noted that other devices and/or systems of devices provide both input and output capabilities such as remote computer(s) 1638.

Computer 1602 can operate in a networked environment using logical connections to one or more remote computers, such as remote computer(s) 1638. The remote computer(s) 1638 can be a personal computer, a server, a router, a network PC, a workstation, a microprocessor based appliance, a peer device, a smart phone, a tablet, or other network node, and typically includes many of the elements described relative to computer 1602. For purposes of brevity, only a memory storage device 1640 is illustrated with remote computer(s) 1638. Remote computer(s) 1638 is logically connected to computer 1602 through a network interface 1642 and then connected via communication connection(s) 1644. Network interface 1642 encompasses wire and/or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1644 refers to the hardware/software employed to connect the network interface 1642 to the bus 1608. While communication connection 1644 is shown for illustrative clarity inside computer 1602, it can also be external to computer 1602. The hardware/software necessary for connection to the network interface 1642 includes, for exemplary purposes only, internal and external technologies such as, modems including regular telephone grade modems, cable modems and DSL modems, ISDN adapters, and wired and wireless Ethernet cards, hubs, and routers.

Figure 17:
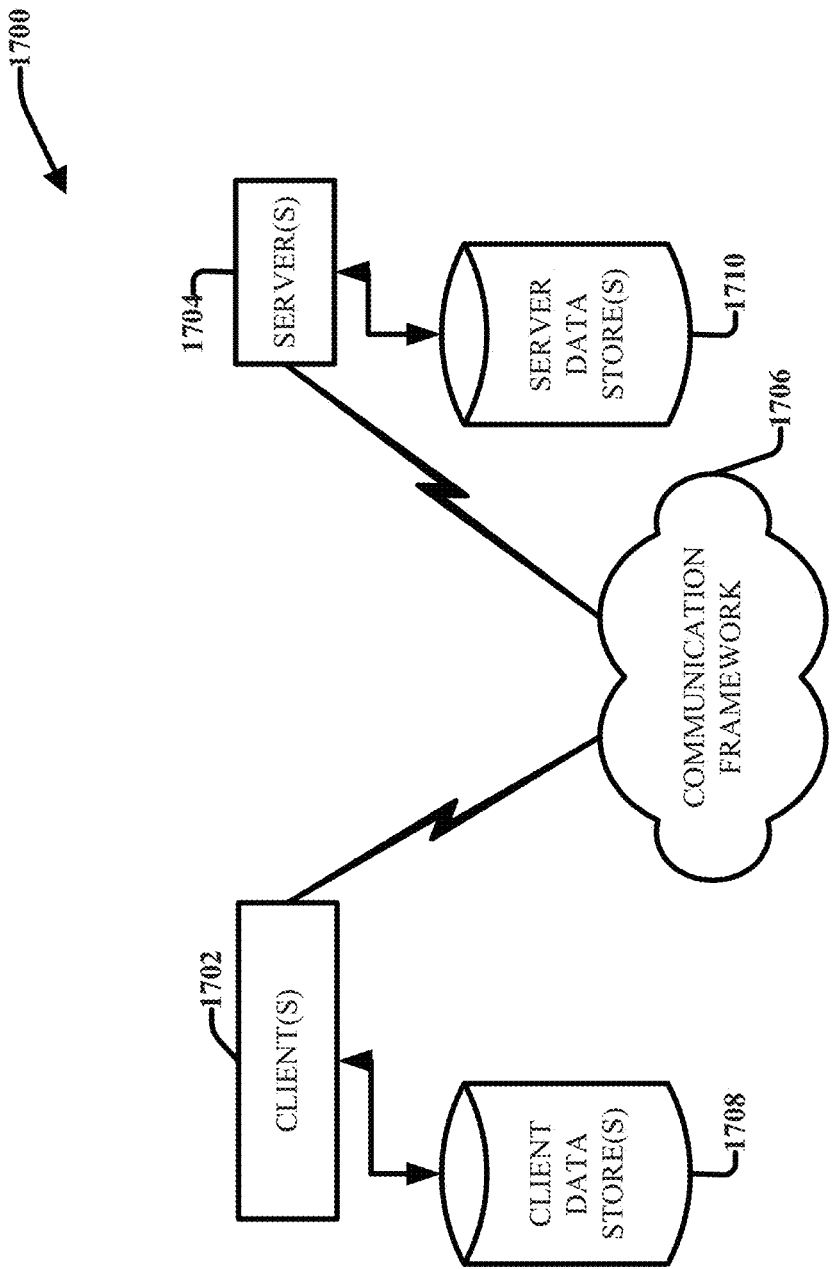
FIG. 17 is a schematic block diagram of a sample-computing environment in accordance with various aspects and embodiments.

Referring now to FIG. 17, there is illustrated a schematic block diagram of a computing environment 1700 in accordance with this disclosure. The system 1700 includes one or more client(s) 1702 (e.g., laptops, smart phones, PDAs, media players, computers, portable electronic devices, tablets, and the like). The client(s) 1702 can be hardware and/or software (e.g., threads, processes, computing devices). The system 1700 also includes one or more server(s) 1704. The server(s) 1704 can also be hardware or hardware in combination with software (e.g., threads, processes, computing devices). The servers 1704 can house threads to perform transformations by employing aspects of this disclosure, for example. One possible communication between a client 1702 and a server 1704 can be in the form of a data packet transmitted between two or more computer processes wherein the data packet may include video data. The data packet can include a metadata, e.g., associated contextual information, for example. The system 1700 includes a communication framework 1706 (e.g., a global communication network such as the Internet, or mobile network(s)) that can be employed to facilitate communications between the client(s) 1702 and the server(s) 1704.

Communications can be facilitated via a wired (including optical fiber) and/or wireless technology. The client(s) 1702 include or are operatively connected to one or more client data store(s) 1708 that can be employed to store information local to the client(s) 1702 (e.g., associated contextual information). Similarly, the server(s) 1704 are operatively include or are operatively connected to one or more server data store(s) 1710 that can be employed to store information local to the servers 1704.

In one embodiment, a client 1702 can transfer an encoded file, in accordance with the disclosed subject matter, to server 1704. Server 1704 can store the file, decode the file, or transmit the file to another client 1702. It is to be appreciated, that a client 1702 can also transfer uncompressed file to a server 1704 and server 1704 can compress the file in accordance with the disclosed subject matter. Likewise, server 1704 can encode video information and transmit the information via communication framework 1706 to one or more clients 1702.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described in this description can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described in this disclosure for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the disclosure illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described in this disclosure may also interact with one or more other components not specifically described in this disclosure but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable storage medium; software transmitted on a computer readable transmission medium; or a combination thereof.

Moreover, the words "example" or "exemplary" are used in this disclosure to mean serving as an example, instance, or illustration. Any aspect or design described in this disclosure as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used in this description differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described in this disclosure. Furthermore, not all illustrated acts may be required to implement the methodologies in accordance with certain aspects of this disclosure. In addition, those skilled in the art will understand and appreciate that the methodologies could alternatively be represented as a series of interrelated states via a state diagram or events. Additionally, it should be appreciated that the methodologies disclosed in this disclosure are capable of being stored on an article of manufacture to facilitate transporting and transferring such methodologies to computing devices. The term article of manufacture, as used in this disclosure, is intended to encompass a computer program accessible from any computer-readable device or storage media.

What is claimed is:

1. A system, comprising:
a memory that stores computer executable components;
a processor that executes the computer executable components stored in the memory, wherein the computer executable components comprise:
a monitoring component that monitors live feedback information received over a current course of care of a patient, wherein the live feedback information comprises physiological information regarding a physiological state of the patient and workflow information regarding medical treatment provided to the patient in association with a defined clinical workflow for the current course of care, wherein the workflow information comprises clinician information regarding one or more clinicians responsible for treating the patient in association with the current course of care, including identities of the one or more clinicians, a current level of fatigue of the one or more clinicians and a current workload of the one or more clinicians;
a model development component that employs one or more machine learning processes to:
analyze historical information comprising previously logged live feedback information for other patients to learn first correlations between historical events and conditions associated with historical courses of care for the other patients and the defined clinical workflow that caused a clinician to perform one or more responses and levels of risk associated with failure to provide the one or more responses, and second correlations between how varying fatigue levels and workloads of respective clinicians that performed the same or similar course of care impact the historical events and conditions, and
train one or more neural network models to classify the historical events or conditions as being significant or not significant based on the first and second correlations;
a significant event/condition identification that employs the one or more neural network models to classify current events or conditions associated with the current course of care as being significant or not significant based on the live feedback information; and
a notification component that generates a notification in response to a determination by the significant event/condition identification component that a current event or condition associated with the current course of care warrants a response based on the one or more neural network models classifying the current event or condition as being significant, the notification comprising information identifying the current event or condition and indicating the current event or condition warrants the response and provides the notification to a device associated with an entity involved with treating the patient in association with the current course of care.

2. The system of claim 1, wherein the courses of care comprise same or similar courses of care to the current course of care, and wherein the significant event/condition identification component further analyzes one or more standard operating procedures defined for the current course of care using the one or more machine learning processes to determine whether the current events or conditions associated with the current course of care warrant the response.

3. The system of claim 1, wherein the significant event/condition identification component determines the levels of risk based on one or more adverse clinical outcomes associated with the failure to provide the one or more responses.

4. The system of claim 1, wherein the significant event/condition identification component determines the levels of risks are based on one or more adverse financial outcomes associated with the failure to provide the one or more responses.

5. The system of claim 1, wherein the notification comprises a mechanism for providing an acknowledgment indicating the notification was received, and wherein the computer executable components further comprise:
an acknowledgment component configured to track information regarding whether the acknowledgment was received and timing of reception of the acknowledgment.

6. The system of claim 1, wherein the computer executable components further comprise:
an interface component that updates a graphical user interface in real-time to reflect occurrence of the current event or condition, wherein the graphical user interface tracks the current events and conditions associated with the current course of care in real-time; and,
a monitoring parameter update component configured to determine one or more parameters related to the current event or condition, and wherein the interface component is further configured update the graphical use interface to comprise information that tracks the one or more parameters.

7. The system of claim 1, wherein the response comprises a recommended clinical response for performance by one or more clinicians responsible for providing medical treatment to the patient in association with the current course of care, and wherein the computer executable components further comprise:
a response component that employs one or more additional machine learning processes to determine the recommended clinical response based on the current event or condition, and wherein the notification identifies the recommended clinical response.

8. The system of claim 7, wherein the response component determines the response based on information regarding the one or more clinicians, including at least one of, a current level of fatigue of the one or more clinicians, a current workload of the one or more clinicians, and historical performance information for the one or more clinicians.

9. The system of claim 1, wherein the computer executable components further comprise:
a risk/severity component that employs one or more additional machine learning processes to determine inferred levels of risk respectively associated with the current events or conditions based on the live feedback information and the correlations, wherein the significant event/condition identification determines whether the current events or conditions warrant the response based on the inferred levels of risk, and wherein the inferred levels of risk reflect a probability of occurrence of an adverse outcome as a result of a failure to perform the response.

10. The system of claim 1, wherein the levels of risk are based on one or more historical adverse clinical or financial outcomes associated with the failure to provide the one or more responses.

11. A method, comprising:
using a processor to execute the following computer executable instructions stored in a memory to perform the following acts:
monitoring live feedback information received over a course of care of a patient, wherein the live feedback information comprises physiological information regarding a physiological state of the patient and workflow information regarding medical treatment provided to the patient in association with a defined clinical workflow for the course of care, wherein the workflow information comprises clinician information regarding one or more clinicians responsible for treating the patient in association with the current course of care, including identities of the one or more clinicians, a current level of fatigue of the one or more clinicians and a current workload of the one or more clinicians;
employing one or more machine learning processes to:
analyze historical information comprising previously logged live feedback information for other patients to learn first correlations between historical events and conditions associated with historical courses of care for the other patients and the defined clinical workflow that caused a clinician to perform one or more responses and levels of risk associated with failure to provide the one or more responses, and second correlations between how varying fatigue levels and workloads of respective clinicians that performed the same or similar course of care impact the historical events and conditions, and
train one or more neural network models to classify the historical events or conditions as being significant or not significant based on the first and second correlations; and
employing the one or more neural network models to classify current events or conditions associated with the current course of care as being significant or not significant based on the live feedback information;
generating, in response to a determination that a current event or condition warrants a response based on the one or more neural network models classifying the current event or condition as being significant, a notification comprising information identifying the current event or condition and indicating the current event or condition warrants the response; and
providing the notification to a device associated with an entity involved with treating the patient in association with the current course of care.

12. The method of claim 11, wherein the courses of care comprise same or similar courses of care to the current course of care, and wherein the significant event/condition identification component further analyzes one or more standard operating procedures defined for the current course of care using the one or more machine learning processes to determine whether the current events or conditions associated with the current course of care warrant the response.

13. The method of claim 11, wherein the employing the one or more machine learning processes comprises determining the levels of risk based on one or more adverse clinical outcomes associated with the failure to provide the one or more responses.

14. The method of claim 11, wherein the employing the one or more machine learning processes comprises determining the levels of risks based on one or more adverse financial outcomes associated with the failure to provide the one or more responses.

15. The method of claim 11, wherein the notification comprises a mechanism for providing an acknowledgment indicating the notification was received, and wherein the method further comprises:
tracking information regarding whether the acknowledgment was received and timing of reception of the acknowledgment.

16. The method of claim 11, further comprising:
updating a graphical user interface in real-time to reflect occurrence of the current event or condition, wherein the graphical user interface tracks the current events and conditions associated with the current course of care in real-time.

17. The method of claim 11, wherein the levels of risk are based on one or more historical adverse clinical or financial outcomes associated with the failure to provide the one or more responses.

18. A non-transitory computer-readable storage medium comprising computer-readable instructions that, in response to execution, cause a computing system to perform operations, comprising:
monitoring component live feedback information received over a course of care of a patient, wherein the live feedback information comprises physiological information regarding a physiological state of the patient and workflow information regarding medical treatment provided to the patient in association with a defined clinical workflow followed over the course of care, wherein the workflow information comprises clinician information regarding one or more clinicians responsible for treating the patient in association with the current course of care, including identities of the one or more clinicians, a current level of fatigue of the one or more clinicians and a current workload of the one or more clinicians;
employing one or more machine learning processes to:
analyze historical information comprising previously logged live feedback information for other patients to learn first correlations between historical events and conditions associated with historical courses of care for the other patients and the defined clinical workflow that caused a clinician to perform one or more responses and levels of risk associated with failure to provide the one or more responses, and second correlations between how varying fatigue levels and workloads of respective clinicians that performed the same or similar course of care impact the historical events and conditions, and
train one or more neural network models to classify the historical events or conditions as being significant or not significant based on the first and second correlations; and employing the one or more neural network models to classify current events or conditions associated with the current course of care as being significant or not significant based on the live feedback information;

generating, in response to a determination that a current event or condition warrants a response based on the one or more neural network models classifying the current event or condition as being significant, a notification comprising information identifying the current event or condition and indicating the current event or condition warrants the response; and providing the notification to a device associated with an entity involved with treating the patient in association with the current course of care.

* * * * *